(12) United States Patent
Grillberger et al.

(10) Patent No.: US 8,852,888 B2
(45) Date of Patent: Oct. 7, 2014

(54) METHOD OF PRODUCING RECOMBINANT HIGH MOLECULAR WEIGHT VWF IN CELL CULTURE

(75) Inventors: Leopold Grillberger, Vienna (AT); Manfred Reiter, Vienna (AT); Wolfgang Mundt, Vienna (AT)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 253 days.

(21) Appl. No.: 13/179,386

(22) Filed: Jul. 8, 2011

(65) Prior Publication Data

US 2012/0035110 A1   Feb. 9, 2012

Related U.S. Application Data

(60) Provisional application No. 61/362,635, filed on Jul. 8, 2010.

(51) Int. Cl.
*C12P 21/04* (2006.01)
*C12P 21/06* (2006.01)

(52) U.S. Cl.
USPC .................................. 435/69.6; 435/69.1

(58) Field of Classification Search
USPC .................................. 435/69.6, 69.1
See application file for complete search history.

(56) References Cited

U.S. PATENT DOCUMENTS

| | | | |
|---|---|---|---|
| 4,767,704 | A | 8/1988 | Cleveland et al. |
| 5,804,420 | A | 9/1998 | Chan et al. |
| 6,100,061 | A | 8/2000 | Reiter et al. |
| 6,156,570 | A | 12/2000 | Hu et al. |
| 6,171,825 | B1 | 1/2001 | Chan et al. |
| 6,528,286 | B1 | 3/2003 | Ryll |
| 6,531,577 | B1 | 3/2003 | Kaersgaard et al. |
| 6,936,441 | B2 | 8/2005 | Reiter et al. |
| 7,335,634 | B2 | 2/2008 | Walter et al. |
| 7,709,229 | B2 | 5/2010 | Casatorres Hernandez et al. |
| 8,039,231 | B2 | 10/2011 | Luan et al. |
| 8,313,926 | B2 | 11/2012 | Grillberger et al. |
| 8,486,699 | B2 | 7/2013 | Talbot et al. |
| 2003/0077806 | A1 | 4/2003 | Selden et al. |
| 2005/0084928 | A1 | 4/2005 | Birch et al. |
| 2005/0266528 | A1 | 12/2005 | Laemmie et al. |
| 2007/0190057 | A1 | 8/2007 | Wu et al. |
| 2007/0212770 | A1 | 9/2007 | Grillberger et al. |
| 2008/0009040 | A1 | 1/2008 | Grillberger et al. |
| 2008/0064644 | A1 | 3/2008 | Hernandez et al. |
| 2009/0068705 | A1 | 3/2009 | Drapeau et al. |
| 2009/0176269 | A1 | 7/2009 | Giovagnoli et al. |
| 2009/0291064 | A1 | 11/2009 | Talbot et al. |
| 2009/0317867 | A1 | 12/2009 | Luan et al. |
| 2010/0227819 | A1 | 9/2010 | Hernandez et al. |
| 2011/0086413 | A1 | 4/2011 | Grillberger et al. |
| 2011/0086813 | A1 | 4/2011 | Glaser et al. |
| 2011/0151512 | A1 | 6/2011 | Grillberger et al. |
| 2012/0035110 | A1 | 2/2012 | Grillberger et al. |

FOREIGN PATENT DOCUMENTS

| | | |
|---|---|---|
| EP | 0 481 791 A2 | 4/1992 |
| EP | 0 197 592 B1 | 2/1993 |
| EP | 1 096 017 A2 | 5/2001 |
| WO | WO 86/06096 A1 | 10/1986 |
| WO | WO 96/15231 A2 | 5/1996 |
| WO | WO 96/26266 A1 | 8/1996 |
| WO | WO 98/08934 A1 | 3/1998 |
| WO | WO 98/15614 A1 | 4/1998 |
| WO | WO 00/03000 A2 | 1/2000 |
| WO | WO 01/23527 A1 | 4/2001 |
| WO | WO 2007/077217 A2 | 7/2007 |
| WO | WO 2008/109410 A1 | 9/2008 |
| WO | WO 2009/086309 A2 | 7/2009 |
| WO | WO 2009/086309 A3 | 7/2009 |
| WO | WO 2011/012725 A1 | 2/2011 |
| WO | WO 2012/006591 A1 | 1/2012 |
| WO | WO 2012/006594 A1 | 1/2012 |

OTHER PUBLICATIONS

Franěk, F. et al., "Plant Protein Hydrolysates: Preparation of Defined Peptide Fractions Promoting Growth and Production in Animal Cells Cultures," *Biotechnol. Prog.*, 2000, vol. 16, pp. 688-692.

International Search Report mailed Sep. 27, 2011, for International Patent Application No. PCT/US2011/043455 filed Jul. 8, 2011, 5 pages.

International Search Report mailed Sep. 30, 2011, for International Patent Application No. PCT/US2011/043459 filed Jul. 8, 2011, 4 pages.

Mayadas, T.N. et al., "In Vitro Multimerization of von Willebrand Factor is Triggered by Low pH, Importance of the Propolypeptide and Free Sulfhydris," *The Journal of Biological Chemistry*, Aug. 15, 1989, vol. 264, No. 23, pp. 13497-13503.

Mignot, G. et al., "Production of recombinant Von Willebrand factor by CHO cells cultured in macroporous microcarriers," *Cytotechnology*, 1990, vol. 4, pp. 163-171.

Plaimauer, B. et al., "Cloning, expression, and functional characterization of the von Willebrand factor-cleaving protease (ADAMTS13)," *Blood*, Nov. 15, 2002, vol. 100, No. 10, pp. 3626-3632.

Plaimauer, B. et al., "Expression and Characterization of Recombinant Human ADAMTS-13," *Seminars in Hematology*, Jan. 2004, vol. 41, No. 1, pp. 24-33.

Lao, M-S. et al., "Effects of Ammonium and Lactate on Growth and Metabolism of a Recombinant Chinese Hamster Ovary Cell Culture," Biotechnol. Prog., 1997, vol. 13, pp. 689-691.

*Primary Examiner* — Marcia S Noble

(74) *Attorney, Agent, or Firm* — Morgan, Lewis & Bockius LLP

(57) ABSTRACT

Among other aspects, the present invention relates to cell culture conditions for producing high molecular weight vWF, in particular, highly multimericWF with a high specific activity and ADAMTS13 with a high specific activity. The cell culture conditions of the present invention can include, for example, a cell culture medium with an increased copper concentration and/or cell culture supernatant with a low ammonium ($NH_4^+$) concentration. The present invention also provides methods for cultivating cells in the cell culture conditions to express high molecular weight vWF and rA13 having high specific activities.

35 Claims, 11 Drawing Sheets

| Lane Number | Band Number | Trace Int x mm | Relative Qty |
|---|---|---|---|
| 1 | 1 | 809715.2 | 74.5 |
| 1 | 2 | 277519.7 | 25.5 |
| 2 | 1 | 681110.1 | 83.7 |
| 2 | 2 | 132376.5 | 16.3 |
| 3 | 1 | 568177 | 90.2 |
| 3 | 2 | 61619.3 | 9.8 |
| 4 | 1 | 500725.4 | 94.0 |
| 4 | 2 | 31815.3 | 6.0 |
| 5 | 1 | 433194.4 | 95.9 |
| 5 | 4 | 18307.3 | 4.1 |
| 6 | 1 | 412190.2 | 95.9 |
| 6 | 2 | 17441 | 4.1 |
| 7 | 1 | 842215.1 | 72.0 |
| 7 | 2 | 327960.1 | 28.0 |
| 8 | 1 | 723836.4 | 70.5 |
| 8 | 2 | 303095.4 | 29.5 |
| 9 | 1 | 739912.7 | 68.7 |
| 9 | 2 | 337575.1 | 31.3 |
| 10 | 1 | 929848.4 | 68.6 |
| 10 | 2 | 425784.2 | 31.4 |
| 11 | 1 | 684679.9 | 78.6 |
| 11 | 2 | 185964.5 | 21.4 |
| 12 | 3 | 512298.6 | 66.7 |
| 12 | 4 | 256326.7 | 33.3 |

| Lane Number | Band Number | Trace Int x mm | Relative Qty |
|---|---|---|---|
| 1 | 1 | 155657.0 | 97.2 |
| 1 | 2 | 4453.3 | 2.8 |
| 2 | 1 | 419998.6 | 87.6 |
| 2 | 2 | 59416.6 | 12.4 |
| 3 | 1 | 225344.4 | 97.4 |
| 3 | 2 | 5898.2 | 2.6 |
| 4 | 1 | 557340.0 | 73.2 |
| 4 | 2 | 203807.5 | 26.8 |
| 5 | 1 | 248653.8 | 97.8 |
| 5 | 2 | 5599.8 | 2.2 |
| 6 | 1 | 434040.2 | 95.4 |
| 6 | 2 | 20823.4 | 4.6 |
| 7 | 1 | 238580.2 | 97.9 |
| 7 | 2 | 5159.7 | 2.1 |
| 8 | 1 | 322940.6 | 77.3 |
| 8 | 2 | 94677.8 | 22.7 |
| 9 | 1 | 250356.6 | 98.0 |
| 9 | 2 | 5183.5 | 2.0 |
| 10 | 1 | 275819.1 | 97.7 |
| 10 | 2 | 6469.7 | 2.3 |
| 11 | 1 | 207447.3 | 97.3 |
| 11 | 2 | 5687.5 | 2.7 |
| 12 | 1 | 604779.1 | 76.2 |
| 12 | 2 | 189356.4 | 23.8 |

METHOD OF PRODUCING RECOMBINANT HIGH MOLECULAR WEIGHT VWF IN CELL CULTURE

CROSS REFERENCES TO APPLICATIONS

This application claims priority to U.S. Provisional Patent Application Ser. No. 61/362,635, filed Jul. 8, 2010, the disclosure of which is hereby incorporated herein by reference in its entirety for all purposes.

BACKGROUND OF THE INVENTION

The recombinant expression of therapeutic proteins in cell culture (particularly large-scale cell cultures), including eukaryotic cell culture, and more specifically mammalian cell culture, requires the use of special culture media providing nutrient substances for efficient growth of cells. Cell culture media formulations are often supplemented with a range of additives, including fetal calf serum (FCS), animal derived proteins and/or protein hydrolysates of bovine origin as well as protein hydrolysates derived from plants or yeast. One challenge with such cultures is that the amount of protein and the total and specific activity of the protein produced are often variable across different cell cultures, even when the formulation for the cell culture media is not changed. This variability is especially apparent in the case of large-scale manufacturing processes utilizing cell culture volumes of 10 liters to over 20,000 liters. Cell culture media containing hydrolysates are particularly prone to variability from one cell culture to the next, leading to decreased production of total protein as well as decreased total and specific activity.

One potential reason for the variability seen across different cell cultures is that contaminants in additives such as hydrolysates vary from one batch to the next. In general, serum or serum-derived substances, such as, e.g., albumin, transferrin or insulin, may comprise unwanted agents that can contaminate the cell cultures and the biological products obtained thereof. Furthermore, human serum derived additives have to be tested for all known viruses, including hepatitis viruses and HIV which can be transmitted via serum. Moreover, bovine serum and products derived thereof bear the risk of BSE contamination. In addition, all serum-derived products can be contaminated by unknown substances. When using serum or protein additives derived from human or animal sources in cell culture, there are numerous problems (e.g., the varying quality in composition of different batches and the risk of contamination with mycoplasma, viruses or BSE), particularly if the cells are used in the manufacture of drugs or vaccines for human administration. Therefore, many attempts have been made to provide efficient host systems and cultivation conditions, which do not require serum or other animal protein compounds.

Such serum-free media have been developed on the basis of protein extracts derived from plants or yeast. For example, soy hydrolysates are known to be useful for fermentation processes and can enhance the growth of many fastidious organisms, yeasts and fungi. WO 96/26266 describes that papaic digests of soy meal are a source of carbohydrate and nitrogen and many of the components can be used in tissue culture. Franek et al. (Biotechnology Progress (2000) 16, 688-692) describe growth and productivity promoting effects of defined soy and wheat hydrolysate peptide fractions.

WO 96/15231 discloses a serum-free medium composed of a synthetic minimal essential medium and a yeast extract for the propagation of vertebrate cells and a virus production process. A medium formulation composed of a basal cell culture medium comprising a rice peptide and an extract of yeast and an enzymatic digest thereof, and/or a plant lipid for growth of animal cells is disclosed in WO 98/15614. A medium comprising purified soy hydrolysate for the cultivation of recombinant cells is disclosed in WO 01/23527. WO 00/03000 discloses a medium that comprises a soy hydrolysate and a yeast extract, but also requires the presence of recombinant forms of animal proteins, such as growth factors.

EP-A-0 481 791 describes a biochemically defined culture medium for culturing engineered CHO cells, which is free from protein, lipid and carbohydrate isolated from an animal source, further comprising a recombinant insulin or insulin analogue, 1% to 0.025% w/v papain digested soy peptone and putrescine. WO 98/08934 describes a serum-free eukaryotic cell culture comprising hydrolyzed soy peptides (1-1000 mg/L), 0.01 to 1 mg/L putrescine and a variety of animal-derived components, including albumin, fetuin, various hormones and other proteins. In this context, it should be noted that putrescine is also known to be comprised in standard media like DMEM/Ham's F12 in a concentration of 0.08 mg/L.

The plant and/or yeast hydrolysates, however, are undefined mixtures of oligopeptides and other unknown components and contaminants. Moreover, the quality of commercially available lots of hydrolysates varies extremely. As a result, there are large variations in the production of recombinant proteins or viral products (a variation of up to a factor of three) as a function of the lots of hydrolysates used ("lot-to-lot variation"). This drawback affects the proliferation of the cells as well as the protein expression of each cell. US 2007/0212770 describes various animal protein-free and oligopeptide-free, chemically defined culture mediums that are useful for the large-scale production of recombinant protein biopharmaceuticals.

Hemostasis involves the interaction of various hemostatic reaction routes finally leading to thrombus formation. Thrombi are deposits of blood components on the surface of the vascular wall that mainly consist of aggregated blood platelets and insoluble cross-linked fibrin. Fibrin formation is the result of the restricted proteolysis of fibrinogen by thrombin, a coagulation enzyme. Thrombin is the end product of the coagulation cascade, a succession of zymogen activations occurring on the surfaces of activated blood platelets and leucocytes, and a variety of vascular cells (for a survey, cf. K. G. Mann et al., Blood, 1990, Vol. 76, pp. 1-16).

An important function in the coagulation cascade resides in the activation of Factor X by the complex of activated Factor IX (Factor IXa) and activated Factor VIII (Factor VIIIa). A deficiency or a dysfunction of the components of this complex is associated with the blood disease known as hemophilia (J. E. Sadler & E. W. Davie: Hemophilia A, Hemophilia B, and von Willebrand's Disease, in G. Stamatoyannopoulos et al., (Eds.): The molecular basis of blood diseases. W.B. Saunders Co., Philadelphia, 1987, pp. 576-602). Hemophilia A is related to a deficiency of Factor VIII activity, whereas Hemophilia B is related to a Factor IX deficiency. Current treatment consists of a replacement therapy using pharmaceutical preparations comprised of the normal coagulation factor. Of these thrombopathies, Hemophilia A occurs more frequently, affecting approximately one out of 10,000 men. Replacement therapy in Hemophilia A patients involves the repeated administration of preparations containing normal Factor VIII by intravenous infusion. The interval between the infusions is a function of the degradation of the Factor VIII activity in blood circulation. The half-life of the Factor VIII activity after an infusion differs from one individual to another, ranging from 10 to 30 hours. Thus, a prophylactic therapy requires an infusion every two to three days. This constitutes a heavy load on the life of hemophilic patients, in particular, if the venous access has become difficult due to local citratization following frequent needle punctures for intravenous infusions.

It would be particularly advantageous if the frequency of infusions could be lowered by using Factor VIII having extended half-lives. It is well known in the art that the half-life of the non-activated Factor VIII heterodimer strongly depends on the presence of von Willebrand Factor, which exhibits a strong affinity to Factor VIII (yet not to Factor VIIIa) and serves as a carrier protein (J. E. Sadler and E. W. Davie: Hemophilia A, Hemophilia B and von Willebrand's disease, in G. Stamatoynnopoulos et al. (Eds.): The molecular basis of blood diseases. W.B. Saunders Co., Philadelphia, 1987, pp. 576-602). It is known that patients suffering from von Willebrand's disease type 3, who do not have a detectable von Willebrand Factor in their blood circulation, also suffer from a secondary Factor VIII deficiency. In addition, the half-life of intravenously administered Factor VIII in those patients is 2 to 4 hours, which is considerably shorter than the 10 to 30 hours observed in Hemophilia A patients. From these findings results that Factor VIII tends to a rapid clearance from the blood circulation and that this process is to some extent inhibited by complexation with its natural carrier, von Willebrand Factor.

Von Willebrand factor (vWF) is a glycoprotein circulating in plasma as a series of multimers typically ranging in size from about 500 to 20,000 kD (or 2 to 40 dimers of vWF). Dimers and multimeric forms of vWF are composed of 250 kD polypeptide subunits linked together by disulfide bonds. vWF mediates the initial platelet adhesion to the sub-endothelium of the damaged vessel wall; only the larger multimers also exhibiting hemostatic activity. Multimerized vWF binds to the platelet surface glycoprotein Gp1bα, through an interaction in the A1 domain of vWF, in order to facilitate platelet adhesion. It is assumed that endothelial cells secret large polymeric forms of vWF and that those forms of vWF which have a low molecular weight (low molecular weight vWF) have arisen from proteolytic cleavage. The multimers having large molecular masses are stored in the Weibel-Palade bodies of the endothelial cells and liberated upon stimulation.

Reduction of FVIII binding activity, due to either reduced vWF protein levels or lowered FVIII binding affinity, results in one of three types of von Willebrand's Disease. In addition to, or alternatively, certain types of von Willebrand's disease are characterized by an increase or decrease in the level of Gp1bα-mediated platelet association, namely in Types 2A, 2B, and 2M (summarized in Castaman et al., Disorders of Hemostasis 88(1):94-108 (2003)). As such, the modulation of vWF interactions with both FVIII and Gp1bα is a viable strategy for the treatment of both Haemophilia and von Willebrand's Disease.

Given the biological importance of vWF, there is a constant need in the art to improve ways for producing vWF for therapeutic applications. It is well known that vWF can be isolated from endogenous sources, such as human blood plasma. The isolated vWF is advantageous in that it has a high specific activity for carrying out its biological function and can, therefore, be used effectively as a therapeutic protein for treating related diseases, such as von Willebrand's disease. Typically, plasma vWF has a specific Ristocetin activity of about 100 mU/μg, but isolation from human blood plasma has disadvantages because, for example, the plasma can contain a variety of viruses, such as HIV and/or hepatitis viruses, which can be transferred to the patient. Furthermore, plasma is a limited resource and, thus, shortages of plasma can be problematic in providing enough vWF for treatment. As such, recombinant methods for producing vWF are advantageous in addressing some of the problems associated with relying on plasma as a source for vWF. For recombinant production, the full length of cDNA of vWF was cloned; the propolypeptide corresponds to amino acid residues 23 to 764 of the full length prepro-vWF (Eikenboom et al (1995) Haemophilia 1, 77 90).

Unfortunately, vWF is a molecule with complex posttranslational modifications. Also, the multimerization of the vWF dimers to large and ultralarge multimers in the Golgi apparatus is a challenge for expression in mammalian cells. For example, high molecular weight vWF expressed in cell culture of, e.g., human (primary) endothelial cells depends on the specific storage of ultralarge vWF molecules in Weibel-Palade bodies. Such cell cultures are not suitable for the production of therapeutic proteins. Other cell culture methods have been reported, and it is known that cell culture conditions can affect the production of vWF in a variety of ways. For instance, high concentrations of ammonium ($NH_4^+$) have been shown to disturb posttranslational modifications. Mayadas et al. (J. Biol. Chem., 264(23):13497-13503, 1989) demonstrated that levels of 25 mM ammonium resulted in reduced vWF multimerization in endothethial cells, which also negatively affects the specific Ristocetin activity of recombinant vWF. Reduction of multimerization is generally associated in reduction of activity, particularly specific Ristocetin activity, of recombinant vWF.

It still remains difficult to predict which parameters can positively or negatively affect production of a particular protein, especially complex glycoproteins like Factor VIII and vWF. For example, certain components of a cell culture medium have been shown to affect production of Factor VIII. As disclosed in U.S. Pat. No. 5,804,420, the addition of polyol, copper, and other trace metals can positively affect production yield of Factor VIII. As also described in WO 2009/086309, cell culture processes using copper in have been shown to improve production of Factor VIII. Expression of vWF in recombinant CHO cells has also been reported by Mignot et al. (1989). However, none of these examples provide information regarding the specific activity of vWF or its multimeric distribution.

The ADAMTS (a disintegrin and metalloproteinase with thrombospondin type I motifs) proteins are a family of metalloproteinases containing a number of conserved domains, including a zinc-dependant catalytic domain, a cystein-rich domain, a disintegrin-like domain, and at least one, and in most cases multiple, thrombospondin type I repeats (for review, see Nicholson et al., BMC Evol Biol. 2005 Feb. 4; 5(1):11). These proteins, which are evolutionarily related to the ADAM and MMP families of metalloproteinases (Jones G C, Curr Pharm Biotechnol. 2006 February; 7(1):25-31), are secreted enzymes that have been linked to a number of diseases and conditions including thrombotic thrombocytopenic purpura (TTP) (Moake J L, Semin Hematol. 2004 January; 41(1):4-14), connective tissue disorders, cancers, inflammation (Nicholson et al.), and severe *plasmodium falciparum* malaria (Larkin et al., PLoS Pathog. 2009 March; 5(3): e1000349). Because of these associations, the ADAMTS enzymes have been recognized as potential therapeutic targets for a number of pathologies (Jones G C, Curr Pharm Biotechnol. 2006 February; 7(1):25-31). Accordingly, methods of producing large yields of ADAMTS proteins having high specific activities, which are free of contaminants such as viruses, BSE, and pathogens like *Mycoplasma* bacteria, are needed.

One ADAMTS family member, ADAMTS13, cleaves von Willebrand factor (vWF) between residues Tyr 1605 and Met 1606, a function responsible for the degradation of large vWF multimers in vivo. Loss of ADAMTS13 activity has been linked to a number of conditions, such as TTP (Moake J L, Semin Hematol. 2004 January; 41(1):4-14), acute and chronic inflammation (Chauhan et al., J Exp Med. 2008 Sep. 1; 205(9):2065-74), and most recently, severe *plasmodium falciparum* malaria (Larkin et al., PLoS Pathog. 2009 March; 5(3):e1000349).

The ADAMTS13 protease is a 190 kDa glycosylated protein produced predominantly by the liver (Levy et al., Nature. 2001; 413:488-494; Fujikawa et al., Blood. 2001; 98:1662-1666; Zheng et al., J Biol. Chem. 2001; 276:41059-41063; Soejima et al., J Biochem (Tokyo). 2001; 130:475-480; and Gerritsen et al., Blood. 2001; 98:1654-1661). Much like the higher order rVWF multimers, recombinant expression of the large ADAMTS13 in mammalian cell culture presents many challenges.

Therefore, there is a need to provide cell culture conditions, particularly large-scale manufacturing culture conditions, that provide consistent total protein yield and/or consistent total and specific activity of the proteins produced between different cell cultures. Consistency among cultures in large-scale manufacturing processes is of importance in the manufacture of therapeutic proteins. There is also a need for cell culture conditions for large-scale production of rVWF with a multimeric distribution and specific Ristocetin activity comparable or higher than VWF as it is present in normal human plasma. Similarly, as ADAMTS proteins have been implicated in a number of diseases and conditions, there is a need in the art for methods of large scale production of recombinant ADAMTS proteins having high specific activities, which are suitable for pharmaceutical formulation and administration. The present invention satisfies these and other needs in the art for the production of recombinant Von Willebrand Factor and recombinant ADAMTS13.

BRIEF SUMMARY OF INVENTION

In certain aspects, the present invention is based on the surprising finding that supplementation of cell culture media used to express recombinant Von Willebrand Factor (rVWF) and recombinant ADAMTS13 (rA13) results in significantly improved protein expression and enzymatic activity.

In a first aspect, the present invention provides a method for producing a recombinant Von Willebrand Factor (rVWF) composition, the method comprising the steps of: (a) providing a basal cell culture media; (b) supplementing the basal cell culture media with copper to provide a final copper concentration of at least 2.4 µg/L; (c) providing one or more cells comprising a nucleic acid encoding a rVWF protein; (d) culturing the one or more cells in the copper supplemented cell culture media such that rVWF is expressed and excreted from the cells into a culture supernatant; and (e) recovering at least a portion of the culture supernatant, wherein the recovered supernatant has a rVWF specific ristocetin cofactor activity of at least 30 mU/µg rVWF.

In one embodiment of the methods provided above, the method further comprises a step of supplementing the basal cell culture media with a hydrolysate prior to culturing the one or more cells.

In one embodiment of the methods provided above, the hydrolysate is a plant hydrolysate. In a specific embodiment, the hydrolysate is a soy hydrolysate.

In one embodiment of the methods provided above, the basal cell culture media is an animal protein free culture media.

In one embodiment of the methods provided above, the basal cell culture media is a protein free culture media.

In one embodiment of the methods provided above, the basal cell culture media is a chemically defined culture media.

In one embodiment of the methods provided above, the final copper concentration of the copper supplemented basal cell culture media is at least 4 µg/L copper.

In one embodiment of the methods provided above, the final copper concentration of the copper supplemented basal cell culture media is between 2.4 µg/L and 20 µg/L copper.

In one embodiment of the methods provided above, the copper supplementing the basal cell culture media is provided as a copper salt, a copper chelate, or a combination thereof.

In one embodiment of the methods provided above, the copper salt is selected from the group consisting of copper sulfate, copper acetate, copper carbonate, copper chloride, copper hydroxide, copper nitrate, and copper oxide.

In one embodiment of the methods provided above, the one or more cells are mammalian cells. In a specific embodiment, the mammalian cells are CHO cells.

In one embodiment of the methods provided above, culturing the one or more cells comprises batch cultivation of the cells.

In one embodiment of the methods provided above, culturing the one or more cells comprises continuous cultivation of the cells. In a specific embodiment, the continuous cultivation of cells is performed in chemostatic mode. In another specific embodiment, the continuous cultivation of cells is performed in perfusion mode.

In one embodiment of the methods provided above, the one or more cells is cultured in at least 100 L of the supplemented basal cell culture media.

In one embodiment of the methods provided above, the cell density is maintained at less than $2.5 \times 10^6$ cells per mL during the step of culturing the one or more cells.

In one embodiment of the methods provided above, the cell density is maintained at less than $2.0 \times 10^6$ cells per mL during the step of culturing the one or more cells.

In one embodiment of the methods provided above, the cell density is maintained at less than $1.5 \times 10^6$ cells per mL during the step of culturing the one or more cells.

In one embodiment of the methods provided above, the step of recovering at least a portion of the culture supernatant comprises filtration or centrifugation to remove cells from the portion of culture supernatant.

In one embodiment of the methods provided above, the recovered supernatant has a rVWF specific ristocetin cofactor activity of at least 40 mU/µg rVWF. In a specific embodiment, the recovered supernatant has a rVWF specific ristocetin cofactor activity of at least 50 mU/µg rVWF. In a more specific embodiment, the recovered supernatant has a rVWF specific ristocetin cofactor activity of at least 60 mU/µg rVWF. In a more specific embodiment, the recovered supernatant has a rVWF specific ristocetin cofactor activity of at least 70 mU/µg rVWF. In a yet more specific embodiment, the recovered supernatant has a rVWF specific ristocetin cofactor activity of at least 80 mU/µg rVWF.

In one embodiment of the methods provided above, at least 10% of the rVWF in the supernatant is present in a high molecular weight VWF multimer of more than 10 dimers. In a specific embodiment, at least 15% of the rVWF is present in a high molecular weight VWF multimer of more than 10 dimers. In another specific embodiment, at least 20% of the rVWF is present in a high molecular weight VWF multimer of more than 10 dimers. In another specific embodiment, at least 25% of the rVWF is present in a high molecular weight VWF multimer of more than 10 dimers. In another specific embodiment, at least 30% of the rVWF is present in a high molecular weight VWF multimer of more than 10 dimers.

In one embodiment of the methods provided above, the supernatant contains high molecular weight VWF multimers of 14 to 22 dimers.

In one embodiment of the methods provided above, the $NH_4^+$ content of the culture supernatant is maintained at a concentration below 10 mM.

In one embodiment of the methods provided above, the $NH_4^+$ content of the culture supernatant is maintained at a concentration below 4 mM.

In one embodiment of the methods provided above, rVWF is co-expressed with recombinant Factor VIII (rFVIII). In a specific embodiment, the method further comprises a step of purifying rVWF away from at least 50% of the rFVIII present in the recovered supernatant. In one embodiment, the ratio of rVWF to rFVIII after the purification step is at least 10:1.

In one embodiment of the methods provided above, the method further comprises a rVWF enrichment step.

In a second aspect, the present invention provides a recombinant Von Willebrand Factor (rVWF) composition prepared by a method provided herein.

In one embodiment of the compositions provided above, the composition further comprises recombinant Factor VIII (rFVIII). In a specific embodiment, the ratio of rVWF to rFVIII is at least 10:1.

In one embodiment of the compositions provided above, the composition is formulated for pharmaceutical administration. In a specific embodiment, the composition is formulated for intravenous administration.

In a third aspect, the present invention provides a cell culture supernatant comprising recombinant Von Willebrand Factor (rVWF), wherein the supernatant is prepared by a method provided herein.

In a fourth aspect, the present invention provides a cell culture supernatant comprising recombinant Von Willebrand Factor (rVWF), wherein at least 10% of the rVWF in the supernatant is present in a high molecular weight VWF multimer of more than 10 dimers. In a specific embodiment, at least 15% of the rVWF in the supernatant is present in a high molecular weight VWF multimer of more than 10 dimers. In another specific embodiment, at least 20% of the rVWF in the supernatant is present in a high molecular weight VWF multimer of more than 10 dimers. In another specific embodiment, at least 25% of the rVWF in the supernatant is present in a high molecular weight VWF multimer of more than 10 dimers. In another specific embodiment, at least 30% of the rVWF in the supernatant is present in a high molecular weight VWF multimer of more than 10 dimers. In yet another specific embodiment of the supernatants provided above, the supernatant is prepared according to a method provided herein.

In a fifth aspect, the present invention provides a cell culture supernatant comprising recombinant Von Willebrand Factor (rVWF), wherein the supernatant contains at least 0.4 IU ristocetin cofactor activity per mL. In a specific embodiment, the supernatant contains at least 0.5 IU ristocetin cofactor activity per mL. In another specific embodiment, the supernatant contains at least 0.6 IU ristocetin cofactor activity per mL. In another specific embodiment, the supernatant contains at least 0.7 IU ristocetin cofactor activity per mL. In yet another specific embodiment of the supernatants provided above, the supernatant is prepared according to a method provided herein.

In a sixth aspect, the present invention provides a method for producing a recombinant ADAMTS13 (rA13) composition, the method comprising the steps of: (a) providing a basal cell culture media; (b) supplementing the basal cell culture media with copper to provide a final copper concentration of at least 1.0 µg/L; (c) providing one or more cells comprising a nucleic acid encoding a rA13 protein; (d) culturing the one or more cells in the copper supplemented cell culture media such that rA13 is expressed and excreted from the cells into a culture supernatant; and (e) recovering at least a portion of the culture supernatant, wherein at least 1500 Units FRETS-VWF73 activity per liter supplemented basal cell culture media per day is present in the recovered culture supernatant.

In one embodiment of the methods provided above, the basal cell culture media is an animal protein free culture media.

In one embodiment of the methods provided above, the basal cell culture media is a protein free culture media.

In one embodiment of the methods provided above, the basal cell culture media is a chemically defined culture media.

In one embodiment of the methods provided above, the final copper concentration of the supplemented basal cell culture media is at least 1 µg/L copper.

In one embodiment of the methods provided above, the final copper concentration of the supplemented basal cell culture media is at least 2 µg/L copper.

In one embodiment of the methods provided above, the final copper concentration of the supplemented basal cell culture media is at least 4 µg/L copper.

In one embodiment of the methods provided above, the final copper concentration of the supplemented basal cell culture media is between 1 µg/L and 6 µg/L copper.

In one embodiment of the methods provided above, the final copper concentration of the supplemented basal cell culture media is between 2 µg/L and 4 µg/L copper.

In one embodiment of the methods provided above, copper supplementing the basal cell culture media is provided as a copper salt, a copper chelate, or a combination thereof. In a specific embodiment, the copper salt is selected from the group consisting of copper sulfate, copper acetate, copper carbonate, copper chloride, copper hydroxide, copper nitrate, and copper oxide.

In one embodiment of the methods provided above, the one or more cells are mammalian cells. In a specific embodiment, the mammalian cells are CHO cells.

In one embodiment of the methods provided above, culturing the one or more cells comprises batch cultivation of the cells.

In one embodiment of the methods provided above, culturing the one or more cells comprises continuous cultivation of the cells. In a specific embodiment, the continuous cultivation of cells is performed in chemostatic mode. In another specific embodiment, the continuous cultivation of cells is performed in perfusion mode.

In one embodiment of the methods provided above, the one or more cells is cultured in at least 100 L of the supplemented basal cell culture media.

In one embodiment of the methods provided above, the cell density is maintained at less than $4.0 \times 10^6$ cells per mL during the step of culturing the one or more cells.

In one embodiment of the methods provided above, the cell density is maintained at less than $3.5 \times 10^6$ cells per mL during the step of culturing the one or more cells.

In one embodiment of the methods provided above, the cell density is maintained at less than $3.0 \times 10^6$ cells per mL during the step of culturing the one or more cells.

In one embodiment of the methods provided above, the cell density is maintained at less than $2.5 \times 10^6$ cells per mL during the step of culturing the one or more cells.

In one embodiment of the methods provided above, the cell density is maintained at less than $2.0 \times 10^6$ cells per mL during the step of culturing the one or more cells.

In one embodiment of the methods provided above, the cell density is maintained at less than $1.5 \times 10^6$ cells per mL during the step of culturing the one or more cells.

In one embodiment of the methods provided above, the step of recovering at least a portion of the culture supernatant comprises filtration or centrifugation to remove cells from the portion of culture supernatant.

In one embodiment of the methods provided above, at least 2000 Units FRETS-VWF73 activity per liter supplemented basal cell culture media per day is present in the recovered culture supernatant.

In one embodiment of the methods provided above, at least 2500 Units FRETS-VWF73 activity per liter supplemented basal cell culture media per day is present in the recovered culture supernatant.

In one embodiment of the methods provided above, the recovered supernatant has a rA13 specific FRETS-VWF73 activity of at least 800 mU/µg.

In a preferred embodiment of the methods provided above, the recovered supernatant has a rA13 specific FRETS-VWF73 activity of at least 1200 mU/µg.

In a more preferred embodiment of the methods provided above, the recovered supernatant has a rA13 specific FRETS-VWF73 activity of at least 1600 mU/µg.

In one embodiment of the methods provided above, the $NH_4^+$ content of the culture supernatant is maintained at a concentration below 10 mM.

In one embodiment of the methods provided above, the $NH_4^+$ content of the culture supernatant is maintained at a concentration below 5 mM.

In one embodiment of the methods provided above, the $NH_4^+$ content of the culture supernatant is maintained at a concentration below 4 mM.

In one embodiment of the methods provided above, the method further comprises a rA13 enrichment step.

In a seventh aspect, the present invention provides a cell culture supernatant comprising recombinant ADAMTS13 (rA13), wherein the supernatant is prepared by a method provided herein.

In an eighth aspect, the present invention provides a cell culture supernatant comprising recombinant ADAMTS13 (rA13), wherein the supernatant contains at least 5 U FRETS-VWF73 activity per mL. In a specific embodiment, the supernatant contains at least 6 U FRETS-VWF73 activity per mL. In another specific embodiment, the supernatant contains at least 7 U FRETS-VWF73 activity per mL. In another specific embodiment, the supernatant contains at least 8 U FRETS-VWF73 activity per mL. In another specific embodiment, the supernatant contains at least 9 U FRETS-VWF73 activity per mL. In another specific embodiment, the supernatant contains at least 10 U FRETS-VWF73 activity per mL. In yet another specific embodiment of the supernatants provided above, the supernatant is prepared according to a method provided herein.

In a ninth aspect, the present invention provides a cell culture supernatant comprising recombinant ADAMTS13 (rA13), wherein the supernatant contains at least 2 µg rA13 per mL. In a specific embodiment, the supernatant contains at least 3 µg rA13 per mL. In another specific embodiment, the supernatant contains at least 4 µg rA13 per mL. In another specific embodiment, the supernatant contains at least 5 µg rA13 per mL. In another specific embodiment, the supernatant contains at least 6 µg rA13 per mL. In yet another specific embodiment of the supernatants provided above, the supernatant is prepared according to a method provided herein.

In a tenth aspect, the present invention provides a recombinant ADAMTS13 (rA13) composition prepared by a method according to any one of the methods described above.

In one embodiment of the compositions provided above, the composition is formulated for pharmaceutical administration. In a specific embodiment, the composition is formulated for intravenous administration.

DETAILED DESCRIPTION OF INVENTION

I. Introduction

Figures 1A, 1B:
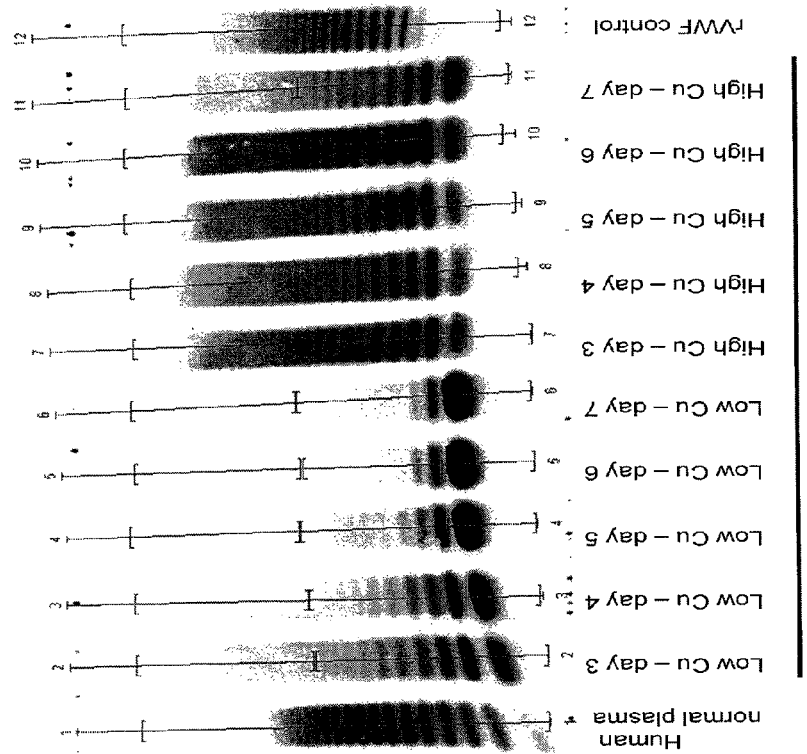
FIG. 1. (1A) Low resolution (1%) agarose gel electrophoresis of rVWF expressed in mammalian cell culture in the presence of low (1.0 µg/L) and high (4.3 µg/L) copper concentration, as described in Example 2. Note that culture Day 3 is equivalent to batch day 1 of Table 7 and Table 8. (1B) The relative amounts of VWF multimers having 1 to 10 dimers (band number 1) and more than 10 dimers (band number 2), as indicated by the bands defined in FIG. 1A, was quantitated by densitometric analysis.

Recombinant vWF (rVWF) and recombinant ADAMTS13 (rA13) can be produced by expression in large-scale mammalian cell cultures. However, the activity of these proteins when produced using standard cell culture conditions often varies across cell cultures, even when the general formulations of the media are not changed, and the specific activities of the recombinant proteins are often not equal to that of vWF and rA13 derived from blood plasma. In addition, rVWF expressed in mammalian cell cultures tends to produce protein compositions with low (under 10%) percentages of higher order multimers (higher order multimers include molecules containing more than 10 VWF dimers). These drawbacks in standard production methods of rVWF and rA13 are particularly problematic when developing cultures for large scale production (i.e., from 10 to over 20,000 liter cultures).

One potential source of the variability often seen in different cell culture batches is the presence of contaminants in components of the cell culture media. These contaminants may be present in different amounts in different batches, leading to variable results in the production of rVWF and rA13. After investigating the different contaminants found in various cell culture media additives, the present inventors found that the presence of hydrolysates leads to variation in copper concentrations in the cell media. Further investigation provided the surprising result that supplementing copper concentrations in cell media to produce a total copper concentration of at least about 1 μg/L to about 20 μg/L consistently increased the total and specific activity of rVWF and rA13 and/or could also lead to increased total protein yield. Thus, the present invention provides methods and compositions for high yield production of rVWF and rA13 proteins with high specific activity.

In one aspect, the present invention provides cell culture methods and compositions for producing large quantities of rVWF and rA13 with activity that is comparable to or higher than that seen with plasma derived vWF (pdVWF) or plasma derived ADAMTS13 (pdA13). In further aspects, the rVWF and rA13 proteins produced in accordance with the present invention show consistently higher activity than proteins produced using standard cell culture methods in media that has not been supplemented with copper or other supplements described in further detail herein. Advantageously, in certain embodiments of the methods and compositions provided herein, the rVWF and rA13 proteins produced in accordance with the present invention show consistently higher specific activity (i.e., U/mg protein) than proteins produced using standard cell culture methods in media that has not been supplemented with copper or other supplements described in further detail herein. Likewise, the methods provided herein for the production of rVWF and rA13 provide higher yields of activity per volume culture (i.e., U/L/D), as compared to standard cell culture methods utilizing media that has not been supplemented with copper or other supplements described in further detail herein.

In a further aspect, the present invention provides cell culture methods in which a basal cell culture medium is supplemented with copper to result in a total concentration of at least about 1 μg/L. In other embodiments, the basal cell culture medium is supplemented with copper to result in a total concentration of at least about 2 μg/L. In yet other embodiments, the basal cell culture medium is supplemented with copper to result in a total concentration of at least about 1 μg/L to about 20 μg/L. In some embodiments, the total concentration of copper is from about 1.5-4.5 μg/L. In certain embodiments, the cell culture medium is supplemented to result in about 1, 1.2, 1.4, 1.6, 1.8, 2.0, 2.2, 2.4, 2.6, 2.8, 3, 3.2, 3.4, 3.6, 3.8, 4, 4.2, 4.4, 4.6, 4.8, 5.0, 5.5, 6.0, 6.5, 7.0, 7.5, 8.0, 8.5, 9.0, 9.5, 10, 11, 12, 13, 14, 15, 16, 17, 18, 19, 20 μg/L copper, or more. Basal cell culture media generally have a trace copper concentration of under 1 μg/L.

In some embodiments, the present invention provides cell culture methods in which a basal cell culture medium is supplemented with from about 1.0 to about 20 μg/L copper for production of rVWF. In further embodiments, the basal cell culture medium is supplemented with from about 1.5-15, 2.0-10, 2.5-8, 3.0-6, 4.0-5.0 μg/L copper for production of rVWF. In still further embodiments, the basal cell culture medium may, in addition to the supplemented copper, also include one or more hydrolysates.

In other embodiments, the present invention provides cell culture methods in which a basal cell culture medium is supplemented with from about 1.5 to about 4 μg/L copper for production of rA13. In further embodiments, the basal cell culture medium is supplemented with from about 1.6-3.8, 1.7-3.6, 1.8-3.4, 1.9-3.2, 2.0-3.0, 2.1-2.8, 2.2-2.6, 2.3-2.4 μg/L copper for production of rA13. In still further embodiments, the basal cell culture medium may, in addition to the supplemented copper, also include one or more hydrolysates. In yet further embodiments, the basal cell culture medium includes, in addition to copper and/or one or more hydrolysates, about 1.0 to about 30 μM zinc. In still further embodiments, the basal cell culture medium further includes, in addition to copper and/or one or more hydrolysates and/or zinc, between about 0.5 to about 5.0 mM calcium.

In a still further aspect and in accordance with any of the above, the present invention provides cell culture methods in which the ammonium levels of the cell culture solution are low (under 10 mM). In certain embodiments, cell culture methods of the present invention utilize cell culture media having over 1, 2, 3, 4, or 5 μg/L copper in combination with low levels of ammonium.

One of the advantages of the methods and compositions of the present invention is that they are amenable to large scale cell culture production. These large scale cell cultures are at least 10 L, 50 L, 100 L, 150 L, 200 L, 250 L, 500 L, 750 L, 1,000 L, 1,500 L, 2,000 L, 5,000 L, 10,000 L, or 20,000 liter cultures.

In certain aspects, the methods of the invention do not necessarily result in a higher amount of recombinant protein overall, but the recombinant protein (either rVWF or rA13) that is produced shows higher total and specific activity than is seen in proteins produced using standard cell cultures, particularly as compared to proteins produced in cell cultures in which the cell culture medium has not been supplemented with additional copper. In further aspects, the rVWF and rA13 proteins produced in cells cultured in copper supplemented media show consistently increased activity per liter of cell culture as compared to cells cultured in basal cell culture media that has not been supplemented with copper. In still further aspects, the copper supplemented media of the present invention result in increased protein yield, increased number of cells in the culture, and/or increased total activity per liter of culture as compared to media that has not been supplemented with copper.

Still further advantages of methods and compositions of the invention is that they result a population of proteins containing a high percentage (over 10%) of highly multimerized rVWF.

Although much of the discussion herein regarding ADAMTS proteins is in terms of ADAMTS13 (A13), it will be appreciated that because all ADAMTS proteins share a common core domain architecture and common structure-function relationships, the methods and compositions described herein are applicable for production of any ADAMTS proteins, not only rA13.

II. Definitions

As used herein, "recombinant vWF" includes vWF obtained via recombinant DNA technology. In certain embodiments, vWF proteins of the invention can comprise a construct, for example, prepared as in WO 1986/06096 published on Oct. 23, 1986 and U.S. patent application Ser. No. 07/559,509, filed on Jul. 23, 1990, in the name of Ginsburg et al., which is incorporated herein by reference with respect to the methods of producing recombinant vWF. The vWF in the present invention can include all potential forms, including the monomeric and multimeric forms. It should also be understood that the present invention encompasses different forms of vWF to be used in combination. For example, the vWF of the present invention may include different multimers, different derivatives and both biologically active derivatives and derivatives not biologically active.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

In the context of the present invention, the recombinant vWF embraces any member of the vWF family from, for example, a mammal such as a primate, human, monkey, rabbit, pig, rodent, mouse, rat, hamster, gerbil, canine, feline, and biologically active derivatives thereof. In a preferred embodiment, the recombinant VWF is human VWF. Mutant and variant vWF proteins having activity are also embraced, as are functional fragments and fusion proteins of the vWF proteins. Furthermore, the vWF of the invention may further comprise tags that facilitate purification, detection, or both. The vWF described herein may further be modified with a therapeutic moiety or a moiety suitable imaging in vitro or in vivo.

The terms "highly multimeric vWF," "high molecular weight vWF," and "HMW VWF" may be used interchangeably and refer to covalently attached vWF multimers containing more than 10 VWF dimers. In certain embodiments, HMW VWF contains at least 11 VWF dimers, or at least 12, 13, 14, 15, 16, 17, 18, 19, 20, 21, 22, or more VWF dimers.

As used herein, an "ADAMTS protein" refers to a polypeptide of the disintegrin and metalloproteinase with thrombospondin type I motifs family of metalloproteinases. Members of this family include the human proteins ADAMTS1 (NM_006988), ADAMTS2 (NM_014244; NM_021599), ADAMTS3 (NM_014243), ADAMTS4 (NM_005099), ADAMTS5 (NM_007038), ADAMTS6 (NM_014273), ADAMTS7 (NM_0142727), ADAMTS8 (NM_007037), ADAMTS9 (NM_182920; NM_182921; NM_020249), ADAMTS10 (NM_030957), ADAMTS12 (NM_030955), ADAMTS13 (NM_139025; NM_139026; NM_139027; NM_139028), ADAMTS14 (NM_139155; NM_080722), ADAMTS15 (NM_139055), ADAMTS16 (NM_139056), ADAMTS17 (NM_139057), ADAMTS18 (NM_199355; NM_139054), ADAMTS19 (NM_133638), and ADAMTS20 (NM_025003, NM_175851). ADAMTS proteins include both full-length proteins and partial polypeptides that display at least partial biological activity, for example, at least 10%, 20%, 30%, 40%, 50%, 60%, 70%, 80%, 90%, or more of the activity demonstrated by the full-length protein, in particular the protease activity demonstrated by the full length protein. In certain instances, an ADAMTS protein will be post-translationally modified either in vivo or in vitro, for example, by enzymatic or chemical means. It is understood that the ADAMTS proteins of the present invention include alternatively spliced isoforms, conservatively modified proteins, substantially identical proteins, homologues, and the like.

In the context of the present invention, an ADAMTS protein embraces any member of the ADAMTS family from, for example, a mammal such as a primate, human, monkey, rabbit, pig, rodent, mouse, rat, hamster, gerbil, canine, feline, and biologically active derivatives thereof. Mutant and variant ADAMTS proteins having activity are also embraced, as are functional fragments and fusion proteins of the ADAMTS proteins. Furthermore, the ADAMTS proteins of the invention may further comprise tags that facilitate purification, detection, or both. The ADAMTS proteins described herein may further be modified with a therapeutic moiety or a moiety suitable imaging in vitro or in vivo.

As used herein, an "ADAMTS13 protein" refers to any protein or polypeptide with ADAMTS13 activity, particularly the ability to cleave the peptide bond between residues Tyr-842 and Met-843 of VWF. In an exemplary embodiment, an ADAMTS13 protein refers to a polypeptide comprising an amino acid sequence that is highly similar to that of $NP_{13}$ 620594 (ADAMTS13 isoform 1, preproprotein) or amino acids 75 to 1427 of $NP_{13}$ 620594 (ADAMTS13 isoform 1, mature polypeptide). In another embodiment, an ADAMTS13 protein refers to a polypeptide comprising an amino acid sequence that is highly similar to that of $NP_{13}$ 620596 (ADAMTS13 isoform 2, preproprotein) or amino acids 75 to 1371 of $NP_{13}$ 620594 (ADAMTS13 isoform 2, mature polypeptide). In yet another embodiment, ADAMTS13 proteins include polypeptides comprising an amino acid sequence highly similar to that of $NP_{13}$ 620595 (ADAMTS13 isoform 3, preproprotein) or amino acids 75 to 1340 of $NP_{13}$ 620595 (ADAMTS13 isoform 1, mature polypeptide). As used herein, an ADAMTS13 protein includes natural variants with vWF cleaving activity and artificial constructs with vWF cleaving activity. As used in the present invention, ADAMTS13 encompasses any natural variants, alternative sequences, isoforms or mutant proteins that retain some basal activity. Examples of ADAMTS13 mutations found in the human population include, without limitation, R7W, V88M, H96D, R102C, R193W, T196I, H234Q, A250V, R268P, W390C, R398H, Q448E, Q456H, P457L, C508Y, R528G, P618A, R625H, 1673F, R692c, A732V, S903L, C908Y, C951G, G982R, C1024G, A1033T, R1095W, R1123c, C1213Y, T1226I, G1239V, R1336W, many of which have been found associated with thrombotic thrombocytopenic purpura (TTP). ADAMTS13 proteins also includes polypeptides containing post-translational modifications. For example, ADAMTS13 has been shown to be modified by N-acetylglucosamine (GlcNAc) at residues 614, 667, and 1354, and it has been predicted that residues 142, 146, 552, 579, 707, 828, and 1235 may also be modified in this fashion.

Proteolytically active recombinant ADAMTS13 may be prepared by expression in mammalian cell cultures, as described in Plaimauer et al., (2002, Blood. 15; 100(10): 3626-32) and US 2005/0266528, the disclosures of which are herein incorporated by reference in their entireties for all purposes. Methods for the expression of recombinant ADAMTS13 in cell culture are disclosed in Plaimauer B, Scheiflinger F. (Semin Hematol. 2004 January; 41(1):24-33 and US 2011/0086413, the disclosures of which are herein incorporated by reference in their entireties for all purposes.

As used herein, the term "biologically active derivative", when used in the context of an ADAMTS protein, also embraces polypeptides obtained via recombinant DNA technology. This may include any method known in the art for (i)

the production of recombinant DNA by genetic engineering, e.g., via reverse transcription of RNA and/or amplification of DNA, (ii) introducing recombinant DNA into prokaryotic or eukaryotic cells by transfection, i.e., via electroporation or microinjection, (iii) cultivating said transformed cells, e.g., in a continuous or batch-wise manner, (iv) expressing an ADAMTS protein, e.g., constitutively or upon induction, and (v) isolating said ADAMTS protein, e.g., from the culture medium or by harvesting the transformed cells, in order to (vi) obtain substantially purified recombinant ADAMTS protein, e.g., via ion exchange chromatography, size exclusion chromatography, affinity chromatography, hydrophobic interaction chromatography, and the like. The term "biologically active derivative" includes also chimeric molecules such as e.g. an ADAMTS protein, or functional fragment thereof, in combination with a second polypeptide, e.g., an immunoglobulin Fc domain or an albumin domain, in order to improve the biological/pharmacological properties such as e.g., half life of the ADAMTS protein in the circulation system of a mammal, particularly a human.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. In one embodiment, rVWF is the predominant species present in a preparation is substantially purified. In another embodiment, rA13 is the predominant species present in a preparation is substantially purified. The term "purified" in some embodiments denotes that a nucleic acid or protein gives rise to essentially one band in an electrophoretic gel. In other embodiments, it means that the nucleic acid or protein is at least 50% pure, more preferably at least 60%, 65%, 70%, 75%, 80%, 85%, 90%, 95%, 96%, 97%, 98%, 99% or more pure. "Purify" or "purification" in other embodiments means removing at least one contaminant from the composition to be purified. In this sense, purification does not require that the purified compound be homogenous, e.g., 100% pure.

The biological activity of vWF can be measured by known in vitro assays. For example, the Ristocetin Cofactor assay is based on the agglutination of fresh or formalin-fixed platelets induced by the antibiotic ristocetin in the presence of vWF. The degree of platelet agglutination depends on the vWF concentration and can be measured by the turbidimetric method, e.g. by use of an aggregometer (Weiss et al., J. Clin. Invest. 52: 2708-2716, 1973; Macfarlane et al., Thromb. Diath. Haemorrh. 34: 306-308, 1975). As provided herein, the specific Ristocetin Cofactor activity of the vWF of the present invention is described in terms of mU/µg of vWF, as measured using in vitro assays.

As used herein, "one unit of ADAMTS activity" is defined as the amount of activity in 1 mL of pooled normal human plasma, regardless of the assay being used. For example, when the ADAMTS protein is ADAMTS13, one unit of ADAMTS13 FRETS-VWF73 activity is the amount of activity needed to cleave the same amount of FRETS-VWF73 substrate (Kokame et al., Br J Haematol. 2005 April; 129(1): 93-100) as is cleaved by one mL of pooled normal human plasma. Conveniently, ADAMTS13 activity may be determined by functional assays, such as functional assays employing modified von Willebrand factor peptides as substrate for ADAMTS13 (Tripodi et al. *J Thromb Haemost.* 2008 September; 6(9): 1534-41). A preferred method of determining recombinant human ADAMTS13 activity is disclosed in Gerritsen et al. (Assay of von Willebrand factor (vWF)-cleaving protease based on decreased collagen binding affinity of degraded vWF: a tool for the diagnosis of thrombotic thrombocytopenic purpura (TTP). Thromb Haemost 1999; 82: 1386-1389). In one embodiment, to be considered as a ADAMTS13 protein as defined above, a polypeptide or protein must have at least 1% of the vWF cleaving activity of native ADAMTS13. In other embodiments, an ADAMTS13 protein will contain at least 10% of the activity of native ADAMTS13. In yet other embodiments, an ADAMTS13 protein will contain at least 5%, 10%, 20%, 30%, 40%, 50%, 60%, 70%, 80%, 90%, or 100% of the activity of native ADAMTS13. The quantity of an ADAMTS13 protein may also be determined by measurement of an ADAMTS13 antigen, for example using the ELISA method disclosed in Rieger et al., (2006, *Thromb Haemost.* 2006 95(2):212-20). A well established convention in the art is that 1 mL of pooled normal human plasma contains 1 µg of ADAMTS13. Thus, the convention in the art is that 1 µg of plasma-derived ADAMTS13 has one unit of ADAMTS13 activity.

The terms "cell culture solution," "cell culture medium or media," and "cell culture supernatant" refer to aspects of cell culture processes generally well known in the art. In the context of the present invention, a cell culture solution can include cell culture media and cell culture supernatant. The cell culture media are externally added to the cell culture solution, optionally together with supplements, to provide nutrients and other components for culturing cells expressing rVWF or rA13. The cell culture supernatant refers to a cell culture solution comprising the nutrients and other components from the cell culture medium as well as products released, metabolized, and/or excreted from the cells during culture, but not the cells themselves. Thus in one context, a cell culture supernatant can refer to the liquid phase of a cell culture solution (i.e., the cell culture solution excluding the cells). For example, the ammonium concentration of a culture supernatant generally refers to the ammonium concentration present in the cell culture solution. In other contexts, a cell culture supernatant refers to a cell culture solution from which the cells have been removed (i.e., a recovered cell culture supernatant).

As used herein, the terms "vitamin B3," "nicotinamide," "niacinamide," "niacin," and "nicotinic acid" may be used interchangeably to refer to any member of the B3 family of vitamins. Accordingly, any member of this family may be used to supplement medium used in the methods of the present invention.

As used herein, the term "chemically defined medium" or "chemically defined media" refers to a synthetic growth medium in which the identity and concentration of all the components are known. Chemically defined mediums do not contain bacterial, yeast, animal, or plant extracts, although they may or may not include individual plant or animal-derived components (e.g., proteins, polypeptides, etc.). Non-limiting examples of commercially available chemically defined mediums include, various Dulbecco's Modified Eagle's (DME) mediums (Sigma-Aldrich Co; SAFC Biosciences, Inc), Ham's Nutrient Mixture (Sigma-Aldrich Co; SAFC Biosciences, Inc), combinations thereof, and the like. Methods of preparing chemically defined culture mediums are known in the art, for example in U.S. Pat. Nos. 6,171,825 and 6,936,441, WO 2007/077217, and U.S. Patent Application Publication Numbers 2008/0009040 and 2007/0212770, the disclosures of which are incorporated herein by reference in their entireties for all purposes.

As used herein, the term "oligopeptide-free culture medium" or "oligopeptide-free culture media" refers to a protein-free medium that does not comprise oligopeptides, such as, e.g., oligopeptides derived from a protein hydrolysate. In one embodiment, the medium does not comprise oligopeptides having twenty or more amino acids. In one embodiment of the present invention, the medium does not comprise oligopeptides having fifteen or more amino acids. In another embodiment of the invention, the medium does not comprise oligopeptides having ten or more amino acids. In one embodiment the medium does not comprise oligopeptides having seven or more amino acids. In another embodiment the medium does not comprise oligopeptides having five or more amino acids. In still another embodiment the medium does not comprise oligopeptides having three or more amino acids. According to a further embodiment of the present invention, the medium does not comprise oligopeptides having two or more amino acids. Methods of preparing oligopeptide-free culture medium are known in the art, for example in U.S. Pat. Nos. 6,171,825 and 6,936,441, WO 2007/077217, and U.S. Patent Application Publication Numbers 2008/0009040 and 2007/0212770, the disclosures of which are incorporated herein by reference in their entireties for all purposes.

As used herein, the term "serum-free culture medium" or "serum-free culture media" refers to a culture medium that is not supplemented with an animal serum. Although oftentimes serum-free mediums are chemically defined mediums, serum-free mediums may be supplemented with discrete animal or plant proteins or protein fractions. Methods of preparing serum-free culture medium are known in the art, for example in U.S. Pat. Nos. 6,171,825 and 6,936,441, WO 2007/077217, and U.S. Patent Application Publication Numbers 2008/0009040 and 2007/0212770, the disclosures of which are incorporated herein by reference in their entireties for all purposes.

As used herein, the term "animal protein-free culture medium" or "animal protein-free culture media" refers to a culture medium that is not supplemented with an animal serum, protein, or protein fraction. Although oftentimes animal protein-free culture mediums are chemically defined mediums, animal protein-free culture mediums may contain plant or yeast hydrolysates. Methods of preparing animal protein-free culture medium are known in the art, for example in U.S. Pat. Nos. 6,171,825 and 6,936,441, WO 2007/077217, and U.S. Patent Application Publication Numbers 2008/0009040 and 2007/0212770, the disclosures of which are incorporated herein by reference in their entireties for all purposes.

As used herein, the term "basal cell culture medium" or "basal cell culture media" refers to a chemically defined culture medium, an oligopeptide-free culture medium, a serum-free culture medium, or an animal protein-free culture medium that has not been supplemented with a hydrolysate, e.g., a plant or yeast hydrolysate. basal mediums are well known in the art, e.g., DMEM, Ham's F12, DMEM/Ham's F12, Medium 199, McCoy, or RPMI. The basal medium can include a number of ingredients, including amino acids, vitamins, organic and inorganic salts, and sources of carbohydrate. Each ingredient can be present in an amount that supports the cultivation of a cell, such amounts being generally known to a person skilled in the art. The medium can include auxiliary substances, such as buffer substances, e.g., sodium bicarbonate, antioxidants, stabilizers to counteract mechanical stress, or protease inhibitors. If necessary, a non-ionic surfactant such as copolymers and/or mixtures of polyethylene glycols and polypropylene glycols can be added.

III. Cell Culture Media and Cell Culture Supernatant

One aspect of the present invention relates to cell culture media for producing rVWF and/or rA13 that have increased activity as compared to rVWF and rA13 produced with basal cell culture media. In one aspect, the present invention relates to cell culture media for producing rVWF and/or rA13 in which basal cell culture media is supplemented with one or more additional substances. In specific embodiments and as is discussed in further detail below, cell culture conditions of the present invention include basal cell culture media supplemented to have at least 1.0 µg/L copper. In further embodiments, cell culture media of use and supernatants derived from the processes in the present invention also comprise low levels (under 10 mM) of ammonium. In a particular embodiment, the cell culture conditions used for expressing rVWF and/or rA13 are controlled such that the cell culture supernatant maintains a low level of ammonium, i.e., less than 10 mM and preferably less than 5 mM.

The culture media of the present invention can be based on a suitable basal medium well known in the art, e.g., DMEM, Ham's F12, DMEM/Ham's F12, Medium 199, McCoy, or RPMI. The basal medium can include a number of ingredients, including amino acids, vitamins, organic and inorganic salts, and sources of carbohydrate. Each ingredient can be present in an amount that supports the cultivation of a cell, such amounts being generally known to a person skilled in the art. The medium can include auxiliary substances, such as buffer substances, e.g., sodium bicarbonate, antioxidants, stabilizers to counteract mechanical stress, or protease inhibitors. If necessary, a non-ionic surfactant such as copolymers and/or mixtures of polyethylene glycols and polypropylene glycols can be added.

Generally, basal media contain less than 1 µg/L of copper—for example, DMEM/Ham's F12 has a copper concentration of about 0.3 µg/L. Such concentrations of copper do not provide enough copper ions to support production of rVWF and rA13 proteins of the present invention, which show high specific activity.

Copper can be provided to cell culture media of the present invention through a variety of ways, such as through addition of a medium supplement. In some embodiments, the medium supplement can contain hydrolysate, which can be provided to increase the copper concentration in the media. Hydrolysates can include any hydrolysate well known in the art, such as plant hydrolysates, soy hydrolysates, and wheat gluten hydrolysate. In certain embodiments, addition of hydrolysate can contribute an increased copper concentration of about 0.2 to about 10 µg/L of $Cu^{2+}$. In some embodiments, the amount of copper provided by the hydrolysate can depend on the amount of copper in the hydrolysate as well as the amount of hydrolysate added. The copper content of a hydrolysate can be determined by elemental analysis, e.g., atom adsorption spectroscopy (GFAA: graphite furnace atomic adsorption), or mass spectroscopy methods (e.g., ICP-MS).

In certain embodiments, copper can be provided to the culture media alone or in addition to hydrolysate by providing a medium supplement including a suitable copper salt or copper chelate. Suitable copper salts can include but are not limited to copper sulfate, copper acetate, copper carbonate, copper chloride, copper hydroxide, copper nitrate, and copper oxide. Suitable copper chelators can include but are not limited to albumin, ethylenediaminetetraacetic acid (EDTA), polyamine chelating agents, ethylenediamine, diethylenetriamine, triethylenetetramine, triethylenediamine, tetraethylenepentamine, aminoethylethanolamine, aminoethylpiperazine, pentaethylenehexamine, triethylenetetramine-hydrochloride, tetraethylenepentamine-hydrochloride, pentaethylenehexamine-hydrochloride, tetraethylpentamine, captopril, penicilamine, N,N'-bis(3-aminopropyl)-1,3-propanediamine, N,N,Bis (2 animoethyl) 1,3 propane diamine, 1,7-dioxa-4,10-diazacyclododecane, 1,4,8,11-tetraaza cyclotetradecane-5,7-dione, 1,4,7-triazacyclononane trihydrochloride, 1-oxa-4,7,10-triazacyclododecane, 1,4,8,12-tetraaza cyclopentadecane, and 1,4,7,10-tetraaza cyclododecane.

In certain embodiments, basal cell culture media is supplemented with copper to result in a total copper concentration of about 1.0 to about 20 μg/L. In a specific embodiment, the basal cell media is supplemented with copper to a final concentration of between about 1.0 to about 10 μg/L. In further embodiments, the basal cell culture media is supplemented to result in a final copper concentration of about 1.0-5.0, 1.2-4.0, 1.3-3.0, 1.4-2.9, 1.5-2.8, 1.6-2.7, 1.7-2.6, 1.8-2.5, 1.9-2.4, 2.0-2.3, 2.1-2.2 μg/L copper. In further embodiments, the basal cell culture media used in methods of the present invention are supplemented to result in about 1.2-9.5, 1.4-9, 1.6-8.5, 1.8-8, 2.0-7.5, 2.2-7, 2.4-6.5, 2.6-6.0, 2.8-5.5, 3.0-5.0, 3.2-4.5, 3.4-4, and 2-4 μg/L copper. In yet other embodiments, the basal cell culture media used in methods of the present invention are supplemented to result in about 1-6, 2-5, 3-4 μg/L copper. In one embodiment, the basal cell culture media is supplemented with copper to result in a total copper concentration of at least 1 μg/L. In another embodiment, the basal cell culture media is supplemented with copper to result in a total copper concentration of at least 2 μg/L. In yet another embodiment, the basal cell culture media is supplemented with copper to result in a total copper concentration of at least 4 μg/L. In certain embodiments, the basal cell culture media is supplemented with copper to result in a total copper concentration of at least 1 μg/L, or at least 2, 3, 4, 5, 6, 7, 8, 9, 10, 11, 12, 13, 14, 15, 16, 17, 18, 19, 20 μg/L copper, or more. In certain embodiments and as discussed in further detail herein, cultures for producing rA13 may contain from about 2-4 μg/L of copper, whereas cultures for producing rVWF may contain at least 2 μg/L of copper.

The concentrations indicated above are the respective concentrations of pure copper, in cupric form ($Cu^{2+}$). If a copper derivative, e.g., a hydrated salt, or a compound comprising copper, e.g., a copper chelator, is used, the amount of derivative or chelator is added such that the final concentration of the copper is in the ranges described herein. For example, 2 μg/L of $CuSO_4.5H_2O$ is equivalent to a copper concentration of about 0.51 μg/L (without sulfate and $5H_2O$).

Advantageously, it has been found that the use of cell culture medium in cell culture processes resulting in low ammonium ($NH_4^+$) concentrations in the cell culture solution (i.e., in the culture supernatant) results in the expression of recombinant VWF and/or rA13 with higher specific activities. Accordingly, in certain embodiments, the $NH_4^+$ concentration of the supernatant is no higher than 10 mM. In a preferred embodiment, the $NH_4^+$ concentration of the supernatant is no higher than 5 mM. In a preferred embodiment, the $NH_4^+$ concentration of the supernatant is no higher than 4 mM. In yet other embodiments, the $NH_4^+$ concentration of the supernatant is no higher than 10 mM, 9 mM, 8 mM, 7 mM, 6 mM, 5 mM, 4 mM, 3 mM, 2 mM, 1 mM, or less.

Accordingly, in certain embodiments, the methods and compositions provided herein rely on the use of basal cell culture media supplemented with copper (e.g., to a final concentration of at least 2 μg/L) used in a process that results in an $NH_4^+$ concentration of no higher than 10 mM in the supernatant. In yet other embodiments, the basal cell culture medium is supplemented to provide a final copper and ammonium concentration according to any one of variations 1 to 440, as provided in Table 1.

TABLE 1

Exemplary embodiments of copper and ammonium concentrations present in culture media and supernatant useful for the expression of a recombinant proteins as provided herein.

| | | | Ammonium Concentration | | | | | | | | | |
|---|---|---|---|---|---|---|---|---|---|---|---|---|
| | | N.D. | NMT 10 mM | NMT 9 mM | NMT 8 mM | NMT 7 mM | NMT 6 mM | NMT 5 mM | NMT 4 mM | NMT 3 mM | NMT 2 mM | NMT 1 mM |
| Copper Concentration | AL 1 μg/L | Var. 1 | Var. 41 | Var. 81 | Var. 121 | Var. 161 | Var. 201 | Var. 241 | Var. 281 | Var. 321 | Var. 361 | Var. 401 |
| | AL 2 μg/L | Var. 2 | Var. 42 | Var. 82 | Var. 122 | Var. 162 | Var. 202 | Var. 242 | Var. 282 | Var. 322 | Var. 362 | Var. 402 |
| | AL 3 μg/L | Var. 3 | Var. 43 | Var. 83 | Var. 123 | Var. 163 | Var. 203 | Var. 243 | Var. 283 | Var. 323 | Var. 363 | Var. 403 |
| | AL 4 μg/L | Var. 4 | Var. 44 | Var. 84 | Var. 124 | Var. 164 | Var. 204 | Var. 244 | Var. 284 | Var. 324 | Var. 364 | Var. 404 |
| | AL 5 μg/L | Var. 5 | Var. 45 | Var. 85 | Var. 125 | Var. 165 | Var. 205 | Var. 245 | Var. 285 | Var. 325 | Var. 365 | Var. 405 |
| | AL 6 μg/L | Var. 6 | Var. 46 | Var. 86 | Var. 126 | Var. 166 | Var. 206 | Var. 246 | Var. 286 | Var. 326 | Var. 366 | Var. 406 |
| | AL 7 μg/L | Var. 7 | Var. 47 | Var. 87 | Var. 127 | Var. 167 | Var. 207 | Var. 247 | Var. 287 | Var. 327 | Var. 367 | Var. 407 |
| | AL 8 μg/L | Var. 8 | Var. 48 | Var. 88 | Var. 128 | Var. 168 | Var. 208 | Var. 248 | Var. 288 | Var. 328 | Var. 368 | Var. 408 |
| | AL 9 μg/L | Var. 9 | Var. 49 | Var. 89 | Var. 129 | Var. 169 | Var. 209 | Var. 249 | Var. 289 | Var. 329 | Var. 369 | Var. 409 |
| | AL 10 μg/L | Var. 10 | Var. 50 | Var. 90 | Var. 130 | Var. 170 | Var. 210 | Var. 250 | Var. 290 | Var. 330 | Var. 370 | Var. 410 |
| | About 1 μg/L | Var. 11 | Var. 51 | Var. 91 | Var. 131 | Var. 171 | Var. 211 | Var. 251 | Var. 291 | Var. 331 | Var. 371 | Var. 411 |
| | About 1.5 μg/L | Var. 12 | Var. 52 | Var. 92 | Var. 132 | Var. 172 | Var. 212 | Var. 252 | Var. 292 | Var. 332 | Var. 372 | Var. 412 |
| | About 2 μg/L | Var. 13 | Var. 53 | Var. 93 | Var. 133 | Var. 173 | Var. 213 | Var. 253 | Var. 293 | Var. 333 | Var. 373 | Var. 413 |
| | About 2.5 μg/L | Var. 14 | Var. 54 | Var. 94 | Var. 134 | Var. 174 | Var. 214 | Var. 254 | Var. 294 | Var. 334 | Var. 374 | Var. 414 |
| | About 3 μg/L | Var. 15 | Var. 55 | Var. 95 | Var. 135 | Var. 175 | Var. 215 | Var. 255 | Var. 295 | Var. 335 | Var. 375 | Var. 415 |

TABLE 1-continued

Exemplary embodiments of copper and ammonium concentrations present in culture
media and supernatant useful for the expression of a recombinant proteins as provided herein.

|  | | Ammonium Concentration | | | | | | | | | |
|---|---|---|---|---|---|---|---|---|---|---|---|
|  | N.D. | NMT 10 mM | NMT 9 mM | NMT 8 mM | NMT 7 mM | NMT 6 mM | NMT 5 mM | NMT 4 mM | NMT 3 mM | NMT 2 mM | NMT 1 mM |
| About 3.5 μg/L | Var. 16 | Var. 56 | Var. 96 | Var. 136 | Var. 176 | Var. 216 | Var. 256 | Var. 296 | Var. 336 | Var. 376 | Var. 416 |
| About 4 μg/L | Var. 17 | Var. 57 | Var. 97 | Var. 137 | Var. 177 | Var. 217 | Var. 257 | Var. 297 | Var. 337 | Var. 377 | Var. 417 |
| About 4.5 μg/L | Var. 18 | Var. 58 | Var. 98 | Var. 138 | Var. 178 | Var. 218 | Var. 258 | Var. 298 | Var. 338 | Var. 378 | Var. 418 |
| About 5 μg/L | Var. 19 | Var. 59 | Var. 99 | Var. 139 | Var. 179 | Var. 219 | Var. 259 | Var. 299 | Var. 339 | Var. 379 | Var. 419 |
| About 5.5 μg/L | Var. 20 | Var. 60 | Var. 100 | Var. 140 | Var. 180 | Var. 220 | Var. 260 | Var. 300 | Var. 340 | Var. 380 | Var. 420 |
| About 6 μg/L | Var. 21 | Var. 61 | Var. 101 | Var. 141 | Var. 181 | Var. 221 | Var. 261 | Var. 301 | Var. 341 | Var. 381 | Var. 421 |
| About 7 μg/L | Var. 22 | Var. 62 | Var. 102 | Var. 142 | Var. 182 | Var. 222 | Var. 262 | Var. 302 | Var. 342 | Var. 382 | Var. 422 |
| About 8 μg/L | Var. 23 | Var. 63 | Var. 103 | Var. 143 | Var. 183 | Var. 223 | Var. 263 | Var. 303 | Var. 343 | Var. 383 | Var. 423 |
| About 9 μg/L | Var. 24 | Var. 64 | Var. 104 | Var. 144 | Var. 184 | Var. 224 | Var. 264 | Var. 304 | Var. 344 | Var. 384 | Var. 424 |
| About 10 μg/L | Var. 25 | Var. 65 | Var. 105 | Var. 145 | Var. 185 | Var. 225 | Var. 265 | Var. 305 | Var. 345 | Var. 385 | Var. 425 |
| 1-20 μg/L | Var. 26 | Var. 66 | Var. 106 | Var. 146 | Var. 186 | Var. 226 | Var. 266 | Var. 306 | Var. 346 | Var. 386 | Var. 426 |
| 2-20 μg/L | Var. 27 | Var. 67 | Var. 107 | Var. 147 | Var. 187 | Var. 227 | Var. 267 | Var. 307 | Var. 347 | Var. 387 | Var. 427 |
| 1-10 μg/L | Var. 28 | Var. 68 | Var. 108 | Var. 148 | Var. 188 | Var. 228 | Var. 268 | Var. 308 | Var. 348 | Var. 388 | Var. 428 |
| 2-10 μg/L | Var. 29 | Var. 69 | Var. 109 | Var. 149 | Var. 189 | Var. 229 | Var. 269 | Var. 309 | Var. 349 | Var. 389 | Var. 429 |
| 1-6 μg/L | Var. 30 | Var. 70 | Var. 110 | Var. 150 | Var. 190 | Var. 230 | Var. 270 | Var. 310 | Var. 350 | Var. 390 | Var. 430 |
| 2-6 μg/L | Var. 31 | Var. 71 | Var. 111 | Var. 151 | Var. 191 | Var. 231 | Var. 271 | Var. 311 | Var. 351 | Var. 391 | Var. 431 |
| 3-6 μg/L | Var. 32 | Var. 72 | Var. 112 | Var. 152 | Var. 192 | Var. 232 | Var. 272 | Var. 312 | Var. 352 | Var. 392 | Var. 432 |
| 4-6 μg/L | Var. 33 | Var. 73 | Var. 113 | Var. 153 | Var. 193 | Var. 233 | Var. 273 | Var. 313 | Var. 353 | Var. 393 | Var. 433 |
| 1-5 μg/L | Var. 34 | Var. 74 | Var. 114 | Var. 154 | Var. 194 | Var. 234 | Var. 274 | Var. 314 | Var. 354 | Var. 394 | Var. 434 |
| 2-5 μg/L | Var. 35 | Var. 75 | Var. 115 | Var. 155 | Var. 195 | Var. 235 | Var. 275 | Var. 315 | Var. 355 | Var. 395 | Var. 435 |
| 3-5 μg/L | Var. 36 | Var. 76 | Var. 116 | Var. 156 | Var. 196 | Var. 236 | Var. 276 | Var. 316 | Var. 356 | Var. 396 | Var. 436 |
| 4-5 μg/L | Var. 37 | Var. 77 | Var. 117 | Var. 157 | Var. 197 | Var. 237 | Var. 277 | Var. 317 | Var. 357 | Var. 397 | Var. 437 |
| 1-4 μg/L | Var. 38 | Var. 78 | Var. 118 | Var. 158 | Var. 198 | Var. 238 | Var. 278 | Var. 318 | Var. 358 | Var. 398 | Var. 438 |
| 2-4 μg/L | Var. 39 | Var. 79 | Var. 119 | Var. 159 | Var. 199 | Var. 239 | Var. 279 | Var. 319 | Var. 359 | Var. 399 | Var. 439 |
| 3-4 μg/L | Var. 40 | Var. 80 | Var. 120 | Var. 160 | Var. 200 | Var. 240 | Var. 280 | Var. 320 | Var. 360 | Var. 400 | Var. 440 |

ND = not defined
NMT = no more than
AL = at least

In some embodiments, the copper supplemented media of the present invention are produced by supplementing basal media that is animal protein-free and/or chemically defined. Methods of preparing animal protein-free and chemically defined culture mediums are known in the art, for example in U.S. Pat. Nos. 6,171,825 and 6,936,441, WO 2007/077217, and U.S. Patent Application Publication Numbers 2008/0009040 and 2007/0212770, the disclosures of which are incorporated herein by reference in their entireties for all purposes. In one embodiment, the basal culture medium used in the methods described herein is animal protein-free or oligopeptide-free medium. In certain embodiments, the culture medium may be chemically defined. In certain embodiments, the culture media may contain at least one polyamine at a concentration of about 0.5 mg/L to about 10 mg/L.

In further embodiments and in addition to any of the description provided above, culture media of the invention are provided in which a basal medium is supplemented with copper and at least one of calcium, zinc, and/or vitamin B3. In certain embodiments, the medium may be an animal protein-free, oligopeptide-free, or chemically defined medium. In certain embodiments, the animal protein-free or oligopeptide free medium is prepared as taught in U.S. Pat. Nos. 6,171,825 and 6,936,441, WO 2007/077217, and U.S. Patent Application Publication Numbers 2008/0009040 and 2007/0212770, the disclosures of which are incorporated herein by reference in their entireties for all purposes, both of which are incorporated herein by reference in their entireties for all purposes, and supplemented with additional copper and optionally one or more of calcium, zinc, and vitamin B3. In a specific embodiment, the chemically defined culture medium may be similar to a Dulbecco's Modified Eagle's Media/Ham's F12 1:1 mixture (DMEM/Ham's F12), which has been supplemented with additional copper and optionally calcium, zinc, and/or vitamin B3, in order to increase the specific activity of rVWF or rA13 expressed in a cell cultured in the medium. In yet other embodiments, the culture medium is animal component free. In another embodiment, the culture medium contains protein, e.g., animal protein from serum such as fetal calf serum. In another embodiment, the culture has recombinant proteins exogenously added. In another embodiment, the proteins are from a certified pathogen free animal.

In certain embodiments, the culture media contains at least one polyamine at a concentration of at or about between 0.5 mg/L and 30 mg/L. In another embodiment, the culture medium contains at least one polyamine at or about between 0.5 mg/L and 10 mg/L. In one embodiment, the culture medium contains at least one polyamine at or about between 2 mg/L and 8 mg/L. In certain embodiments the polyamine is from the group of ornithine, putrescine, spermine or spermidine, or the like. In a preferred embodiment, the polyamine is putrescine. In a specific embodiment, the culture medium contains at or about between 2 mg/L and 8 mg/L putrescine.

In one embodiment, the culture media contains at least one polyamine at a concentration of at or about between 0.5 mg/L and 30 mg/L and a copper and ammonium combination according to any one of variations 1 to 440, as set forth in Table 1. In another embodiment, the culture medium contains at least one polyamine at or about between 0.5 mg/L and 10 mg/L and a copper and ammonium combination according to any one of variations 1 to 440, as set forth in Table 1. In one embodiment, the culture medium contains at least one polyamine at or about between 2 mg/L and 8 mg/L and a copper and ammonium combination according to any one of variations 1 to 440, as set forth in Table 1. In certain embodiments the polyamine is from the group of ornithine, putrescine, spermine or spermidine, or the like. In a preferred embodiment, the polyamine is putrescine. In a specific embodiment, the culture medium contains at or about between 2 mg/L and 8 mg/L putrescine and a copper and ammonium combination according to any one of variations 1 to 440, as set forth in Table 1.

In further aspects, in addition to copper, cell culture media of use in the present invention may further include one or more of: additional calcium, zinc, one or more vitamins, and any combination thereof.

Generally, any calcium salt may be used to supplement the media of the invention, non-limiting examples of acceptable salts include $CaCl_2$, $CaCl_2$, $CaFPO_3.2H_2O$, $CaI_2$, $CaBr_2$, $(C_2H_3O_2)_2Ca$, $(CHO_2)_2Ca$, $(C_6H_7O_6)_2Ca$, $(C_6H_5O_7)_2Ca_3.2H_2O$, and the like. In certain embodiments, a pharmaceutically acceptable salt of calcium is used to supplement the culture mediums of the invention.

Generally, any zinc salt may be used to supplement the media of the invention, non-limiting examples of acceptable salts include, $ZnSO_4.7H_2O$, $ZnSO_3.2H_2O$, $(C_6H_5O_7)_2Zn_3.2H_2O$, $ZnBr_2$, $ZnBr_2.2H_2O$, $ZnCl_2$, $Zn(NO_3)_2.6H_2O$, $Zn(H_2PO_4)_2.H_2O$, $(C_2H_3O_2)_2Zn.2H_2O$, and the like. In certain embodiments, a pharmaceutically acceptable salt of zinc is used to supplement the culture mediums of the invention. In other embodiments, a zinc containing peptide or protein preparation, for example insulin, may be used to the supplement the culture provided herein.

In still further aspects, basal cell media supplemented with copper and one or more of the additional materials discussed above may further be used in cultures with low ammonium levels in the supernatant. In certain embodiments, supplemented cell culture media of use in the present invention result in ammonium levels in the cell culture solution of under 10 mM. In further embodiments, the supplemented cell culture media of the present invention is used with cell culture ammonium levels from about 0.5-9.5, 1.0-9.0, 1.5-8.5, 2.0-8.0, 2.5-7.5, 3.0-7.0, 3.5-6.5, 4.0-6.0, 4.5-5.5 mM.

In one embodiment, the copper and ammonium concentrations of a cell culture media and a cell culture supernatant are maintained for an extended period of time during the manufacturing process. In a specific embodiment, the copper and ammonium concentrations of a cell culture are maintained for the duration of a manufacturing process, i.e., during the time in which rVWF or rA13 is being expressed and recovered from a large-scale cell culture. In certain embodiments, the copper and ammonium concentrations are maintained in the culture solution at a level according to any one of variations 1 to 440, as set forth in Table 1. In a preferred embodiment the copper and ammonium concentrations are maintained for the entire time of such a production process.

In some embodiments, the culture medium provided by the invention may be provided in a liquid or a dry or powder form. The medium may be pre-aliquoted in an amount suitable for single use or provided in a larger quantity that may be used for more than one cell-culture. Generally, the medium of the invention will be provided in a sterile fashion.

Specific details of cell culture media of use for producing rVWF or rA13 are discussed below. Although the following are discussed with respect to either rVWF or rA13, it will be appreciated that any of the discussion provided below with respect to rVWF is applicable for rA13, and vice versa.

A. Recombinant VWF Cell Culture Media

One aspect of the present invention relates to a cell culture solution for producing recombinant vWF, more specifically, high molecular weight vWF having a high specific activity, which are further described herein. In one embodiment, the present invention provides a cell culture solution for producing high molecular weight, recombinant vWF, comprising a cell culture medium comprising a copper concentration of at least about 2.4 µg/L and a plurality of cells expressing highly multimeric vWF comprising about 14 to about 22 dimers and a specific Ristocetin co-factor activity of at least about 30 mU/µg.

In one embodiment, the cell culture solution further comprises an ammonium concentration of less than 10 mM. In a preferred embodiment, the cell culture comprises an ammonium concentration of no more than 5 mM. In yet other embodiments, the cell culture comprises an ammonium concentration of no more than 10 mM, or no more than 9 mM, 8 mM, 7 mM, 6 mM, 5 mM, 4 mM, 3 mM, 2 mM, 1 mM, or less. In yet other embodiments, the cell culture has a copper and ammonium concentration according to any one of variations 1 to 440, as set forth in Table 1. In certain embodiments, the ammonium concentration of the cell culture is maintained for an extended period at a concentration as provided above. For example, in one embodiment, the ammonium concentration is maintained at a low concentration for at least 3 days, or at least 4, 5, 6, 7, 8, 9, 10, 11, 12, 13, 14, 15, 16, 17, 18, 19, 20, 21, 28, 35, 42, 49, 56, 63, 70, or more days. In a specific embodiment, the ammonium concentration of the cell culture is maintained at an ammonium concentration of no more than 5 mM for at least 7 days. In another specific embodiment, the ammonium concentration of the cell culture is maintained at an ammonium concentration of no more than 4 mM for at least 7 days. In a specific embodiment, the ammonium concentration of the cell culture is maintained at an ammonium concentration of no more than 5 mM for at least 14 days. In another specific embodiment, the ammonium concentration of the cell culture is maintained at an ammonium concentration of no more than 4 mM for at least 14 days. In yet another embodiment, the ammonium concentration of the cell culture is maintained at a low level for the duration of the process (i.e., for the entire time the culture is being used to produce rVWF).

In one embodiment of the invention, the cell culture media can comprise a copper concentration of at least about 2.4 µg/L, in another embodiment at least about 3 µg/L, in yet another embodiment at least about 4 µg/L, in yet another embodiment at least about 8 µg/L, in yet another embodiment at least about 10 µg/L, in yet another embodiment at least about 15 µg/L, and in a further embodiment at least about 20 µg/L.

In other embodiments, the copper concentration in the cell culture media of the present invention can range from about 2.4 µg/L to about 20 µg/L, in another embodiment from about 2.4 µg/L to about 15 µg/L, in yet another embodiment from about 2.4 µg/L to about 10 µg/L, in yet another embodiment from about 2.4 µg/L to about 8 µg/L, in yet another embodiment from about 2.4 µg/L to about 6 µg/L, in yet another embodiment from about 2.4 µg/L to about 4 µg/L, in yet another embodiment from about 4 µg/L to about 20 µg/L, in yet another embodiment from about 4 µg/L to about 15 µg/L, in yet another embodiment from about 4 µg/L to about 10 µg/L, in yet another embodiment from about 4 µg/L to about 8 µg/L, and in a further embodiment from about 4 µg/L to about 6 µg/L.

The present invention also provides kits for the expression or production of rVWF, the kits comprising a culture medium suitable for the expression of rVWF having high specific activity.

B. ADAMTS13 (A13) Cell Culture Media

In one aspect, the present invention provides culture media that are useful for the expression of ADAMTS proteins having high specific activities. Advantageously, it has been found that by supplementing a culture medium with copper, that the activities of recombinant ADAMTS (e.g., rADAMTS13) enzymes expressed in cells cultured in the supplemented medium are greatly enhanced, while the enzymes are expressed at levels as high, if not higher, than cells cultured in non-supplemented mediums.

In one aspect, the present invention provides cell culture media supplemented with copper for the expression of recombinant ADAMTS13 protein with high specific activity. In one embodiment, the media are supplemented to result in a total copper concentration of from about 2 to about 4 µg/L. In further embodiments, the media are supplemented to results in a total copper concentration of from about 1-3, 2-3, 3-4 µg/L. In one embodiment, the media contain a copper concentration of at least 1 µg/L. In another embodiment, the media contains at least 2 µg/L copper. In another embodiment, the media contains at least 4 µg/L copper. In other embodiments, the media contains between 2 µg/L and 20 µg/L copper. In another embodiment, the media contains between 1 µg/L and 6 µg/L copper. In another embodiment, the media contains between 2 µg/L and 5 µg/L copper. In another embodiment, the media contains between 3 µg/L and 4 µg/L copper. In yet other embodiments, the media contains at least 1 µg/L copper, or at least 2 µg/L, 3 µg/L, 4 µg/L, 5 µg/L, 6 µg/L, 7 µg/L, 8 µg/L, 9 µg/L, 10 µg/L, 11 µg/L, 12 µg/L, 13 µg/L, 14 µg/L, 15 µg/L, 16 µg/L, 17 µg/L, 18 µg/L, 19 µg/L, 20 µg/L, or higher concentrations of copper.

In one embodiment, the cell culture solution further comprises an ammonium concentration of less than 10 mM. In a preferred embodiment, the cell culture solution comprises an ammonium concentration of no more than 5 mM. In yet other embodiments, the cell culture solution comprises an ammonium concentration of no more than 10 mM, or no more than 9 mM, 8 mM, 7 mM, 6 mM, 5 mM, 4 mM, 3 mM, 2 mM, 1 mM, or less. In yet other embodiments, the cell culture solution has a copper and ammonium concentration according to any one of variations 1 to 440, as set forth in Table 1. In certain embodiments, the ammonium concentration of the cell culture is maintained for an extended period at a concentration as provided above. For example, in one embodiment, the ammonium concentration is maintained at a low concentration for at least 3 days, or at least 4, 5, 6, 7, 8, 9, 10, 11, 12, 13, 14, 15, 16, 17, 18, 19, 20, 21, 28, 35, 42, 49, 56, 63, 70, or more days. In a specific embodiment, the ammonium concentration of the cell culture is maintained at an ammonium concentration of no more than 5 mM for at least 7 days. In another specific embodiment, the ammonium concentration of the cell culture is maintained at an ammonium concentration of no more than 4 mM for at least 7 days. In a specific embodiment, the ammonium concentration of the cell culture is maintained at an ammonium concentration of no more than 5 mM for at least 14 days. In another specific embodiment, the ammonium concentration of the cell culture is maintained at an ammonium concentration of no more than 4 mM for at least 14 days. In yet another embodiment, the ammonium concentration of the cell culture is maintained at a low level for the duration of the process (i.e., for the entire time the culture is being used to produce rA13).

In one embodiment, a culture medium is provided for the expression of a recombinant ADAMTS protein (e.g., rADAMTS13) containing at least 1 µg/L copper and at least 2 µM zinc. In other embodiments, the media contains at least 2 µg/L copper or at least 4 µg/L copper. In another embodiment wherein the media is supplemented with copper, the culture medium also contains at least at or about 5 µM zinc. In one embodiment, the culture medium also contains at or about between 2 µM and 12 µM zinc. In another embodiment, the culture medium also contains at or about between 5 µM and 12 µM zinc. In yet other embodiments, the culture medium also may contain at least at or about 2 µM, or at least at or about 3 µM, 4 µM, 5 µM, 6 µM, 7 µM, 8 µM, 9 µM, 10 µM, 11 µM, 12 µM, 13 µM, 14 µM, 15 µM, 20 µM, 25 µM, 30 µM, or more zinc. In one embodiment, the culture medium contains a copper and zinc concentration according to any one of variations 441 to 880, as set forth in Table 2.

TABLE 2

Exemplary embodiments of copper and zinc concentrations present in culture media useful for the expression of a recombinant ADAMTS13 protein.

|  |  | Zinc Concentration | | | | | | | | | | |
|---|---|---|---|---|---|---|---|---|---|---|---|---|
|  |  | AL 2 µM | AL 3 µM | AL 4 µM | AL 5 µM | AL 6 µM | AL 7 µM | AL 8 µM | AL 9 µM | AL 10 µM | 2-12 µM | 5-12 µM |
| Copper Concentration | AL 1 µg/L | Var. 441 | Var. 481 | Var. 521 | Var. 561 | Var. 601 | Var. 641 | Var. 681 | Var. 721 | Var. 761 | Var. 801 | Var. 841 |
|  | AL 2 µg/L | Var. 442 | Var. 482 | Var. 522 | Var. 562 | Var. 602 | Var. 642 | Var. 682 | Var. 722 | Var. 762 | Var. 802 | Var. 842 |
|  | AL 3 µg/L | Var. 443 | Var. 483 | Var. 523 | Var. 563 | Var. 603 | Var. 643 | Var. 683 | Var. 723 | Var. 763 | Var. 803 | Var. 843 |
|  | AL 4 µg/L | Var. 444 | Var. 484 | Var. 524 | Var. 564 | Var. 604 | Var. 644 | Var. 684 | Var. 724 | Var. 764 | Var. 804 | Var. 844 |
|  | AL 5 µg/L | Var. 445 | Var. 485 | Var. 525 | Var. 565 | Var. 605 | Var. 645 | Var. 685 | Var. 725 | Var. 765 | Var. 805 | Var. 845 |
|  | AL 6 µg/L | Var. 446 | Var. 486 | Var. 526 | Var. 566 | Var. 606 | Var. 646 | Var. 686 | Var. 726 | Var. 766 | Var. 806 | Var. 846 |
|  | AL 7 µg/L | Var. 447 | Var. 487 | Var. 527 | Var. 567 | Var. 607 | Var. 647 | Var. 687 | Var. 727 | Var. 767 | Var. 807 | Var. 847 |
|  | AL 8 µg/L | Var. 448 | Var. 488 | Var. 528 | Var. 568 | Var. 608 | Var. 648 | Var. 688 | Var. 728 | Var. 768 | Var. 808 | Var. 848 |
|  | AL 9 µg/L | Var. 449 | Var. 489 | Var. 529 | Var. 569 | Var. 609 | Var. 649 | Var. 689 | Var. 729 | Var. 769 | Var. 809 | Var. 849 |
|  | AL 10 µg/L | Var. 450 | Var. 490 | Var. 530 | Var. 570 | Var. 610 | Var. 650 | Var. 690 | Var. 730 | Var. 770 | Var. 810 | Var. 850 |
|  | About 1 µg/L | Var. 451 | Var. 491 | Var. 531 | Var. 571 | Var. 611 | Var. 651 | Var. 691 | Var. 731 | Var. 771 | Var. 811 | Var. 851 |
|  | About 1.5 µg/L | Var. 452 | Var. 492 | Var. 532 | Var. 572 | Var. 612 | Var. 652 | Var. 692 | Var. 732 | Var. 772 | Var. 812 | Var. 852 |
|  | About 2 µg/L | Var. 453 | Var. 493 | Var. 533 | Var. 573 | Var. 613 | Var. 653 | Var. 693 | Var. 733 | Var. 773 | Var. 813 | Var. 853 |
|  | About 2.5 µg/L | Var. 454 | Var. 494 | Var. 534 | Var. 574 | Var. 614 | Var. 654 | Var. 694 | Var. 734 | Var. 774 | Var. 814 | Var. 854 |
|  | About 3 µg/L | Var. 455 | Var. 495 | Var. 535 | Var. 575 | Var. 615 | Var. 655 | Var. 695 | Var. 735 | Var. 775 | Var. 815 | Var. 855 |
|  | About 3.5 µg/L | Var. 456 | Var. 496 | Var. 536 | Var. 576 | Var. 616 | Var. 656 | Var. 696 | Var. 736 | Var. 776 | Var. 816 | Var. 856 |
|  | About 4 µg/L | Var. 457 | Var. 497 | Var. 537 | Var. 577 | Var. 617 | Var. 657 | Var. 697 | Var. 737 | Var. 777 | Var. 817 | Var. 857 |
|  | About 4.5 µg/L | Var. 458 | Var. 498 | Var. 538 | Var. 578 | Var. 618 | Var. 658 | Var. 698 | Var. 738 | Var. 778 | Var. 818 | Var. 858 |
|  | About 5 µg/L | Var. 459 | Var. 499 | Var. 539 | Var. 579 | Var. 619 | Var. 659 | Var. 699 | Var. 739 | Var. 779 | Var. 819 | Var. 859 |
|  | About 5.5 µg/L | Var. 460 | Var. 500 | Var. 540 | Var. 580 | Var. 620 | Var. 660 | Var. 700 | Var. 740 | Var. 780 | Var. 820 | Var. 860 |
|  | About 6 µg/L | Var. 461 | Var. 501 | Var. 541 | Var. 581 | Var. 621 | Var. 661 | Var. 701 | Var. 741 | Var. 781 | Var. 821 | Var. 861 |
|  | About 7 µg/L | Var. 462 | Var. 502 | Var. 542 | Var. 582 | Var. 622 | Var. 662 | Var. 702 | Var. 742 | Var. 782 | Var. 822 | Var. 862 |
|  | About 8 µg/L | Var. 463 | Var. 503 | Var. 543 | Var. 583 | Var. 623 | Var. 663 | Var. 703 | Var. 743 | Var. 783 | Var. 823 | Var. 863 |
|  | About 9 µg/L | Var. 464 | Var. 504 | Var. 544 | Var. 584 | Var. 624 | Var. 664 | Var. 704 | Var. 744 | Var. 784 | Var. 824 | Var. 864 |
|  | About 10 µg/L | Var. 465 | Var. 505 | Var. 545 | Var. 585 | Var. 625 | Var. 665 | Var. 705 | Var. 745 | Var. 785 | Var. 825 | Var. 865 |
|  | 1-20 µg/L | Var. 466 | Var. 506 | Var. 546 | Var. 586 | Var. 626 | Var. 666 | Var. 706 | Var. 746 | Var. 786 | Var. 826 | Var. 866 |
|  | 2-20 µg/L | Var. 467 | Var. 507 | Var. 547 | Var. 587 | Var. 627 | Var. 667 | Var. 707 | Var. 747 | Var. 787 | Var. 827 | Var. 867 |
|  | 1-10 µg/L | Var. 468 | Var. 508 | Var. 548 | Var. 588 | Var. 628 | Var. 668 | Var. 708 | Var. 748 | Var. 788 | Var. 828 | Var. 868 |
|  | 2-10 µg/L | Var. 469 | Var. 509 | Var. 549 | Var. 589 | Var. 629 | Var. 669 | Var. 709 | Var. 749 | Var. 789 | Var. 829 | Var. 869 |
|  | 1-6 µg/L | Var. 470 | Var. 510 | Var. 550 | Var. 590 | Var. 630 | Var. 670 | Var. 710 | Var. 750 | Var. 790 | Var. 830 | Var. 870 |
|  | 2-6 µg/L | Var. 471 | Var. 511 | Var. 551 | Var. 591 | Var. 631 | Var. 671 | Var. 711 | Var. 751 | Var. 791 | Var. 831 | Var. 871 |
|  | 3-6 µg/L | Var. 472 | Var. 512 | Var. 552 | Var. 592 | Var. 632 | Var. 672 | Var. 712 | Var. 752 | Var. 792 | Var. 832 | Var. 872 |
|  | 4-6 µg/L | Var. 473 | Var. 513 | Var. 553 | Var. 593 | Var. 633 | Var. 673 | Var. 713 | Var. 753 | Var. 793 | Var. 833 | Var. 873 |
|  | 1-5 µg/L | Var. 474 | Var. 514 | Var. 554 | Var. 594 | Var. 634 | Var. 674 | Var. 714 | Var. 754 | Var. 794 | Var. 834 | Var. 874 |
|  | 2-5 µg/L | Var. 475 | Var. 515 | Var. 555 | Var. 595 | Var. 635 | Var. 675 | Var. 715 | Var. 755 | Var. 795 | Var. 835 | Var. 875 |
|  | 3-5 µg/L | Var. 476 | Var. 516 | Var. 556 | Var. 596 | Var. 636 | Var. 676 | Var. 716 | Var. 756 | Var. 796 | Var. 836 | Var. 876 |

TABLE 2-continued

Exemplary embodiments of copper and zinc concentrations present in culture media useful for the expression of a recombinant ADAMTS13 protein.

| | | Zinc Concentration | | | | | | | | | | |
|---|---|---|---|---|---|---|---|---|---|---|---|---|
| | | AL 2 µM | AL 3 µM | AL 4 µM | AL 5 µM | AL 6 µM | AL 7 µM | AL 8 µM | AL 9 µM | AL 10 µM | 2-12 µM | 5-12 µM |
| 4-5 µg/L | | Var. 477 | Var. 517 | Var. 557 | Var. 597 | Var. 637 | Var. 677 | Var. 717 | Var. 757 | Var. 797 | Var. 837 | Var. 877 |
| 1-4 µg/L | | Var. 478 | Var. 518 | Var. 558 | Var. 598 | Var. 638 | Var. 678 | Var. 718 | Var. 758 | Var. 798 | Var. 838 | Var. 878 |
| 2-4 µg/L | | Var. 479 | Var. 519 | Var. 559 | Var. 599 | Var. 639 | Var. 679 | Var. 719 | Var. 759 | Var. 799 | Var. 839 | Var. 879 |
| 3-4 µg/L | | Var. 480 | Var. 520 | Var. 560 | Var. 600 | Var. 640 | Var. 680 | Var. 720 | Var. 760 | Var. 800 | Var. 840 | Var. 880 |

AL = at least

In one embodiment, the cell culture solution further comprises a low ammonium concentration. In one embodiment, the cell culture solution comprises an ammonium concentration of less than 10 mM and a copper and zinc concentration according to any one of variations 441 to 880, as set forth in Table 2. In a specific embodiment, the ammonium is maintained at a concentration of no more than 10 mM for at least 7 days. In a preferred embodiment, the cell culture solution comprises an ammonium concentration of no more than 6 mM and a copper and zinc concentration according to any one of variations 441 to 880, as set forth in Table 2. In a specific embodiment, the ammonium is maintained at a concentration of no more than 6 mM for at least 7 days. In another preferred embodiment, the cell culture solution comprises an ammonium concentration of no more than 5 mM and a copper and zinc concentration according to any one of variations 441 to 880, as set forth in Table 2. In a specific embodiment, the ammonium is maintained at a concentration of no more than 5 mM for at least 7 days. In another preferred embodiment, the cell culture solution comprises an ammonium concentration of no more than 4 mM and a copper and zinc concentration according to any one of variations 441 to 880, as set forth in Table 2. In a specific embodiment, the ammonium is maintained at a concentration of no more than 4 mM for at least 7 days. In yet other embodiments, the cell culture solution comprises an ammonium concentration of no more than 10 mM, or no more than 9 mM, 8 mM, 7 mM, 6 mM, 5 mM, 4 mM, 3 mM, 2 mM, 1 mM, or less and a copper and zinc concentration according to any one of variations 441 to 880, as set forth in Table 2. In yet another specific embodiment, the ammonium concentration of the cell culture is maintained at a low level for the duration of the process (i.e., for the entire time the culture is being used to produce rA13).

In one embodiment, a culture medium is provided for the expression of a recombinant ADAMTS protein (e.g., rADAMTS13) containing at least 1 µg/L copper and at least at or about 0.5 mM calcium. In other embodiments, the media contains at least 2 µg/L copper or at least 4 µg/L copper. In another embodiment wherein the media is supplemented with copper, the culture medium also contains at least 1.5 mM calcium. In one embodiment, the culture medium contains at or about between 0.5 mM and 1.5 mM calcium. In yet other embodiments, the culture medium may contain at least at or about 0.5 mM, or at least at or about 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium. In one embodiment, the culture medium contains a copper and calcium concentration according to any one of variations 881 to 1320, as set forth in Table 3.

TABLE 3

Exemplary embodiments of copper and calcium concentrations present in culture media useful for the expression of a recombinant ADAMTS13 protein.

| | | Calcium Concentration | | | | | | | | | | |
|---|---|---|---|---|---|---|---|---|---|---|---|---|
| | | AL 0.5 mM | AL 0.75 mM | AL 1.0 mM | AL 1.25 mM | AL 1.5 mM | AL 2.0 mM | AL 2.5 mM | AL 3.0 mM | AL 4 mM | AL 5 mM | 0.5-1.5 mM |
| Copper Concentration | AL 1 µg/L | Var. 881 | Var. 921 | Var. 961 | Var. 1001 | Var. 1041 | Var. 1081 | Var. 1121 | Var. 1161 | Var. 1201 | Var. 1241 | Var. 1281 |
| | AL 2 µg/L | Var. 882 | Var. 922 | Var. 962 | Var. 1002 | Var. 1042 | Var. 1082 | Var. 1122 | Var. 1162 | Var. 1202 | Var. 1242 | Var. 1282 |
| | AL 3 µg/L | Var. 883 | Var. 923 | Var. 963 | Var. 1003 | Var. 1043 | Var. 1083 | Var. 1123 | Var. 1163 | Var. 1203 | Var. 1243 | Var. 1283 |
| | AL 4 µg/L | Var. 884 | Var. 924 | Var. 964 | Var. 1004 | Var. 1044 | Var. 1084 | Var. 1124 | Var. 1164 | Var. 1204 | Var. 1244 | Var. 1284 |
| | AL 5 µg/L | Var. 885 | Var. 925 | Var. 965 | Var. 1005 | Var. 1045 | Var. 1085 | Var. 1125 | Var. 1165 | Var. 1205 | Var. 1245 | Var. 1285 |
| | AL 6 µg/L | Var. 886 | Var. 926 | Var. 966 | Var. 1006 | Var. 1046 | Var. 1086 | Var. 1126 | Var. 1166 | Var. 1206 | Var. 1246 | Var. 1286 |
| | AL 7 µg/L | Var. 887 | Var. 927 | Var. 967 | Var. 1007 | Var. 1047 | Var. 1087 | Var. 1127 | Var. 1167 | Var. 1207 | Var. 1247 | Var. 1287 |
| | AL 8 µg/L | Var. 888 | Var. 928 | Var. 968 | Var. 1008 | Var. 1048 | Var. 1088 | Var. 1128 | Var. 1168 | Var. 1208 | Var. 1248 | Var. 1288 |
| | AL 9 µg/L | Var. 889 | Var. 929 | Var. 969 | Var. 1009 | Var. 1049 | Var. 1089 | Var. 1129 | Var. 1169 | Var. 1209 | Var. 1249 | Var. 1289 |

TABLE 3-continued

Exemplary embodiments of copper and calcium concentrations present in culture media useful for the expression of a recombinant ADAMTS13 protein.

| | Calcium Concentration | | | | | | | | | | |
|---|---|---|---|---|---|---|---|---|---|---|---|
| | AL 0.5 mM | AL 0.75 mM | AL 1.0 mM | AL 1.25 mM | AL 1.5 mM | AL 2.0 mM | AL 2.5 mM | AL 3.0 mM | AL 4 mM | AL 5 mM | 0.5-1.5 mM |
| AL 10 µg/L | Var. 890 | Var. 930 | Var. 970 | Var. 1010 | Var. 1050 | Var. 1090 | Var. 1130 | Var. 1170 | Var. 1210 | Var. 1250 | Var. 1290 |
| About 1 µg/L | Var. 891 | Var. 931 | Var. 971 | Var. 1011 | Var. 1051 | Var. 1091 | Var. 1131 | Var. 1171 | Var. 1211 | Var. 1251 | Var. 1291 |
| About 1.5 µg/L | Var. 892 | Var. 932 | Var. 972 | Var. 1012 | Var. 1052 | Var. 1092 | Var. 1132 | Var. 1172 | Var. 1212 | Var. 1252 | Var. 1292 |
| About 2 µg/L | Var. 893 | Var. 933 | Var. 973 | Var. 1013 | Var. 1053 | Var. 1093 | Var. 1133 | Var. 1173 | Var. 1213 | Var. 1253 | Var. 1293 |
| About 2.5 µg/L | Var. 894 | Var. 934 | Var. 974 | Var. 1014 | Var. 1054 | Var. 1094 | Var. 1134 | Var. 1174 | Var. 1214 | Var. 1254 | Var. 1294 |
| About 3 µg/L | Var. 895 | Var. 935 | Var. 975 | Var. 1015 | Var. 1055 | Var. 1095 | Var. 1135 | Var. 1175 | Var. 1215 | Var. 1255 | Var. 1295 |
| About 3.5 µg/L | Var. 896 | Var. 936 | Var. 976 | Var. 1016 | Var. 1056 | Var. 1096 | Var. 1136 | Var. 1176 | Var. 1216 | Var. 1256 | Var. 1296 |
| About 4 µg/L | Var. 897 | Var. 937 | Var. 977 | Var. 1017 | Var. 1057 | Var. 1097 | Var. 1137 | Var. 1177 | Var. 1217 | Var. 1257 | Var. 1297 |
| About 4.5 µg/L | Var. 898 | Var. 938 | Var. 978 | Var. 1018 | Var. 1058 | Var. 1098 | Var. 1138 | Var. 1178 | Var. 1218 | Var. 1258 | Var. 1298 |
| About 5 µg/L | Var. 899 | Var. 939 | Var. 979 | Var. 1019 | Var. 1059 | Var. 1099 | Var. 1139 | Var. 1179 | Var. 1219 | Var. 1259 | Var. 1299 |
| About 5.5 µg/L | Var. 900 | Var. 940 | Var. 980 | Var. 1020 | Var. 1060 | Var. 1100 | Var. 1140 | Var. 1180 | Var. 1220 | Var. 1260 | Var. 1300 |
| About 6 µg/L | Var. 901 | Var. 941 | Var. 981 | Var. 1021 | Var. 1061 | Var. 1101 | Var. 1141 | Var. 1181 | Var. 1221 | Var. 1261 | Var. 1301 |
| About 7 µg/L | Var. 902 | Var. 942 | Var. 982 | Var. 1022 | Var. 1062 | Var. 1102 | Var. 1142 | Var. 1182 | Var. 1222 | Var. 1262 | Var. 1302 |
| About 8 µg/L | Var. 903 | Var. 943 | Var. 983 | Var. 1023 | Var. 1063 | Var. 1103 | Var. 1143 | Var. 1183 | Var. 1223 | Var. 1263 | Var. 1303 |
| About 9 µg/L | Var. 904 | Var. 944 | Var. 984 | Var. 1024 | Var. 1064 | Var. 1104 | Var. 1144 | Var. 1184 | Var. 1224 | Var. 1264 | Var. 1304 |
| About 10 µg/L | Var. 905 | Var. 945 | Var. 985 | Var. 1025 | Var. 1065 | Var. 1105 | Var. 1145 | Var. 1185 | Var. 1225 | Var. 1265 | Var. 1305 |
| 1-20 µg/L | Var. 906 | Var. 946 | Var. 986 | Var. 1026 | Var. 1066 | Var. 1106 | Var. 1146 | Var. 1186 | Var. 1226 | Var. 1266 | Var. 1306 |
| 2-20 µg/L | Var. 907 | Var. 947 | Var. 987 | Var. 1027 | Var. 1067 | Var. 1107 | Var. 1147 | Var. 1187 | Var. 1227 | Var. 1267 | Var. 1307 |
| 1-10 µg/L | Var. 908 | Var. 948 | Var. 988 | Var. 1028 | Var. 1068 | Var. 1108 | Var. 1148 | Var. 1188 | Var. 1228 | Var. 1268 | Var. 1308 |
| 2-10 µg/L | Var. 909 | Var. 949 | Var. 989 | Var. 1029 | Var. 1069 | Var. 1109 | Var. 1149 | Var. 1189 | Var. 1229 | Var. 1269 | Var. 1309 |
| 1-6 µg/L | Var. 910 | Var. 950 | Var. 990 | Var. 1030 | Var. 1070 | Var. 1110 | Var. 1150 | Var. 1190 | Var. 1230 | Var. 1270 | Var. 1310 |
| 2-6 µg/L | Var. 911 | Var. 951 | Var. 991 | Var. 1031 | Var. 1071 | Var. 1111 | Var. 1151 | Var. 1191 | Var. 1231 | Var. 1271 | Var. 1311 |
| 3-6 µg/L | Var. 912 | Var. 952 | Var. 992 | Var. 1032 | Var. 1072 | Var. 1112 | Var. 1152 | Var. 1192 | Var. 1232 | Var. 1272 | Var. 1312 |
| 4-6 µg/L | Var. 913 | Var. 953 | Var. 993 | Var. 1033 | Var. 1073 | Var. 1113 | Var. 1153 | Var. 1193 | Var. 1233 | Var. 1273 | Var. 1313 |
| 1-5 µg/L | Var. 914 | Var. 954 | Var. 994 | Var. 1034 | Var. 1074 | Var. 1114 | Var. 1154 | Var. 1194 | Var. 1234 | Var. 1274 | Var. 1314 |
| 2-5 µg/L | Var. 915 | Var. 955 | Var. 995 | Var. 1035 | Var. 1075 | Var. 1115 | Var. 1155 | Var. 1195 | Var. 1235 | Var. 1275 | Var. 1315 |
| 3-5 µg/L | Var. 916 | Var. 956 | Var. 996 | Var. 1036 | Var. 1076 | Var. 1116 | Var. 1156 | Var. 1196 | Var. 1236 | Var. 1276 | Var. 1316 |
| 4-5 µg/L | Var. 917 | Var. 957 | Var. 997 | Var. 1037 | Var. 1077 | Var. 1117 | Var. 1157 | Var. 1197 | Var. 1237 | Var. 1277 | Var. 1317 |
| 1-4 µg/L | Var. 918 | Var. 958 | Var. 998 | Var. 1038 | Var. 1078 | Var. 1118 | Var. 1158 | Var. 1198 | Var. 1238 | Var. 1278 | Var. 1318 |
| 2-4 µg/L | Var. 919 | Var. 959 | Var. 999 | Var. 1039 | Var. 1079 | Var. 1119 | Var. 1159 | Var. 1199 | Var. 1239 | Var. 1279 | Var. 1319 |
| 3-4 µg/L | Var. 920 | Var. 960 | Var. 1000 | Var. 1040 | Var. 1080 | Var. 1120 | Var. 1160 | Var. 1200 | Var. 1240 | Var. 1280 | Var. 1320 |

AL = at least

In one embodiment, the cell culture solution further comprises a low ammonium concentration. In one embodiment, the cell culture solution comprises an ammonium concentration of less than 10 mM and a copper and calcium concentration according to any one of variations 881 to 1320, as set forth in Table 3. In a specific embodiment, the ammonium is maintained at a concentration of no more than 10 mM for at least 7 days. In a preferred embodiment, the cell culture medium comprises an ammonium concentration of no more than 6 mM and a copper and calcium concentration according to any one of variations 881 to 1320, as set forth in Table 3. In a specific embodiment, the ammonium is maintained at a concentration of no more than 6 mM for at least 7 days. In another preferred embodiment, the cell culture medium comprises an ammonium concentration of no more than 5 mM and a copper and calcium concentration according to any one of variations 881 to 1320, as set forth in Table 3. In a specific embodiment, the ammonium is maintained at a concentration of no more than 5 mM for at least 7 days. In another preferred embodiment, the cell culture medium comprises an ammonium concentration of no more than 4 mM and a copper and calcium concentration according to any one of variations 881 to 1320, as set forth in Table 3. In a specific embodiment, the ammonium is maintained at a concentration of no more than 4 mM for at least 7 days. In yet other embodiments, the cell culture medium comprises an ammonium concentration of no more than 10 mM, or no more than 9 mM, 8 mM, 7 mM, 6 mM, 5 mM, 4 mM, 3 mM, 2 mM, 1 mM, or less and a copper and calcium concentration according to any one of variations 881 to 1320, as set forth in Table 3. In yet another specific embodiment, the ammonium concentration of the cell culture is maintained at a low level for the duration of the process (i.e., for the entire time the culture is being used to produce rA13).

In one embodiment, the cell culture medium is supplemented with copper, zinc and calcium. In a specific embodiment, the culture medium has a calcium concentration of at least 0.5 mM and a copper and zinc concentration according to any one of variations 441 to 880, as set forth in Table 2. In another specific embodiment, the culture medium has a calcium concentration of at least 1.5 mM and a copper and zinc concentration according to any one of variations 441 to 880, as set forth in Table 2. In another specific embodiment, the culture medium has a calcium concentration between 0.5 mM and 1.5 mM and a copper and zinc concentration according to any one of variations 441 to 880, as set forth in Table 2. In yet other embodiments, the culture medium has a calcium concentration of at least 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more, and a copper and zinc concentration according to any one of variations 441 to 880, as set forth in Table 2.

In one embodiment, a culture medium is provided for the expression of a recombinant ADAMTS protein (e.g., rADAMTS13) containing at least 1 μg/L copper and at least 2 mg/L nicotinamide (vitamin B3). In other embodiments, the media contains at least 2 μg/L copper or at least 4 μg/L copper. In another embodiment wherein the media is supplemented with copper, the culture medium also contains at least 7 mg/L nicotinamide (vitamin B3). In one embodiment, the culture medium contains at or about between 2 mg/L and 10 mg/L nicotinamide (vitamin B3). In yet other embodiments, the culture medium may contain at least at or about 2 mg/L, 3 mg/L, 4 mg/L, 5 mg/L, 6 mg/L, 7 mg/L, 8 mg/L, 9 mg/L, 10 mg/L, 15 mg/L, 20 mg/L, or higher concentrations of nicotinamide (vitamin B3). In one embodiment, the culture medium contains a copper and nicotinamide concentration according to any one of variations 1321 to 1760, as set forth in Table 4.

TABLE 4

Exemplary embodiments of copper and nicotinamide concentrations present in culture media useful for the expression of a recombinant ADAMTS13 protein.

| | | Calcium Concentration | | | | | | | | | | |
|---|---|---|---|---|---|---|---|---|---|---|---|---|
| | | AL 2 mg/mL | AL 3 mg/mL | AL 4 mg/mL | AL 5 mg/mL | AL 6 mg/mL | AL 7 mg/mL | AL 8 mg/mL | AL 9 mg/mL | AL 10 mg/mL | AL 15 mg/mL | 2-10 mg/mL |
| Copper Concentration | AL 1 μg/L | Var. 1321 | Var. 1361 | Var. 1401 | Var. 1441 | Var. 1481 | Var. 1521 | Var. 1561 | Var. 1601 | Var. 1641 | Var. 1681 | Var. 1721 |
| | AL 2 μg/L | Var. 1322 | Var. 1362 | Var. 1402 | Var. 1442 | Var. 1482 | Var. 1522 | Var. 1562 | Var. 1602 | Var. 1642 | Var. 1682 | Var. 1722 |
| | AL 3 μg/L | Var. 1323 | Var. 1363 | Var. 1403 | Var. 1443 | Var. 1483 | Var. 1523 | Var. 1563 | Var. 1603 | Var. 1643 | Var. 1683 | Var. 1723 |
| | AL 4 μg/L | Var. 1324 | Var. 1364 | Var. 1404 | Var. 1444 | Var. 1484 | Var. 1524 | Var. 1564 | Var. 1604 | Var. 1644 | Var. 1684 | Var. 1724 |
| | AL 5 μg/L | Var. 1325 | Var. 1365 | Var. 1405 | Var. 1445 | Var. 1485 | Var. 1525 | Var. 1565 | Var. 1605 | Var. 1645 | Var. 1685 | Var. 1725 |
| | AL 6 μg/L | Var. 1326 | Var. 1366 | Var. 1406 | Var. 1446 | Var. 1486 | Var. 1526 | Var. 1566 | Var. 1606 | Var. 1646 | Var. 1686 | Var. 1726 |
| | AL 7 μg/L | Var. 1327 | Var. 1367 | Var. 1407 | Var. 1447 | Var. 1487 | Var. 1527 | Var. 1567 | Var. 1607 | Var. 1647 | Var. 1687 | Var. 1727 |
| | AL 8 μg/L | Var. 1328 | Var. 1368 | Var. 1408 | Var. 1448 | Var. 1488 | Var. 1528 | Var. 1568 | Var. 1608 | Var. 1648 | Var. 1688 | Var. 1728 |
| | AL 9 μg/L | Var. 1329 | Var. 1369 | Var. 1409 | Var. 1449 | Var. 1489 | Var. 1529 | Var. 1569 | Var. 1609 | Var. 1649 | Var. 1689 | Var. 1729 |
| | AL 10 μg/L | Var. 1330 | Var. 1370 | Var. 1410 | Var. 1450 | Var. 1490 | Var. 1530 | Var. 1570 | Var. 1610 | Var. 1650 | Var. 1690 | Var. 1730 |
| | About 1 μg/L | Var. 1331 | Var. 1371 | Var. 1411 | Var. 1451 | Var. 1491 | Var. 1531 | Var. 1571 | Var. 1611 | Var. 1651 | Var. 1691 | Var. 1731 |
| | About 1.5 μg/L | Var. 1332 | Var. 1372 | Var. 1412 | Var. 1452 | Var. 1492 | Var. 1532 | Var. 1572 | Var. 1612 | Var. 1652 | Var. 1692 | Var. 1732 |
| | About 2 μg/L | Var. 1333 | Var. 1373 | Var. 1413 | Var. 1453 | Var. 1493 | Var. 1533 | Var. 1573 | Var. 1613 | Var. 1653 | Var. 1693 | Var. 1733 |
| | About 2.5 μg/L | Var. 1334 | Var. 1374 | Var. 1414 | Var. 1454 | Var. 1494 | Var. 1534 | Var. 1574 | Var. 1614 | Var. 1654 | Var. 1694 | Var. 1734 |
| | About 3 μg/L | Var. 1335 | Var. 1375 | Var. 1415 | Var. 1455 | Var. 1495 | Var. 1535 | Var. 1575 | Var. 1615 | Var. 1655 | Var. 1695 | Var. 1735 |
| | About 3.5 μg/L | Var. 1336 | Var. 1376 | Var. 1416 | Var. 1456 | Var. 1496 | Var. 1536 | Var. 1576 | Var. 1616 | Var. 1656 | Var. 1696 | Var. 1736 |
| | About 4 μg/L | Var. 1337 | Var. 1377 | Var. 1417 | Var. 1457 | Var. 1497 | Var. 1537 | Var. 1577 | Var. 1617 | Var. 1657 | Var. 1697 | Var. 1737 |

TABLE 4-continued

Exemplary embodiments of copper and nicotinamide concentrations present in culture media useful for the expression of a recombinant ADAMTS13 protein.

| | Calcium Concentration | | | | | | | | | | |
|---|---|---|---|---|---|---|---|---|---|---|---|
| | AL 2 mg/mL | AL 3 mg/mL | AL 4 mg/mL | AL 5 mg/mL | AL 6 mg/mL | AL 7 mg/mL | AL 8 mg/mL | AL 9 mg/mL | AL 10 mg/mL | AL 15 mg/mL | 2-10 mg/mL |
| About 4.5 μg/L | Var. 1338 | Var. 1378 | Var. 1418 | Var. 1458 | Var. 1498 | Var. 1538 | Var. 1578 | Var. 1618 | Var. 1658 | Var. 1698 | Var. 1738 |
| About 5 μg/L | Var. 1339 | Var. 1379 | Var. 1419 | Var. 1459 | Var. 1499 | Var. 1539 | Var. 1579 | Var. 1619 | Var. 1659 | Var. 1699 | Var. 1739 |
| About 5.5 μg/L | Var. 1340 | Var. 1380 | Var. 1420 | Var. 1460 | Var. 1500 | Var. 1540 | Var. 1580 | Var. 1620 | Var. 1660 | Var. 1700 | Var. 1740 |
| About 6 μg/L | Var. 1341 | Var. 1381 | Var. 1421 | Var. 1461 | Var. 1501 | Var. 1541 | Var. 1581 | Var. 1621 | Var. 1661 | Var. 1701 | Var. 1741 |
| About 7 μg/L | Var. 1342 | Var. 1382 | Var. 1422 | Var. 1462 | Var. 1502 | Var. 1542 | Var. 1582 | Var. 1622 | Var. 1662 | Var. 1702 | Var. 1742 |
| About 8 μg/L | Var. 1343 | Var. 1383 | Var. 1423 | Var. 1463 | Var. 1503 | Var. 1543 | Var. 1583 | Var. 1623 | Var. 1663 | Var. 1703 | Var. 1743 |
| About 9 μg/L | Var. 1344 | Var. 1384 | Var. 1424 | Var. 1464 | Var. 1504 | Var. 1544 | Var. 1584 | Var. 1624 | Var. 1664 | Var. 1704 | Var. 1744 |
| About 10 μg/L | Var. 1345 | Var. 1385 | Var. 1425 | Var. 1465 | Var. 1505 | Var. 1545 | Var. 1585 | Var. 1625 | Var. 1665 | Var. 1705 | Var. 1745 |
| 1-20 μg/L | Var. 1346 | Var. 1386 | Var. 1426 | Var. 1466 | Var. 1506 | Var. 1546 | Var. 1586 | Var. 1626 | Var. 1666 | Var. 1706 | Var. 1746 |
| 2-20 μg/L | Var. 1347 | Var. 1387 | Var. 1427 | Var. 1467 | Var. 1507 | Var. 1547 | Var. 1587 | Var. 1627 | Var. 1667 | Var. 1707 | Var. 1747 |
| 1-10 μg/L | Var. 1348 | Var. 1388 | Var. 1428 | Var. 1468 | Var. 1508 | Var. 1548 | Var. 1588 | Var. 1628 | Var. 1668 | Var. 1708 | Var. 1748 |
| 2-10 μg/L | Var. 1349 | Var. 1389 | Var. 1429 | Var. 1469 | Var. 1509 | Var. 1549 | Var. 1589 | Var. 1629 | Var. 1669 | Var. 1709 | Var. 1749 |
| 1-6 μg/L | Var. 1350 | Var. 1390 | Var. 1430 | Var. 1470 | Var. 1510 | Var. 1550 | Var. 1590 | Var. 1630 | Var. 1670 | Var. 1710 | Var. 1750 |
| 2-6 μg/L | Var. 1351 | Var. 1391 | Var. 1431 | Var. 1471 | Var. 1511 | Var. 1551 | Var. 1591 | Var. 1631 | Var. 1671 | Var. 1711 | Var. 1751 |
| 3-6 μg/L | Var. 1352 | Var. 1392 | Var. 1432 | Var. 1472 | Var. 1512 | Var. 1552 | Var. 1592 | Var. 1632 | Var. 1672 | Var. 1712 | Var. 1752 |
| 4-6 μg/L | Var. 1353 | Var. 1393 | Var. 1433 | Var. 1473 | Var. 1513 | Var. 1553 | Var. 1593 | Var. 1633 | Var. 1673 | Var. 1713 | Var. 1753 |
| 1-5 μg/L | Var. 1354 | Var. 1394 | Var. 1434 | Var. 1474 | Var. 1514 | Var. 1554 | Var. 1594 | Var. 1634 | Var. 1674 | Var. 1714 | Var. 1754 |
| 2-5 μg/L | Var. 1355 | Var. 1395 | Var. 1435 | Var. 1475 | Var. 1515 | Var. 1555 | Var. 1595 | Var. 1635 | Var. 1675 | Var. 1715 | Var. 1755 |
| 3-5 μg/L | Var. 1356 | Var. 1396 | Var. 1436 | Var. 1476 | Var. 1516 | Var. 1556 | Var. 1596 | Var. 1636 | Var. 1676 | Var. 1716 | Var. 1756 |
| 4-5 μg/L | Var. 1357 | Var. 1397 | Var. 1437 | Var. 1477 | Var. 1517 | Var. 1557 | Var. 1597 | Var. 1637 | Var. 1677 | Var. 1717 | Var. 1757 |
| 1-4 μg/L | Var. 1358 | Var. 1398 | Var. 1438 | Var. 1478 | Var. 1518 | Var. 1558 | Var. 1598 | Var. 1638 | Var. 1678 | Var. 1718 | Var. 1758 |
| 2-4 μg/L | Var. 1359 | Var. 1399 | Var. 1439 | Var. 1479 | Var. 1519 | Var. 1559 | Var. 1599 | Var. 1639 | Var. 1679 | Var. 1719 | Var. 1759 |
| 3-4 μg/L | Var. 1360 | Var. 1400 | Var. 1440 | Var. 1480 | Var. 1520 | Var. 1560 | Var. 1600 | Var. 1640 | Var. 1680 | Var. 1720 | Var. 1760 |

AL = at least

In one embodiment, the cell culture solution further comprises a low ammonium concentration. In one embodiment, the culture medium comprises an ammonium concentration of less than 10 mM and a copper and nicotinamide concentration according to any one of variations 1321 to 1760, as set forth in Table 4. In a specific embodiment, the ammonium is maintained at a concentration of no more than 10 mM for at least 7 days. In a preferred embodiment, the cell culture solution comprises an ammonium concentration of no more than 6 mM and a copper and nicotinamide concentration according to any one of variations 1321 to 1760, as set forth in Table 4. In a specific embodiment, the ammonium is maintained at a concentration of no more than 6 mM for at least 7 days. In another preferred embodiment, the cell culture solution comprises an ammonium concentration of no more than 5 mM and a copper and nicotinamide concentration according to any one of variations 1321 to 1760, as set forth in Table 4. In a specific embodiment, the ammonium is maintained at a concentration of no more than 5 mM for at least 7 days. In another preferred embodiment, the cell culture solution comprises an ammonium concentration of no more than 4 mM and a copper and nicotinamide concentration according to any one of variations 1321 to 1760, as set forth in Table 4. In a specific embodiment, the ammonium is maintained at a concentration of no more than 4 mM for at least 7 days. In yet other embodiments, the cell culture solution comprises an ammonium concentration of no more than 10 mM, or no more than 9 mM, 8 mM, 7 mM, 6 mM, 5 mM, 4 mM, 3 mM, 2 mM, 1 mM, or less and a copper and nicotinamide concentration according to any one of variations 1321 to 1760, as set forth in Table 4. In yet another specific embodiment, the ammonium concentration of the cell culture is maintained at a low level for the duration of the process (i.e., for the entire time the culture is being used to produce rA13).

In one embodiment, the cell culture medium is supplemented with copper, zinc and nicotinamide. In a specific embodiment, the culture medium has a nicotinamide concentration of at least 2 mg/mL and a copper and zinc concentration according to any one of variations 441 to 880, as set forth in Table 2. In another specific embodiment, the culture medium has a nicotinamide concentration of at least 7 mg/mL mM and a copper and zinc concentration according to any one of variations 441 to 880, as set forth in Table 2. In another specific embodiment, the culture medium has a nicotinamide concentration between 2 mg/mL and 10 mg/mL and a copper and zinc concentration according to any one of variations 441 to 880, as set forth in Table 2. In yet other embodiments, the culture medium has a nicotinamide concentration of at least 2 mg/mL, 3 mg/mL, 4 mg/mL, 5 mg/mL, 6 mg/mL, 7 mg/mL, 8 mg/mL, 9 mg/mL, 10 mg/mL, 11 mg/mL, 12 mg/mL, 13 mg/mL, 14 mg/mL, 15 mg/mL, or more, and a copper and zinc concentration according to any one of variations 441 to 880, as set forth in Table 2.

In one embodiment, the cell culture medium is supplemented with copper, calcium and nicotinamide. In a specific embodiment, the culture medium has a nicotinamide concentration of at least 2 mg/mL and a copper and calcium concentration according to any one of variations 881 to 1320, as set forth in Table 3. In another specific embodiment, the culture medium has a nicotinamide concentration of at least 7 mg/mL mM and a copper and calcium concentration according to any one of variations 881 to 1320, as set forth in Table 3. In another specific embodiment, the culture medium has a nicotinamide concentration between 2 mg/mL and 10 mg/mL and a copper and calcium concentration according to any one of variations 881 to 1320, as set forth in Table 3. In yet other embodiments, the culture medium has a nicotinamide concentration of at least 2 mg/mL, 3 mg/mL, 4 mg/mL, 5 mg/mL, 6 mg/mL, 7 mg/mL, 8 mg/mL, 9 mg/mL, 10 mg/mL, 11 mg/mL, 12 mg/mL, 13 mg/mL, 14 mg/mL, 15 mg/mL, or more, and a copper and calcium concentration according to any one of variations 881 to 1320, as set forth in Table 3.

IV. Methods for the Production of Blood Factors Having High Specific Activity

A. Cell Cultivation Methods

The present invention provides methods for large-scale production of recombinant proteins (such as rVWF and rA13). In certain embodiments, such large-scale production methods utilize stirred/agitated tank reactors for manufacture of these therapeutic recombinant proteins.

In certain embodiments, the methods of the present invention can comprise the use of a cell culture system operated under a batch or continuous mode of operation. For example, when batch cell cultures are utilized, they may be operated under single batch, fed-batch, or repeated-batch mode. Likewise, continuous cell cultures may be operated under, for example, perfusion, turbidostat or chemostat mode. Batch and continuous cell cultivation may be performed under either suspension or adherence conditions. When operated under suspension conditions, the cells will be freely suspended and mixed within the culture medium. Alternatively, under adherence conditions, the cells will be bound to a solid phase, for example, a microcarrier, a porous microcarrier, disk carrier, ceramic cartridge, hollow fiber, flat sheet, gel matrix, and the like.

A batch culture is typically a large scale cell culture in which a cell inoculum is cultured to a maximum density in a tank or fermenter, and harvested and processed as a single batch. A fed-batch culture it typically a batch culture which is supplied with either fresh nutrients (e.g., growth-limiting substrates) or additives (e.g., precursors to products). The feed solution is usually highly concentrated to avoid dilution of the bioreactor. In a repeated-batch culture, the cells are placed in a culture medium and grown to a desired cell density. To avoid the onset of a decline phase and cell death, the culture is then diluted with complete growth medium before the cells reach their maximum concentration. The amount and frequency of dilution varies widely and depends on the growth characteristics of the cell line and convenience of the culture process. The process can be repeated as many times as required and, unless cells and medium are discarded at subculture, the volume of culture will increase stepwise as each dilution is made. The increasing volume may be handled by having a reactor of sufficient size to allow dilutions within the vessel or by dividing the diluted culture into several vessels. The rationale of this type of culture is to maintain the cells in an exponentially growing state. Serial subculture is characterized in that the volume of culture is always increasing stepwise, there can be multiple harvests, the cells continue to grow and the process can continue for as long as desired. In certain embodiments, a recombinant ADAMTS protein (e.g., rADAMTS13) may be recovered after harvesting the supernatant of a batch culture. In other embodiments, a recombinant VWF may be recovered after harvesting the supernatant of a batch culture.

A continuous culture can be a suspension culture that is continuously supplied with nutrients by the inflow of fresh medium, wherein the culture volume is usually kept constant by the concomitant removal of spent medium. In chemostat and turbidostat methods, the extracted medium contains cells. Thus, the cells remaining in the cell culture vessel must grow to maintain a steady state. In the chemostat method, the growth rate is typically controlled by controlling the dilution rate, i.e., the rate at which fresh medium is added. The growth rate of the cells in the culture may be controlled, for example, at a sub-maximal growth rate, by alteration of the dilution rate. In contrast, in the turbidostat method, the dilution rate is set to permit the maximum growth rate that the cells can achieve at the given operating conditions, such as pH and temperature. In certain embodiments, the rVWF or rA13 is recovered after harvesting the supernatant of a continuous culture. An exemplary method for continuous cell cultivation is described in WO/2011/012725 (Grillberger et al.), the content of which is hereby incorporated by reference in its entirety for all purposes.

In a perfusion culture, the extracted medium is depleted of cells, which are retained in the culture vessel, for example, by filtration or by centrifugal methods that lead to the reintroduction of the cells into the culture. However, typically membranes used for filtration do not retain 100% of cells, and so a proportion is removed when the medium is extracted. It may not be crucial to operate perfusion cultures at very high growth rates, as the majority of the cells are retained in the culture vessel. In certain embodiments, the rVWF or rA13 is recovered after harvesting the supernatant of a perfusion culture.

Stirred-tank reactor system can be used for batch and continuous cell cultures operated under suspension or adherent modes. Generally, the stirred-tank reactor system can be operated as any conventional stirred-tank reactor with any type of agitator such as a Rushton, hydrofoil, pitched blade, or marine.

In certain embodiments, the cell-culture methods of the invention may comprise the use of a microcarrier. In some embodiments, the cell-cultures of the embodiments can be performed in large bioreactors under conditions suitable for providing high volume-specific culture surface areas to achieve high cell densities and protein expression. One means for providing such growth conditions is to use microcarriers for cell-culture in stirred tank bioreactors. The concept of cell-growth on microcarriers was first described by van Wezel (van Wezel, A. L., Nature 216:64-5 (1967)) and allows for cell attachment on the surface of small solid particles suspended in the growth medium. These methods provide for high surface-to-volume ratios and thus allow for efficient nutrient utilization. Furthermore, for expression of secreted proteins in eukaryotic cell lines, the increased surface-to-volume ratio allows for higher levels of secretion and thus higher protein yields in the supernatant of the culture. Finally, these methods allow for the easy scale-up of eukaryotic expression cultures.

The cells expressing vWF and/or rA13 can be bound to a spherical or a porous microcarrier during cell culture growth. The microcarrier can be a microcarrier selected from the group of microcarriers based on dextran, collagen, plastic, gelatine and cellulose and others as described in Butler (1988. In: Spier & Griffiths, Animal Cell Biotechnology 3:283-303). It is also possible to grow the cells to a biomass on spherical microcarriers and subculture the cells when they have reached final fermenter biomass and prior to production of the expressed protein on a porous microcarrier or vice versa. Suitable spherical microcarriers can include smooth surface microcarriers, such as Cytodex™ 1, Cytodex™ 2, and Cytodex™ 3 (GE Healthcare) and macroporous microcarriers such as Cytopore™ 1, Cytopore™ 2, Cytoline™ 1, and Cytoline™ 2 (GE Healthcare).

As described above, the present invention includes cell culture media having an increased copper concentration. It is understood that all of the embodiments and concentrations described in the "Cell Culture Media" section above can be applied to the methods of the present invention described herein.

In certain embodiments, the culture can be maintained for at least about 7 days, or at least about 14 days, 21 days, 28 days, or at least about 5 weeks, 6 weeks, 7 weeks, 8 weeks, 9 weeks, or at least about 2 months, or 3, 4, 5, 6, 7, 8, 9, 10, 11, 12, 13, 14, 15, 16, 17, 18 months or longer. The cell density at which a cell-culture is maintained at for production of a recombinant vWF or recombinant rA13 protein will depend upon the culture-conditions and medium used for protein expression. One of skill in the art will readily be able to determine the optimal cell density for a cell-culture producing rVWF or rA13. In one embodiment, the culture is maintained at a cell density of between about $0.5 \times 10^6$ and $4 \times 10^7$ cells/mL for an extended period of time. In other embodiments, the cell density is maintained at a concentration of between about $1.0 \times 10^6$ and about $1.0 \times 10^7$ cells/mL for an extended period of time. In other embodiments, the cell density is maintained at a concentration of between about $1.0 \times 10^6$ and about $4.0 \times 10^6$ cells/mL for an extended period of time. In other embodiments, the cell density is maintained at a concentration of between about $1.0 \times 10^6$ and about $4.0 \times 10^6$ cells/mL for an extended period of time. In yet other embodiments, the cell density may be maintained at a concentration between about $2.0 \times 10^6$ and about $4.0 \times 10^6$ cells/mL, or between about $1.0 \times 10^6$ and about $2.5 \times 10^6$ cells/mL, or between about $1.5 \times 10^6$ and about $3.5 \times 10^6$ cells/mL, or any other similar range, for an extended period of time.

In one embodiment, the cell density of a continuous cell culture provided herein is maintained at a concentration of no more than $4.0 \times 10^6$ cells/mL for at least 7 days. In a specific embodiment, the cell density of a continuous cell culture provided herein is maintained at a concentration of no more than $4.0 \times 10^6$ cells/mL for at least 14 days. In a more specific embodiment, the cell density of a continuous cell culture provided herein is maintained at a concentration of no more than $4.0 \times 10^6$ cells/mL for at least 21 days. In a yet more specific embodiment, the cell density of a continuous cell culture provided herein is maintained at a concentration of no more than $4.0 \times 10^6$ cells/mL for at least 28 days. In a yet more specific embodiment, the cell density of a continuous cell culture provided herein is maintained at a concentration of no more than $4.0 \times 10^6$ cells/mL for at least 5 weeks. In a yet more specific embodiment, the cell density of a continuous cell culture provided herein is maintained at a concentration of no more than $4.0 \times 10^6$ cells/mL for at least 6 weeks. In a yet more specific embodiment, the cell density of a continuous cell culture provided herein is maintained at a concentration of no more than $4.0 \times 10^6$ cells/mL for at least 7 weeks. In a yet more specific embodiment, the cell density of a continuous cell culture provided herein is maintained at a concentration of no more than $4.0 \times 10^6$ cells/mL for at least 8 weeks. In a yet more specific embodiment, the cell density of a continuous cell culture provided herein is maintained at a concentration of no more than $4.0 \times 10^6$ cells/mL for at least 9 weeks.

In one embodiment, the cell density of a continuous cell culture provided herein is maintained at a concentration of no more than $3.5 \times 10^6$ cells/mL for at least 7 days. In a specific embodiment, the cell density of a continuous cell culture provided herein is maintained at a concentration of no more than $3.5 \times 10^6$ cells/mL for at least 14 days. In a more specific embodiment, the cell density of a continuous cell culture provided herein is maintained at a concentration of no more than $3.5 \times 10^6$ cells/mL for at least 21 days. In a yet more specific embodiment, the cell density of a continuous cell culture provided herein is maintained at a concentration of no more than $3.5 \times 10^6$ cells/mL for at least 28 days. In a yet more specific embodiment, the cell density of a continuous cell culture provided herein is maintained at a concentration of no more than $3.5 \times 10^6$ cells/mL for at least 5 weeks. In a yet more specific embodiment, the cell density of a continuous cell culture provided herein is maintained at a concentration of no more than $3.5 \times 10^6$ cells/mL for at least 6 weeks. In a yet more specific embodiment, the cell density of a continuous cell culture provided herein is maintained at a concentration of no more than $3.5 \times 10^6$ cells/mL for at least 7 weeks. In a yet more specific embodiment, the cell density of a continuous cell culture provided herein is maintained at a concentration of no more than $3.5 \times 10^6$ cells/mL for at least 8 weeks. In a yet more specific embodiment, the cell density of a continuous cell culture provided herein is maintained at a concentration of no more than $3.5 \times 10^6$ cells/mL for at least 9 weeks.

In one embodiment, the cell density of a continuous cell culture provided herein is maintained at a concentration of no more than $3.0 \times 10^6$ cells/mL for at least 7 days. In a specific embodiment, the cell density of a continuous cell culture provided herein is maintained at a concentration of no more than $3.0 \times 10^6$ cells/mL for at least 14 days. In a more specific embodiment, the cell density of a continuous cell culture provided herein is maintained at a concentration of no more than $3.0 \times 10^6$ cells/mL for at least 21 days. In a yet more specific embodiment, the cell density of a continuous cell culture provided herein is maintained at a concentration of no more than $3.0 \times 10^6$ cells/mL for at least 28 days. In a yet more specific embodiment, the cell density of a continuous cell culture provided herein is maintained at a concentration of no more than $3.0 \times 10^6$ cells/mL for at least 5 weeks. In a yet more specific embodiment, the cell density of a continuous cell culture provided herein is maintained at a concentration of no more than $3.0 \times 10^6$ cells/mL for at least 6 weeks. In a yet more specific embodiment, the cell density of a continuous cell culture provided herein is maintained at a concentration of no more than $3.0 \times 10^6$ cells/mL for at least 7 weeks. In a yet more specific embodiment, the cell density of a continuous cell culture provided herein is maintained at a concentration of no more than $3.0 \times 10^6$ cells/mL for at least 8 weeks. In a yet more specific embodiment, the cell density of a continuous cell culture provided herein is maintained at a concentration of no more than $3.0 \times 10^6$ cells/mL for at least 9 weeks.

In one embodiment, the cell density of a continuous cell culture provided herein is maintained at a concentration of no more than $2.5 \times 10^6$ cells/mL for at least 7 days. In a specific embodiment, the cell density of a continuous cell culture provided herein is maintained at a concentration of no more than $2.5 \times 10^6$ cells/mL for at least 14 days. In a more specific embodiment, the cell density of a continuous cell culture provided herein is maintained at a concentration of no more than $2.5 \times 10^6$ cells/mL for at least 21 days. In a yet more specific embodiment, the cell density of a continuous cell culture provided herein is maintained at a concentration of no more than $2.5 \times 10^6$ cells/mL for at least 28 days. In a yet more specific embodiment, the cell density of a continuous cell culture provided herein is maintained at a concentration of no more than $2.5 \times 10^6$ cells/mL for at least 5 weeks. In a yet more specific embodiment, the cell density of a continuous cell culture provided herein is maintained at a concentration of no more than $2.5 \times 10^6$ cells/mL for at least 6 weeks. In a yet more specific embodiment, the cell density of a continuous cell culture provided herein is maintained at a concentration of no more than $2.5 \times 10^6$ cells/mL for at least 7 weeks. In a yet more specific embodiment, the cell density of a continuous cell culture provided herein is maintained at a concentration of no more than $2.5 \times 10^6$ cells/mL for at least 8 weeks. In a yet more specific embodiment, the cell density of a continuous cell culture provided herein is maintained at a concentration of no more than $2.5 \times 10^6$ cells/mL for at least 9 weeks.

In another embodiment, the cell density of a continuous cell culture provided herein is maintained at a concentration of no more than $2.0 \times 10^6$ cells/mL for at least 7 days. In a specific embodiment, the cell density of a continuous cell culture provided herein is maintained at a concentration of no more than $2.0 \times 10^6$ cells/mL for at least 14 days. In a more specific embodiment, the cell density of a continuous cell culture provided herein is maintained at a concentration of no more than $2.0 \times 10^6$ cells/mL for at least 21 days. In a yet more specific embodiment, the cell density of a continuous cell culture provided herein is maintained at a concentration of no more than $2.0 \times 10^6$ cells/mL for at least 28 days. In a yet more specific embodiment, the cell density of a continuous cell culture provided herein is maintained at a concentration of no more than $2.0 \times 10^6$ cells/mL for at least 5 weeks. In a yet more specific embodiment, the cell density of a continuous cell culture provided herein is maintained at a concentration of no more than $2.0 \times 10^6$ cells/mL for at least 6 weeks. In a yet more specific embodiment, the cell density of a continuous cell culture provided herein is maintained at a concentration of no more than $2.0 \times 10^6$ cells/mL for at least 7 weeks. In a yet more specific embodiment, the cell density of a continuous cell culture provided herein is maintained at a concentration of no more than $2.0 \times 10^6$ cells/mL for at least 8 weeks. In a yet more specific embodiment, the cell density of a continuous cell culture provided herein is maintained at a concentration of no more than $2.0 \times 10^6$ cells/mL for at least 9 weeks.

In one embodiment, the cell density of a continuous cell culture provided herein is maintained at a concentration of no more than $1.5 \times 10^6$ cells/mL for at least 7 days. In a specific embodiment, the cell density of a continuous cell culture provided herein is maintained at a concentration of no more than $1.5 \times 10^6$ cells/mL for at least 14 days. In a more specific embodiment, the cell density of a continuous cell culture provided herein is maintained at a concentration of no more than $1.5 \times 10^6$ cells/mL for at least 21 days. In a yet more specific embodiment, the cell density of a continuous cell culture provided herein is maintained at a concentration of no more than $1.5 \times 10^6$ cells/mL for at least 28 days. In a yet more specific embodiment, the cell density of a continuous cell culture provided herein is maintained at a concentration of no more than $1.5 \times 10^6$ cells/mL for at least 5 weeks. In a yet more specific embodiment, the cell density of a continuous cell culture provided herein is maintained at a concentration of no more than $1.5 \times 10^6$ cells/mL for at least 6 weeks. In a yet more specific embodiment, the cell density of a continuous cell culture provided herein is maintained at a concentration of no more than $1.5 \times 10^6$ cells/mL for at least 7 weeks. In a yet more specific embodiment, the cell density of a continuous cell culture provided herein is maintained at a concentration of no more than $1.5 \times 10^6$ cells/mL for at least 8 weeks. In a yet more specific embodiment, the cell density of a continuous cell culture provided herein is maintained at a concentration of no more than $1.5 \times 10^6$ cells/mL for at least 9 weeks.

The following provides specific details on methods for producing rVWF and rA13. As will be appreciated, although the conditions are presented specifically for rVWF or rA13, the conditions for rVWF can be used for producing rA13 and vice versa.

B. Methods of Producing High Molecular Weight Recombinant vWF

In another aspect, the present invention further relates to methods for producing vWF under cell culture conditions comprising a cell culture medium having an increased copper concentration. In certain embodiments, the culture also comprises a low ammonium concentration. As used herein, the term "cell culture" and "cell culture solution" are used interchangeably.

In one embodiment, the present invention provides a method of producing a high molecular weight, recombinant vWF, comprising: a) providing a culture of cells; b) introducing a nucleic acid sequence coding for vWF; c) selecting the cells carrying the nucleic acid sequence; and, d) expressing vWF in the cells under cell culture conditions comprising a cell culture medium comprising a copper concentration of at least about 2.4 µg/L and a cell culture supernatant comprising an ammonium concentration less than about 10 mM, wherein the vWF is highly multimeric vWF comprising about 14 to about 22 dimers and a specific Ristocetin activity of at least about 30 mU/µg. In further embodiments, the multimeric rVWF produced using methods of the present invention comprise about 10-30, 12-28, 14-26, 16-24, 18-22, 20-21 dimers. In still further embodiments, the rVWF produced in accordance with the present invention has a specific activity of at least about 20, 22.5, 25, 27.5, 30, 32.5, 35, 37.5, 40, 42.5, 45, 47.5, 50, 52.5, 55, 57.5, 60, 62.5, 65, 67.5, 70, 72.5, 75, 77.5, 80, or more mU/µg. In a specific embodiment, the cell density of the continuous cell culture for production of rVWF is maintained at a concentration of no more than $2.5 \times 10^6$ cells/mL for an extended period. In other specific embodiments, the cell density is maintained at no more than $2.0 \times 10^6$ cells/mL, $1.5 \times 10^6$ cells/mL, $1.0 \times 10^6$ cells/mL, $0.5 \times 10^6$ cells/mL, or less. In one embodiment, the cell density is maintained at between $1.5 \times 10^6$ cells/mL and $2.5 \times 10^6$ cells/mL.

In one embodiment, the present invention provides a method for producing a recombinant Von Willebrand Factor (rVWF) composition, the method comprising the steps of: (a) providing a basal cell culture media; (b) supplementing the basal cell culture media with copper to provide a final copper concentration of at least 2.0 µg/L; (c) providing one or more cells comprising a nucleic acid encoding a rVWF protein; (d)

culturing the one or more cells in the copper supplemented cell culture media such that rVWF is expressed and excreted from the cells into a culture supernatant; and (e) recovering at least a portion of the culture supernatant, wherein the recovered supernatant has a rVWF specific ristocetin cofactor activity of at least 30 mU/μg rVWF. In one embodiment, the cell culture solution further comprises an ammonium concentration of less than 10 mM. In another specific embodiment, the ammonium concentration of the cell culture solution is maintained at an ammonium concentration of no more than 10 mM for at least 7 days. In a preferred embodiment, the cell culture solution comprises an ammonium concentration of no more than 5 mM. In another specific embodiment, the ammonium concentration of the cell culture solution is maintained at an ammonium concentration of no more than 5 mM for at least 7 days. In a preferred embodiment, the cell culture solution comprises an ammonium concentration of no more than 4 mM. In another specific embodiment, the ammonium concentration of the cell culture is maintained at an ammonium concentration of no more than 4 mM for at least 7 days. In yet other embodiments, the cell culture solution comprises an ammonium concentration of no more than 10 mM, or no more than 9 mM, 8 mM, 7 mM, 6 mM, 5 mM, 4 mM, 3 mM, 2 mM, 1 mM, or less. In yet another embodiment, the ammonium concentration of the cell culture is maintained at a low level for the duration of the process (i.e., for the entire time the culture is being used to produce rVWF). In a preferred embodiment, the recovered supernatant has a rVWF specific ristocetin cofactor activity of at least 50 mU/μg rVWF. In a more preferred embodiment, the recovered supernatant has a rVWF specific ristocetin cofactor activity of at least 70 mU/μg rVWF.

In one embodiment of the method described above, the basal cell culture media is supplemented with copper to provide a final copper concentration of at least 2.4 μg/L. In one embodiment, the cell culture solution further comprises an ammonium concentration of less than 10 mM. In another specific embodiment, the ammonium concentration of the cell culture solution is maintained at an ammonium concentration of no more than 10 mM for at least 7 days. In a preferred embodiment, the cell culture solution comprises an ammonium concentration of no more than 5 mM. In another specific embodiment, the ammonium concentration of the cell culture solution is maintained at an ammonium concentration of no more than 5 mM for at least 7 days. In a preferred embodiment, the cell culture solution comprises an ammonium concentration of no more than 4 mM. In another specific embodiment, the ammonium concentration of the cell culture solution is maintained at an ammonium concentration of no more than 4 mM for at least 7 days. In yet other embodiments, the cell culture solution comprises an ammonium concentration of no more than 10 mM, or no more than 9 mM, 8 mM, 7 mM, 6 mM, 5 mM, 4 mM, 3 mM, 2 mM, 1 mM, or less. In yet another embodiment, the ammonium concentration of the cell culture solution is maintained at a low level for the duration of the process (i.e., for the entire time the culture is being used to produce rVWF). In a preferred embodiment, the recovered supernatant has a rVWF specific ristocetin cofactor activity of at least 50 mU/μg rVWF. In a more preferred embodiment, the recovered supernatant has a rVWF specific ristocetin cofactor activity of at least 70 mU/μg rVWF.

In one embodiment of the method described above, the basal cell culture media is supplemented with copper to provide a final copper concentration of at least 3 μg/L. In one embodiment, the cell culture solution further comprises an ammonium concentration of less than 10 mM. In another specific embodiment, the ammonium concentration of the cell culture solution is maintained at an ammonium concentration of no more than 10 mM for at least 7 days. In a preferred embodiment, the cell culture solution comprises an ammonium concentration of no more than 5 mM. In another specific embodiment, the ammonium concentration of the cell culture solution is maintained at an ammonium concentration of no more than 5 mM for at least 7 days. In a preferred embodiment, the cell culture solution comprises an ammonium concentration of no more than 4 mM. In another specific embodiment, the ammonium concentration of the cell culture solution is maintained at an ammonium concentration of no more than 4 mM for at least 7 days. In yet other embodiments, the cell culture solution comprises an ammonium concentration of no more than 10 mM, or no more than 9 mM, 8 mM, 7 mM, 6 mM, 5 mM, 4 mM, 3 mM, 2 mM, 1 mM, or less. In yet another embodiment, the ammonium concentration of the cell culture solution is maintained at a low level for the duration of the process (i.e., for the entire time the culture is being used to produce rVWF). In a preferred embodiment, the recovered supernatant has a rVWF specific ristocetin cofactor activity of at least 50 mU/μg rVWF. In a more preferred embodiment, the recovered supernatant has a rVWF specific ristocetin cofactor activity of at least 70 mU/μg rVWF.

In one embodiment of the method described above, the basal cell culture media is supplemented with copper to provide a final copper concentration of at least 4 μg/L. In one embodiment, the cell culture solution further comprises an ammonium concentration of less than 10 mM. In another specific embodiment, the ammonium concentration of the cell culture solution is maintained at an ammonium concentration of no more than 10 mM for at least 7 days. In a preferred embodiment, the cell culture solution comprises an ammonium concentration of no more than 5 mM. In another specific embodiment, the ammonium concentration of the cell culture solution is maintained at an ammonium concentration of no more than 5 mM for at least 7 days. In a preferred embodiment, the cell culture solution comprises an ammonium concentration of no more than 4 mM. In another specific embodiment, the ammonium concentration of the cell culture solution is maintained at an ammonium concentration of no more than 4 mM for at least 7 days. In yet other embodiments, the cell culture media comprises an ammonium concentration of no more than 10 mM, or no more than 9 mM, 8 mM, 7 mM, 6 mM, 5 mM, 4 mM, 3 mM, 2 mM, 1 mM, or less. In yet another embodiment, the ammonium concentration of the cell culture solution is maintained at a low level for the duration of the process (i.e., for the entire time the culture is being used to produce rVWF). In a preferred embodiment, the recovered supernatant has a rVWF specific ristocetin cofactor activity of at least 50 mU/μg rVWF. In a more preferred embodiment, the recovered supernatant has a rVWF specific ristocetin cofactor activity of at least 70 mU/μg rVWF.

In one embodiment of the method described above, the basal cell culture media is supplemented with copper to provide a final copper concentration of about 4.3 μg/L. In one embodiment, the cell culture solution further comprises an ammonium concentration of less than 10 mM. In another specific embodiment, the ammonium concentration of the cell culture solution is maintained at an ammonium concentration of no more than 10 mM for at least 7 days. In a preferred embodiment, the cell culture solution comprises an ammonium concentration of no more than 5 mM. In another specific embodiment, the ammonium concentration of the cell culture solution is maintained at an ammonium concentration of no more than 5 mM for at least 7 days. In a preferred embodiment, the cell culture solution comprises an ammonium concentration of no more than 4 mM. In another specific embodiment, the ammonium concentration of the cell culture solution is maintained at an ammonium concentration of no more than 4 mM for at least 7 days. In yet other embodiments, the cell culture solution comprises an ammonium concentration of no more than 10 mM, or no more than 9 mM, 8 mM, 7 mM, 6 mM, 5 mM, 4 mM, 3 mM, 2 mM, 1 mM, or less. In yet another embodiment, the ammonium concentration of the cell culture solution is maintained at a low level for the duration of the process (i.e., for the entire time the culture is being used to produce rVWF). In a preferred embodiment, the recovered supernatant has a rVWF specific ristocetin cofactor activity of at least 50 mU/μg rVWF. In a more preferred embodiment, the recovered supernatant has a rVWF specific ristocetin cofactor activity of at least 70 mU/μg rVWF.

In one embodiment of the method described above, the basal cell culture media is supplemented with copper to provide a final copper concentration of between 2 μg/L and 20 μg/L. In one embodiment, the cell culture solution further comprises an ammonium concentration of less than 10 mM. In another specific embodiment, the ammonium concentration of the cell culture solution is maintained at an ammonium concentration of no more than 10 mM for at least 7 days. In a preferred embodiment, the cell culture solution comprises an ammonium concentration of no more than 5 mM. In another specific embodiment, the ammonium concentration of the cell culture is maintained at an ammonium concentration of no more than 5 mM for at least 7 days. In a preferred embodiment, the cell culture solution comprises an ammonium concentration of no more than 4 mM. In another specific embodiment, the ammonium concentration of the cell culture is maintained at an ammonium concentration of no more than 4 mM for at least 7 days. In yet other embodiments, the cell culture solution comprises an ammonium concentration of no more than 10 mM, or no more than 9 mM, 8 mM, 7 mM, 6 mM, 5 mM, 4 mM, 3 mM, 2 mM, 1 mM, or less. In yet another embodiment, the ammonium concentration of the cell culture is maintained at a low level for the duration of the process (i.e., for the entire time the culture is being used to produce rVWF). In a preferred embodiment, the recovered supernatant has a rVWF specific ristocetin cofactor activity of at least 50 mU/μg rVWF. In a more preferred embodiment, the recovered supernatant has a rVWF specific ristocetin cofactor activity of at least 70 mU/μg rVWF.

In one embodiment of the method described above, the basal cell culture media is supplemented with copper to provide a final copper concentration of between 3 μg/L and 10 μg/L. In one embodiment, the cell culture solution further comprises an ammonium concentration of less than 10 mM. In another specific embodiment, the ammonium concentration of the cell culture is maintained at an ammonium concentration of no more than 10 mM for at least 7 days. In a preferred embodiment, the cell culture solution comprises an ammonium concentration of no more than 5 mM. In another specific embodiment, the ammonium concentration of the cell culture solution is maintained at an ammonium concentration of no more than 5 mM for at least 7 days. In a preferred embodiment, the cell culture solution comprises an ammonium concentration of no more than 4 mM. In another specific embodiment, the ammonium concentration of the cell culture is maintained at an ammonium concentration of no more than 4 mM for at least 7 days. In yet other embodiments, the cell culture solution comprises an ammonium concentration of no more than 10 mM, or no more than 9 mM, 8 mM, 7 mM, 6 mM, 5 mM, 4 mM, 3 mM, 2 mM, 1 mM, or less. In yet another embodiment, the ammonium concentration of the cell culture solution is maintained at a low level for the duration of the process (i.e., for the entire time the culture is being used to produce rVWF). In a preferred embodiment, the recovered supernatant has a rVWF specific ristocetin cofactor activity of at least 50 mU/μg rVWF. In a more preferred embodiment, the recovered supernatant has a rVWF specific ristocetin cofactor activity of at least 70 mU/μg rVWF.

In one embodiment of the method described above, the basal cell culture media is supplemented with copper to provide a final copper concentration of between 4 μg/L and 7.5 μg/L. In one embodiment, the cell culture solution further comprises an ammonium concentration of less than 10 mM. In another specific embodiment, the ammonium concentration of the cell culture is maintained at an ammonium concentration of no more than 10 mM for at least 7 days. In a preferred embodiment, the cell culture solution comprises an ammonium concentration of no more than 5 mM. In another specific embodiment, the ammonium concentration of the cell culture is maintained at an ammonium concentration of no more than 5 mM for at least 7 days. In a preferred embodiment, the cell culture solution comprises an ammonium concentration of no more than 4 mM. In another specific embodiment, the ammonium concentration of the cell culture is maintained at an ammonium concentration of no more than 4 mM for at least 7 days. In yet other embodiments, the cell culture solution comprises an ammonium concentration of no more than 10 mM, or no more than 9 mM, 8 mM, 7 mM, 6 mM, 5 mM, 4 mM, 3 mM, 2 mM, 1 mM, or less. In yet another embodiment, the ammonium concentration of the cell culture is maintained at a low level for the duration of the process (i.e., for the entire time the culture is being used to produce rVWF). In a preferred embodiment, the recovered supernatant has a rVWF specific ristocetin cofactor activity of at least 50 mU/μg rVWF. In a more preferred embodiment, the recovered supernatant has a rVWF specific ristocetin cofactor activity of at least 70 mU/μg rVWF.

In one embodiment, the present invention provides a method for producing a recombinant Von Willebrand Factor (rVWF) composition, the method comprising the steps of: (a) providing a basal cell culture media; (b) supplementing the basal cell culture media with copper; (c) providing one or more cells comprising a nucleic acid encoding a rVWF protein; (d) culturing the one or more cells in the copper supplemented cell culture media such that rVWF is expressed and excreted from the cells into a culture supernatant; and (e) recovering at least a portion of the culture supernatant, wherein the $NH_4^+$ concentration of the supernatant is maintained at a low level for at least 7 days, and further wherein the recovered supernatant has a rVWF specific ristocetin cofactor activity of at least 30 mU/μg rVWF. In a specific embodiment, the copper concentration and $NH_4^+$ concentration of the cell culture solution is maintained at a concentration according to any one of variations 1 to 440, as set forth in Table 1. In a preferred embodiment, the recovered supernatant has a rVWF specific ristocetin cofactor activity of at least 50 mU/μg rVWF. In a more preferred embodiment, the recovered supernatant has a rVWF specific ristocetin cofactor activity of at least 70 mU/μg rVWF.

In one embodiment of the method described above, the copper concentration and $NH_4^+$ concentration of the cell culture is maintained at a concentration according to any one of variations 1 to 440, as set forth in Table 1 for at least 14 days. In a preferred embodiment, the recovered supernatant has a rVWF specific ristocetin cofactor activity of at least 50 mU/μg rVWF. In a more preferred embodiment, the recovered supernatant has a rVWF specific ristocetin cofactor activity of at least 70 mU/μg rVWF.

In one embodiment of the method described above, the copper concentration and $NH_4^+$ concentration of the cell culture is maintained at a concentration according to any one of variations 1 to 440, as set forth in Table 1 for at least 21 days. In a preferred embodiment, the recovered supernatant has a rVWF specific ristocetin cofactor activity of at least 50 mU/μg rVWF. In a more preferred embodiment, the recovered supernatant has a rVWF specific ristocetin cofactor activity of at least 70 mU/μg rVWF.

In one embodiment of the method described above, the copper concentration and $NH_4^+$ concentration of the cell culture is maintained at a concentration according to any one of variations 1 to 440, as set forth in Table 1 for at least 28 days. In a preferred embodiment, the recovered supernatant has a rVWF specific ristocetin cofactor activity of at least 50 mU/μg rVWF. In a more preferred embodiment, the recovered supernatant has a rVWF specific ristocetin cofactor activity of at least 70 mU/μg rVWF.

In one embodiment of the method described above, the copper concentration and $NH_4^+$ concentration of the cell culture is maintained at a concentration according to any one of variations 1 to 440, as set forth in Table 1 for at least 5 weeks. In a preferred embodiment, the recovered supernatant has a rVWF specific ristocetin cofactor activity of at least 50 mU/μg rVWF. In a more preferred embodiment, the recovered supernatant has a rVWF specific ristocetin cofactor activity of at least 70 mU/μg rVWF.

In one embodiment of the method described above, the copper concentration and $NH_4^+$ concentration of the cell culture is maintained at a concentration according to any one of variations 1 to 440, as set forth in Table 1 for at least 6 weeks. In a preferred embodiment, the recovered supernatant has a rVWF specific ristocetin cofactor activity of at least 50 mU/μg rVWF. In a more preferred embodiment, the recovered supernatant has a rVWF specific ristocetin cofactor activity of at least 70 mU/μg rVWF.

In one embodiment of the method described above, the copper concentration and $NH_4^+$ concentration of the cell culture is maintained at a concentration according to any one of variations 1 to 440, as set forth in Table 1 for at least 7 weeks. In a preferred embodiment, the recovered supernatant has a rVWF specific ristocetin cofactor activity of at least 50 mU/μg rVWF. In a more preferred embodiment, the recovered supernatant has a rVWF specific ristocetin cofactor activity of at least 70 mU/μg rVWF.

In one embodiment of the method described above, the copper concentration and $NH_4^+$ concentration of the cell culture is maintained at a concentration according to any one of variations 1 to 440, as set forth in Table 1 for at least 8 weeks. In a preferred embodiment, the recovered supernatant has a rVWF specific ristocetin cofactor activity of at least 50 mU/μg rVWF. In a more preferred embodiment, the recovered supernatant has a rVWF specific ristocetin cofactor activity of at least 70 mU/μg rVWF.

In one embodiment of the method described above, the copper concentration and $NH_4^+$ concentration of the cell culture is maintained at a concentration according to any one of variations 1 to 440, as set forth in Table 1 for at least 9 weeks. In a preferred embodiment, the recovered supernatant has a rVWF specific ristocetin cofactor activity of at least 50 mU/μg rVWF. In a more preferred embodiment, the recovered supernatant has a rVWF specific ristocetin cofactor activity of at least 70 mU/μg rVWF.

In one embodiment, the present invention provides a method for producing a recombinant Von Willebrand Factor (rVWF) composition, the method comprising the steps of: (a) providing a basal cell culture media; (b) supplementing the basal cell culture media with copper to provide a final copper concentration of at least 2.0 μg/L; (c) providing one or more cells comprising a nucleic acid encoding a rVWF protein; (d) culturing the one or more cells in the copper supplemented cell culture media such that rVWF is expressed and excreted from the cells into a culture supernatant; (e) monitoring the ammonium concentration of the culture supernatant; and (f) recovering at least a portion of the culture supernatant, wherein culture supernatant comprising an ammonium concentration of more than 10 mM is not used for producing the rVWF composition, and further wherein the recovered supernatant has a rVWF specific ristocetin cofactor activity of at least 30 mU/μg rVWF. In certain embodiments, the final copper concentration of the supplemented basal culture media is at least 2.4 μg/L, 3 μg/L, 4 μg/L, 5 μg/L, 6 μg/L, 7 μg/L, 8 μg/L, 9 μg/L, 10 μg/L, 15 μg/L, 20 μg/L, or higher. In other embodiments, the final copper concentration of the supplemented basal culture media is between 2-20 μg/L, 2-10 μg/L, 3-8 μg/L, or 4-6 μg/L. In a preferred embodiment, the recovered supernatant has a rVWF specific ristocetin cofactor activity of at least 50 mU/μg rVWF. In a more preferred embodiment, the recovered supernatant has a rVWF specific ristocetin cofactor activity of at least 70 mU/μg rVWF.

In one embodiment of the method described above, culture supernatant comprising an ammonium concentration of more than 6 mM is not used for producing the rVWF composition. In certain embodiments, the final copper concentration of the supplemented basal culture media is at least 2.4 μg/L, 3 μg/L, 4 μg/L, 5 μg/L, 6 μg/L, 7 μg/L, 8 μg/L, 9 μg/L, 10 μg/L, 15 μg/L, 20 μg/L, or higher. In other embodiments, the final copper concentration of the supplemented basal culture media is between 2-20 μg/L, 2-10 μg/L, 3-8 μg/L, or 4-6 μg/L. In a preferred embodiment, the recovered supernatant has a rVWF specific ristocetin cofactor activity of at least 50 mU/μg rVWF. In a more preferred embodiment, the recovered supernatant has a rVWF specific ristocetin cofactor activity of at least 70 mU/μg rVWF.

In one embodiment of the method described above, culture supernatant comprising an ammonium concentration of more than 5 mM is not used for producing the rVWF composition. In certain embodiments, the final copper concentration of the supplemented basal culture media is at least 2.4 μg/L, 3 μg/L, 4 μg/L, 5 μg/L, 6 μg/L, 7 μg/L, 8 μg/L, 9 μg/L, 10 μg/L, 15 μg/L, 20 μg/L, or higher. In other embodiments, the final copper concentration of the supplemented basal culture media is between 2-20 μg/L, 2-10 μg/L, 3-8 μg/L, or 4-6 μg/L. In a preferred embodiment, the recovered supernatant has a rVWF specific ristocetin cofactor activity of at least 50 mU/μg rVWF. In a more preferred embodiment, the recovered supernatant has a rVWF specific ristocetin cofactor activity of at least 70 mU/μg rVWF.

In one embodiment of the method described above, culture supernatant comprising an ammonium concentration of more than 4 mM is not used for producing the rVWF composition. In certain embodiments, the final copper concentration of the supplemented basal culture media is at least 2.4 μg/L, 3 μg/L, 4 μg/L, 5 μg/L, 6 μg/L, 7 μg/L, 8 μg/L, 9 μg/L, 10 μg/L, 15 μg/L, 20 μg/L, or higher. In other embodiments, the final copper concentration of the supplemented basal culture media is between 2-20 μg/L, 2-10 μg/L, 3-8 μg/L, or 4-6 μg/L. In a preferred embodiment, the recovered supernatant has a rVWF specific ristocetin cofactor activity of at least 50 mU/μg rVWF. In a more preferred embodiment, the recovered supernatant has a rVWF specific ristocetin cofactor activity of at least 70 mU/μg rVWF.

Recombinant vWF can be produced by expression in a suitable eukaryotic host system. Examples of eukaryotic cells include, without limitation, mammalian cells, such as CHO, COS, HEK 293, BHK, SK-Hep, and HepG2; insect cells, e.g., SF9 cells, SF21 cells, S2 cells, and High Five cells; and yeast cells, e.g., *Saccharomyces* or *Schizosaccharomyces* cells. In one embodiment, the vWF can be expressed in yeast cells, insect cells, avian cells, mammalian cells, and the like. For example, in a human cell line, a hamster cell line, or a murine cell line. In one particular embodiment, the cell line is a CHO, BHK, or HEK cell line. Typically, mammalian cells, e.g., CHO cells from a continuous cell line, can be used to express the vWF of the present invention.

In certain embodiments, the nucleic acid sequence comprising a sequence coding for vWF can be a vector. The vector can be delivered by a virus or can be a plasmid. The nucleic acid sequence coding for the protein can be a specific gene or a biologically functional part thereof. In one embodiment, the protein is at least a biologically active part of vWF.

A wide variety of vectors can be used for the expression of the vWF and can be selected from eukaryotic expression vectors. Examples of vectors for eukaryotic expression include: (i) for expression in yeast, vectors such as pAO, pPIC, pYES, pMET, using promoters such as AOX1, GAP, GALL, AUG1, etc; (ii) for expression in insect cells, vectors such as pMT, pAc5, pIB, pMIB, pBAC, etc., using promoters such as PH, p10, MT, Ac5, OpIE2, gp64, polh, etc., and (iii) for expression in mammalian cells, vectors such as pSVL, pCMV, pRc/RSV, pcDNA3, pBPV, etc., and vectors derived from viral systems such as vaccinia virus, adeno-associated viruses, herpes viruses, retroviruses, etc., using promoters such as CMV, SV40, EF-1, UbC, RSV, ADV, BPV, and β-actin. An exemplary vector for expressing rVWF is described by Kaufman et al. (Mol Cell Biol. 1989 March; 9(3):1233-42), the content of which is hereby incorporated by reference in its entirety for all purposes.

In some embodiments of the present invention, the nucleic acid sequence further comprises other sequences suitable for a controlled expression of a protein such as promoter sequences, enhancers, TATA boxes, transcription initiation sites, polylinkers, restriction sites, poly-A-sequences, protein processing sequences, selection markers, and the like which are generally known to a person of ordinary skill in the art.

In addition to cell culture media comprising an increased copper concentration, the cell culture conditions of the present invention can include an ammonium concentration of less than about 25 mM throughout an entire upstream process in culture systems. In one embodiment, the cell culture conditions include an ammonium concentration of less than about 25 mM, in another embodiment less than about 20 mM, in yet another embodiment less than about 15 mM, in yet another embodiment less than about 10 mM, and in a further embodiment less than about 5 mM.

In some embodiments, the ammonium concentrations of the present invention are kept constant throughout the entire upstream process of the cell culture system. The cells used according to the present invention can be cultivated, e.g., by methods that are modified as compared to conventional batch-cultivation and feed-batch-cultivation, each of which are generally known in the field. However, such conventional techniques can produce high concentrations of ammonium at the end of the culture. The methods of the present invention overcome this problem by employing production systems that can provide a continuous supply of culture media through techniques such as, e.g., perfusion or chemostat cultures. Following culture of the host cells, the vWF can be recovered from the spent medium using standard methodologies, such as ultrafiltration or centrifugation. If desired, the vWF can be purified by, e.g., ion exchange and/or size exclusion chromatography and the like.

A continuous culture (e.g., a perfusion or chemostat culture) can be a suspension culture that is continuously supplied with nutrients by the inflow of fresh medium, wherein the culture volume is usually constant. Similarly, continuous fermentation can refer to a process in which cells or microorganisms are maintained in culture in the exponential growth phase by the continuous addition of fresh medium that is exactly balanced by the removal of cell suspension from the bioreactor. Furthermore, a stirred-tank reactor system can be used for suspension, perfusion, chemostatic, and/or microcarrier cultures. Generally, the stirred-tank reactor system can be operated as any conventional stirred-tank reactor with any type of agitator such as a Rushton, hydrofoil, pitched blade, or marine.

C. Methods of Producing Recombinant ADAMTS13 (A13)

In another aspect, the present invention further relates to methods for producing rA13 under cell culture conditions comprising a cell culture medium having an increased copper concentration. In certain embodiments, the culture also comprises a low ammonium concentration.

In one embodiment, the present invention provides a method for producing a recombinant ADAMTS13 (rA13) composition, the method comprising the steps of: (a) providing a basal cell culture media; (b) supplementing the basal cell culture media with copper to provide a final copper concentration of at least 1.0 µg/L; (c) providing one or more cells comprising a nucleic acid encoding a rA13 protein; (d) culturing the one or more cells in the copper supplemented cell culture media such that rA13 is expressed and excreted from the cells into a culture supernatant; and (e) recovering at least a portion of the culture supernatant, wherein at least 1500 Units FRETS-VWF73 activity per liter supplemented basal cell culture media per day (i.e., 1500 Units FRETS-VWF73 activity per day per liter cell culture; P FRETS) is present in the recovered culture supernatant. In certain embodiments, the final copper concentration of the supplemented basal culture media is at least 2 µg/L, 3 µg/L, 4 µg/L, 5 µg/L, 6 µg/L, or higher. In other embodiments, the final copper concentration of the supplemented basal culture media is between 1-6 µg/L, 2-5 µg/L, 2-4 µg/L, or 3-4 µg/L. In a preferred embodiment, at least 2000 Units FRETS-VWF73 activity per liter supplemented basal cell culture media per day is present in the recovered culture supernatant. In a more preferred embodiment, at least 2500 Units FRETS-VWF73 activity per liter supplemented basal cell culture media per day is present in the recovered culture supernatant. In a most preferred embodiment, at least 3000 Units FRETS-VWF73 activity per liter supplemented basal cell culture media per day is present in the recovered culture supernatant. In certain embodiments, the methods provide sustainably improved volumetric FRETS-VWF73 productivity (P FRETS). For example, in certain embodiments, at least 1500 Units FRETS-VWF73 activity per liter supplemented basal cell culture media is recovered daily for at least 7 days, or at least 14, 21, 28, 35, 42, 49, 56, 63, 70, or more days. In a preferred embodiment, at least 2000 Units FRETS-VWF73 activity per liter supplemented basal cell culture media is recovered daily for at least 7 days, or at least 14, 21, 28, 35, 42, 49, 56, 63, 70, or more days. In a more preferred embodiment, at least 2500 Units FRETS-VWF73 activity per liter supplemented basal cell culture media is recovered daily for at least 7 days, or at least 14, 21, 28, 35, 42, 49, 56, 63, 70, or more days. In a most preferred embodiment, at least 3000 Units FRETS-VWF73 activity per liter supplemented basal cell culture media is recovered daily for at least 7 days, or at least 14, 21, 28, 35, 42, 49, 56, 63, 70, or more days. In a specific embodiment, the cell density of the continuous cell culture for production of rA13 is maintained at a concentration of no more than $4.0 \times 10^6$ cells/mL for an extended period. In other specific embodiments, the cell density is maintained at no more than $3.5 \times 10^6$ cells/mL, $3.0 \times 10^6$ cells/mL, $2.5 \times 10^6$ cells/mL, $2.0 \times 10^6$ cells/mL, $1.5 \times 10^6$ cells/mL, $1.0 \times 10^6$ cells/mL, or less. In one embodiment, the cell density is maintained at between $3.0 \times 10^6$ cells/mL and $4.0 \times 10^6$ cells/mL.

In one embodiment of the methods described above, the recovered supernatant has at least 4 Units FRETS-VWF73 activity per mL supernatant (FRETS). In a preferred embodiment, the recovered supernatant has at least 6 Units FRETS-VWF73 activity per mL supernatant. In a more preferred embodiment, the recovered supernatant has at least 8 Units FRETS-VWF73 activity per mL supernatant. In a most preferred embodiment, the recovered supernatant has at least 10 Units FRETS-VWF73 activity per mL supernatant. In certain embodiments, the methods provide sustainably improved FRETS production. For example, in certain embodiments, supernatant having at least 4 Units FRETS-VWF73 activity per mL are recovered daily for at least 7 days, or at least 14, 21, 28, 35, 42, 49, 56, 63, 70, or more days. In a preferred embodiment, supernatant having at least 6 Units FRETS-VWF73 activity per mL are recovered daily for at least 7 days, or at least 14, 21, 28, 35, 42, 49, 56, 63, 70, or more days. In a more preferred embodiment, supernatant having at least 8 Units FRETS-VWF73 activity per mL are recovered daily for at least 7 days, or at least 14, 21, 28, 35, 42, 49, 56, 63, 70, or more days. In a most preferred embodiment, supernatant having at least 10 Units FRETS-VWF73 activity per mL are recovered daily for at least 7 days, or at least 14, 21, 28, 35, 42, 49, 56, 63, 70, or more days.

In one embodiment of the methods described above, the cell culture results in the production of at least 800 mU of FRETS-VWF73 activity per $10^6$ cells present in the culture per day (i.e., q FRETS). In a preferred embodiment, the cell culture results in the production of at least 1 U of FRETS-VWF73 activity per $10^6$ cells present in the culture per day. In a more preferred embodiment, the cell culture results in the production of at least 1.2 U of FRETS-VWF73 activity per $10^6$ cells present in the culture per day. In a most preferred embodiment, the cell culture results in the production of at least 1.4 U of FRETS-VWF73 activity per $10^6$ cells present in the culture per day. In certain embodiments, the methods provide sustainably improved cell-specific FRETS-VWF73 productivity (q FRETS). For example, in certain embodiments, the cell culture results in the production of at least 800 mU of FRETS-VWF73 activity per $10^6$ cells present in the culture daily for at least 7 days, or at least 14, 21, 28, 35, 42, 49, 56, 63, 70, or more days. In a preferred embodiment, the cell culture results in the production of at least 1 U of FRETS-VWF73 activity per $10^6$ cells present in the culture daily for at least 7 days, or at least 14, 21, 28, 35, 42, 49, 56, 63, 70, or more days. In a more preferred embodiment, the cell culture results in the production of at least 1.2 U of FRETS-VWF73 activity per $10^6$ cells present in the culture daily for at least 7 days, or at least 14, 21, 28, 35, 42, 49, 56, 63, 70, or more days. In a most preferred embodiment, the cell culture results in the production of at least 1.4 U of FRETS-VWF73 activity per $10^6$ cells present in the culture daily for at least 7 days, or at least 14, 21, 28, 35, 42, 49, 56, 63, 70, or more days.

In one embodiment of the methods described above, the cell culture results in the production of at least 1 mg rA13, as measured by ELISA, per liter culture per day (P ELISA). In a preferred embodiment, the cell culture results in the production of at least 1.5 mg rA13, as measured by ELISA, per liter culture per day. In a more preferred embodiment, the cell culture results in the production of at least 2 mg rA13, as measured by ELISA, per liter culture per day. In certain embodiments, the methods provide sustainably improved rA13 production. For example, in certain embodiments, the cell culture results in the production of at least 1 mg rA13, as measured by ELISA, per liter culture daily for at least 7 days, or at least 14, 21, 28, 35, 42, 49, 56, 63, 70, or more days. In a preferred embodiment, the cell culture results in the production of at least 1.5 mg rA13, as measured by ELISA, per liter culture daily for at least 7 days, or at least 14, 21, 28, 35, 42, 49, 56, 63, 70, or more days. In a more preferred embodiment, the cell culture results in the production of at least 2 mg rA13, as measured by ELISA, per liter culture daily for at least 7 days, or at least 14, 21, 28, 35, 42, 49, 56, 63, 70, or more days.

In one embodiment of the methods described above, the cell culture results in the production of at least 0.5 µg rA13, as measured by ELISA, per $10^6$ cells present in the culture per day (i.e., q ELISA). In a preferred embodiment, the cell culture results in the production of at least 0.7 µg rA13, as measured by ELISA, per $10^6$ cells present in the culture per day. In a more preferred embodiment, the cell culture results in the production of at least 0.9 µg rA13, as measured by ELISA, per $10^6$ cells present in the culture per day. In certain embodiments, the methods provide sustainably improved q ELISA production. For example, in certain embodiments, the cell culture results in the production of at least 0.5 µg rA13, as measured by ELISA, per $10^6$ cells present in the culture daily for at least 7 days, or at least 14, 21, 28, 35, 42, 49, 56, 63, 70, or more days. In a preferred embodiment, the cell culture results in the production of at least 0.7 µg rA13, as measured by ELISA, per $10^6$ cells present in the culture daily for at least 7 days, or at least 14, 21, 28, 35, 42, 49, 56, 63, 70, or more days. In a more preferred embodiment, the cell culture results in the production of at least 0.9 µg rA13, as measured by ELISA, per $10^6$ cells present in the culture daily for at least 7 days, or at least 14, 21, 28, 35, 42, 49, 56, 63, 70, or more days.

In one embodiment of the methods described above, the recovered supernatant has at least 3 µg rA13, as measured by ELISA, per mL supernatant. In a preferred embodiment, the recovered supernatant has at least 4 µg rA13, as measured by ELISA, per mL supernatant. In a more preferred embodiment, the recovered supernatant has at least 5 µg rA13, as measured by ELISA, per mL supernatant. In a most preferred embodiment, the recovered supernatant has at least 6 µg rA13, as measured by ELISA, per mL supernatant. In certain embodiments, the methods provide sustainably improved rA13 production. For example, in certain embodiments, supernatant having at least 3 µg rA13 per mL are recovered daily for at least 7 days, or at least 14, 21, 28, 35, 42, 49, 56, 63, 70, or more days. In a preferred embodiment, supernatant having at least 4 µg rA13 per mL are recovered daily for at least 7 days, or at least 14, 21, 28, 35, 42, 49, 56, 63, 70, or more days. In a more preferred embodiment, supernatant having at least 5 µg rA13 per mL are recovered daily for at least 7 days, or at least 14, 21, 28, 35, 42, 49, 56, 63, 70, or more days. In a most preferred embodiment, supernatant having at least 6 µg rA13 per mL are recovered daily for at least 7 days, or at least 14, 21, 28, 35, 42, 49, 56, 63, 70, or more days.

In one embodiment of the methods described above, the cell culture solution further comprises an ammonium concentration of less than 10 mM. In another specific embodiment, the ammonium concentration of the cell culture is maintained at an ammonium concentration of no more than 10 mM for at least 7 days. In a preferred embodiment, the cell culture solution comprises an ammonium concentration of no more than 5 mM. In another specific embodiment, the ammonium concentration of the cell culture is maintained at an ammonium concentration of no more than 5 mM for at least 7 days. In a preferred embodiment, the cell culture solution comprises an ammonium concentration of no more than 4 mM. In another specific embodiment, the ammonium concentration of the cell culture is maintained at an ammonium concentration of no more than 4 mM for at least 7 days. In yet other embodiments, the cell culture solution comprises an ammonium concentration of no more than 10 mM, or no more than 9 mM, 8 mM, 7 mM, 6 mM, 5 mM, 4 mM, 3 mM, 2 mM, 1 mM, or less. In yet another embodiment, the ammonium concentration of the cell culture is maintained at a low level for the duration of the process (i.e., for the entire time the culture is being used to produce rA13). In a particular embodiment, the culture solution has a copper and ammonium concentration according to any one of variations 1 to 440, as provided in Table 1.

In one embodiment, the present invention provides a method for producing a recombinant ADAMTS13 (rA13) composition, the method comprising the steps of: (a) providing a basal cell culture media; (b) supplementing the basal cell culture media with copper and zinc; (c) providing one or more cells comprising a nucleic acid encoding a rA13 protein; (d) culturing the one or more cells in the copper supplemented cell culture media such that rA13 is expressed and excreted from the cells into a culture supernatant; and (e) recovering at least a portion of the culture supernatant, wherein at least 1500 Units FRETS-VWF73 activity per liter supplemented basal cell culture media per day is present in the recovered culture supernatant. In one embodiment, the culture medium contains at least 1 µg/L copper and at least 2 µM zinc. In other embodiments, the media contains at least 2 µg/L copper or at least 4 µg/L copper. In one embodiment wherein the media is supplemented with copper, the culture medium also contains at least at or about 5 µM zinc. In one embodiment, the culture medium also contains at or about between 2 µM and 12 µM zinc. In another embodiment, the culture medium also contains at or about between 5 µM and 12 µM zinc. In yet other embodiments, the culture medium also may contain at least at or about 2 µM, or at least at or about 3 µM, 4 µM, 5 µM, 6 µM, 7 µM, 8 µM, 9 µM, 10 µM, 11 µM, 12 µM, 13 µM, 14 µM, 15 µM, 20 µM, 25 µM, 30 µM, or more zinc. In one embodiment, the culture medium contains a copper and zinc concentration according to any one of variations 441 to 880, as set forth in Table 2. In a preferred embodiment, at least 2000 Units FRETS-VWF73 activity per liter supplemented basal cell culture media per day is present in the recovered culture supernatant. In a more preferred embodiment, at least 2500 Units FRETS-VWF73 activity per liter supplemented basal cell culture media per day is present in the recovered culture supernatant. In a most preferred embodiment, at least 3000 Units FRETS-VWF73 activity per liter supplemented basal cell culture media per day is present in the recovered culture supernatant.

In one embodiment, the present invention provides a method for producing a recombinant ADAMTS13 (rA13) composition, the method comprising the steps of: (a) providing a basal cell culture media; (b) supplementing the basal cell culture media with copper and calcium; (c) providing one or more cells comprising a nucleic acid encoding a rA13 protein; (d) culturing the one or more cells in the copper supplemented cell culture media such that rA13 is expressed and excreted from the cells into a culture supernatant; and (e) recovering at least a portion of the culture supernatant, wherein at least 1500 Units FRETS-VWF73 activity per liter supplemented basal cell culture media per day is present in the recovered culture supernatant. In one embodiment, the culture medium contains at least 1 µg/L copper and at least 0.5 mM calcium. In other embodiments, the media contains at least 2 µg/L copper or at least 4 µg/L copper. In another embodiment wherein the media is supplemented with copper, the culture medium also contains at least 1.5 mM calcium. In one embodiment, the culture medium contains at or about between 0.5 mM and 1.5 mM calcium. In yet other embodiments, the culture medium may contain at least at or about 0.5 mM, or at least at or about 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium. In one embodiment, the culture medium contains a copper and calcium concentration according to any one of variations 881 to 1320, as set forth in Table 3. In a preferred embodiment, at least 2000 Units FRETS-VWF73 activity per liter supplemented basal cell culture media per day is present in the recovered culture supernatant. In a more preferred embodiment, at least 2500 Units FRETS-VWF73 activity per liter supplemented basal cell culture media per day is present in the recovered culture supernatant. In a most preferred embodiment, at least 3000 Units FRETS-VWF73 activity per liter supplemented basal cell culture media per day is present in the recovered culture supernatant.

In one embodiment, the present invention provides a method for producing a recombinant ADAMTS13 (rA13) composition, the method comprising the steps of: (a) providing a basal cell culture media; (b) supplementing the basal cell culture media with copper, zinc, and calcium; (c) providing one or more cells comprising a nucleic acid encoding a rA13 protein; (d) culturing the one or more cells in the copper supplemented cell culture media such that rA13 is expressed and excreted from the cells into a culture supernatant; and (e) recovering at least a portion of the culture supernatant, wherein at least 1500 Units FRETS-VWF73 activity per liter supplemented basal cell culture media per day is present in the recovered culture supernatant. In one embodiment, the culture medium has a calcium concentration of at least 0.5 mM and a copper and zinc concentration according to any one of variations 441 to 880, as set forth in Table 2. In another specific embodiment, the culture medium has a calcium concentration of at least 1.5 mM and a copper and zinc concentration according to any one of variations 441 to 880, as set forth in Table 2. In another specific embodiment, the culture medium has a calcium concentration between 0.5 mM and 1.5 mM and a copper and zinc concentration according to any one of variations 441 to 880, as set forth in Table 2. In yet other embodiments, the culture medium has a calcium concentration of at least 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more, and a copper and zinc concentration according to any one of variations 441 to 880, as set forth in Table 2. In a preferred embodiment, at least 2000 Units FRETS-VWF73 activity per liter supplemented basal cell culture media per day is present in the recovered culture supernatant. In a more preferred embodiment, at least 2500 Units FRETS-VWF73 activity per liter supplemented basal cell culture media per day is present in the recovered culture supernatant. In a most preferred embodiment, at least 3000 Units FRETS-VWF73 activity per liter supplemented basal cell culture media per day is present in the recovered culture supernatant.

In one embodiment, the present invention provides a method for producing a recombinant ADAMTS13 (rA13) composition, the method comprising the steps of: (a) providing a basal cell culture media; (b) supplementing the basal cell culture media with copper and nicotinamide; (c) providing one or more cells comprising a nucleic acid encoding a rA13 protein; (d) culturing the one or more cells in the copper supplemented cell culture media such that rA13 is expressed and excreted from the cells into a culture supernatant; and (e) recovering at least a portion of the culture supernatant, wherein at least 1500 Units FRETS-VWF73 activity per liter supplemented basal cell culture media per day is present in the recovered culture supernatant. In one embodiment, the culture medium contains at least 1 µg/L copper and at least 2 mg/L nicotinamide (vitamin B3). In other embodiments, the media contains at least 2 µg/L copper or at least 4 µg/L copper. In another embodiment wherein the media is supplemented with copper, the culture medium also contains at least 7 mg/L nicotinamide (vitamin B3). In one embodiment, the culture medium contains at or about between 2 mg/L and 10 mg/L nicotinamide (vitamin B3). In yet other embodiments, the culture medium may contain at least at or about 2 mg/L, 3 mg/L, 4 mg/L, 5 mg/L, 6 mg/L, 7 mg/L, 8 mg/L, 9 mg/L, 10 mg/L, 15 mg/L, 20 mg/L, or higher concentrations of nicotinamide (vitamin B3). In one embodiment, the culture medium contains a copper and nicotinamide concentration according to any one of variations 1321 to 1760, as set forth in Table 4. In a preferred embodiment, at least 2000 Units FRETS-VWF73 activity per liter supplemented basal cell culture media per day is present in the recovered culture supernatant. In a more preferred embodiment, at least 2500 Units FRETS-VWF73 activity per liter supplemented basal cell culture media per day is present in the recovered culture supernatant. In a most preferred embodiment, at least 3000 Units FRETS-VWF73 activity per liter supplemented basal cell culture media per day is present in the recovered culture supernatant.

In one embodiment, the present invention provides a method for producing a recombinant ADAMTS13 (rA13) composition, the method comprising the steps of: (a) providing a basal cell culture media; (b) supplementing the basal cell culture media with copper, zinc, and nicotinamide; (c) providing one or more cells comprising a nucleic acid encoding a rA13 protein; (d) culturing the one or more cells in the copper supplemented cell culture media such that rA13 is expressed and excreted from the cells into a culture supernatant; and (e) recovering at least a portion of the culture supernatant, wherein at least 1500 Units FRETS-VWF73 activity per liter supplemented basal cell culture media per day is present in the recovered culture supernatant. In one embodiment, the cell culture medium has a nicotinamide concentration of at least 2 mg/mL and a copper and zinc concentration according to any one of variations 441 to 880, as set forth in Table 2. In another specific embodiment, the culture medium has a nicotinamide concentration of at least 7 mg/mL mM and a copper and zinc concentration according to any one of variations 441 to 880, as set forth in Table 2. In another specific embodiment, the culture medium has a nicotinamide concentration between 2 mg/mL and 10 mg/mL and a copper and zinc concentration according to any one of variations 441 to 880, as set forth in Table 2. In yet other embodiments, the culture medium has a nicotinamide concentration of at least 2 mg/mL, 3 mg/mL, 4 mg/mL, 5 mg/mL, 6 mg/mL, 7 mg/mL, 8 mg/mL, 9 mg/mL, 10 mg/mL, 11 mg/mL, 12 mg/mL, 13 mg/mL, 14 mg/mL, 15 mg/mL, or more, and a copper and zinc concentration according to any one of variations 441 to 880, as set forth in Table 2. In a preferred embodiment, at least 2000 Units FRETS-VWF73 activity per liter supplemented basal cell culture media per day is present in the recovered culture supernatant. In a more preferred embodiment, at least 2500 Units FRETS-VWF73 activity per liter supplemented basal cell culture media per day is present in the recovered culture supernatant. In a most preferred embodiment, at least 3000 Units FRETS-VWF73 activity per liter supplemented basal cell culture media per day is present in the recovered culture supernatant.

In one embodiment, the present invention provides a method for producing a recombinant ADAMTS13 (rA13) composition, the method comprising the steps of: (a) providing a basal cell culture media; (b) supplementing the basal cell culture media with copper, calcium, and nicotinamide; (c) providing one or more cells comprising a nucleic acid encoding a rA13 protein; (d) culturing the one or more cells in the copper supplemented cell culture media such that rA13 is expressed and excreted from the cells into a culture supernatant; and (e) recovering at least a portion of the culture supernatant, wherein at least 1500 Units FRETS-VWF73 activity per liter supplemented basal cell culture media per day is present in the recovered culture supernatant. In one embodiment, the cell culture medium has a nicotinamide concentration of at least 2 mg/mL and a copper and calcium concentration according to any one of variations 881 to 1320, as set forth in Table 3. In another specific embodiment, the culture medium has a nicotinamide concentration of at least 7 mg/mL mM and a copper and calcium concentration according to any one of variations 881 to 1320, as set forth in Table 3. In another specific embodiment, the culture medium has a nicotinamide concentration between 2 mg/mL and 10 mg/mL and a copper and calcium concentration according to any one of variations 881 to 1320, as set forth in Table 3. In yet other embodiments, the culture medium has a nicotinamide concentration of at least 2 mg/mL, 3 mg/mL, 4 mg/mL, 5 mg/mL, 6 mg/mL, 7 mg/mL, 8 mg/mL, 9 mg/mL, 10 mg/mL, 11 mg/mL, 12 mg/mL, 13 mg/mL, 14 mg/mL, 15 mg/mL, or more, and a copper and calcium concentration according to any one of variations 881 to 1320, as set forth in Table 3. In a preferred embodiment, at least 2000 Units FRETS-VWF73 activity per liter supplemented basal cell culture media per day is present in the recovered culture supernatant. In a more preferred embodiment, at least 2500 Units FRETS-VWF73 activity per liter supplemented basal cell culture media per day is present in the recovered culture supernatant. In a most preferred embodiment, at least 3000 Units FRETS-VWF73 activity per liter supplemented basal cell culture media per day is present in the recovered culture supernatant.

Recombinant ADAMTS proteins can be produced by expression in any suitable prokaryotic or eukaryotic host system. Examples of eukaryotic cells include, without limitation, mammalian cells, such as CHO, COS, HEK 293, BHK, SK-Hep, and HepG2; insect cells, for example SF9 cells, SF21 cells, S2 cells, and High Five cells; and yeast cells, for example *Saccharomyces* or *Schizosaccharomyces* cells. In one embodiment, the ADAMTS proteins can be expressed in bacterial cells, yeast cells, insect cells, avian cells, mammalian cells, and the like. For example, in a human cell line, a hamster cell line, or a murine cell line. In one particular embodiment, the cell line is a CHO, BHK, or HEK cell line. In a preferred embodiment, the cell line is a CHO cell line. In a specific embodiment, CHO clones capable of stably expressing rA13 are prepared by co-transfecting a CHO cell with coding sequences for rA13 and a dihydrofolate reductase (e.g., a murine dhfr gene) and selecting for growth in the presence of increasing levels of methotrexate.

In one embodiment, the cells may be any mammalian cell that can be cultured, preferably in a manufacturing process (i.e., at least 10 liter, preferrably at least 100 liters), to produce a desired ADAMTS protein such as ADAMTS13. Examples include the monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); baby hamster kidney cells (BHK, ATCC CCL 10); Chinese hamster ovary cells/−DHFR, such as the DUKX-B11 subclone (CHO, Uriaub and Chasin, *Proc. Natl. Acad. Sci. USA*, 77:4216 (1980)); mouse Sertoli cells (TM4, Mather, *Biol. Reprod*, 23:243-251 (1980)); monkey kidney cells (CV1 ATCC CCL 70); African green monkey kidney cells (VERO-76, ATCC CRL-1587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.*, 383:44-68 (1982)); MRC 5 cells; FS4 cells; and the human hepatoma line (Hep G2). Preferably, the cell line is a rodent cell line, especially a hamster cell line such as CHO or BHK.

A wide variety of vectors can be used for the expression of an ADAMTS protein (e.g., ADAMTS13) and can be selected from eukaryotic and prokaryotic expression vectors. In certain embodiments, a plasmid vector is contemplated for use in expressing an ADAMTS protein (e.g., ADAMTS13). In general, plasmid vectors containing replicon and control sequences which are derived from species compatible with the host cell are used in connection with these hosts. The vector can carry a replication site, as well as marking sequences which are capable of providing phenotypic selection in transformed cells. The plasmid will comprise a nucleotide sequence encoding an ADAMTS protein (e.g., ADAMTS13) operable linked to one or more control sequences, for example, a promoter.

A preferred method of preparing stable CHO cell clones expressing a recombinant ADAMTS protein is as follows. A DHFR deficient CHO cell line DUKX-B11 is transfected with a DHFR expression vector to allow for expression of the relevant recombinant protein. An exemplary method is described by Plaimauer et al. (Blood. 2002 Nov. 15; 100(10): 3626-32. Epub 2002 Jul. 12), the content of which is hereby incorporated by reference in its entirety for all purposes. Selection is carried out by growth in Hypoxanthine/Thymidine (HT) free media and amplification of the relevant region coding for expression of the recombinant ADAMTS protein and DHFR gene is achieved by propagation of the cells in increasing concentrations of methotrexate. Where appropriate, CHO cell lines may be adapted for growth in serum and/or protein free medium, essentially as described in U.S. Pat. No. 6,100,061 (Reiter et al., Immuno Aktiengesellschaft).

In another preferred embodiment, stable HEK293 cells are prepared by transfecting with a construct containing a hygromycin selectable marker and selecting transformants by antibiotic resistance.

The ability of certain viruses to infect cells or enter cells via receptor-mediated endocytosis, and to integrate into host cell genome and express viral genes stably and efficiently have made them attractive candidates for the transfer of foreign nucleic acids into cells (e.g., mammalian cells). Accordingly, in certain embodiments, a viral vector is used to introduce a nucleotide sequence encoding an ADAMTS protein (e.g., ADAMTS13) into a host cell for expression. The viral vector will comprise a nucleotide sequence encoding an ADAMTS protein (e.g., ADAMTS13) operable linked to one or more control sequences, for example, a promoter. Alternatively, the viral vector may not contain a control sequence and will instead rely on a control sequence within the host cell to drive expression of the ADAMTS protein. Non-limiting examples of virus vectors that may be used to deliver a nucleic acid include Adenoviral vectors, AAV vectors, and Retroviral vectors.

In one embodiment, an Adenovirus expression vector include those constructs containing adenovirus sequences sufficient to support packaging of the construct and to ultimately express an ADAMTS construct that has been cloned therein. Adenoviral vectors allow for the introduction of foreign sequences up to 7 kb (Grunhaus et al., Seminar in Virology, 200(2):535-546, 1992)).

In another embodiment, an adeno-associated virus (AAV) can be used to introduce a nucleotide sequence encoding an ADAMTS protein (e.g., ADAMTS13) into a host cell for expression. AAV systems have been described previously and are generally well known in the art (Kelleher and Vos, *Biotechniques*, 17(6):1110-7, 1994; Cotten et al., *Proc Natl Acad Sci USA*, 89(13):6094-6098, 1992; Curiel, *Nat Immun*, 13(2-3):141-64, 1994; Muzyczka, *Curr Top Microbiol Immunol*, 158:97-129, 1992). Details concerning the generation and use of rAAV vectors are described, for example, in U.S. Pat. Nos. 5,139,941 and 4,797,368, each incorporated herein by reference in their entireties for all purposes.

In one embodiment, a retroviral expression vector can be used to introduce a nucleotide sequence encoding an ADAMTS protein (e.g., ADAMTS13) into a host cell for expression. These systems have been described previously and are generally well known in the art (Mann et al., Cell, 33:153-159, 1983; Nicolas and Rubinstein, In: Vectors: A survey of molecular cloning vectors and their uses, Rodriguez and Denhardt, eds., Stoneham: Butterworth, pp. 494-513, 1988; Temin, In: Gene Transfer, Kucherlapati (ed.), New York: Plenum Press, pp. 149-188, 1986). In a specific embodiment, the retroviral vector is a lentiviral vector (see, for example, Naldini et al., *Science*, 272(5259):263-267, 1996; Zufferey et al., *Nat Biotechnol*, 15(9):871-875, 1997; Blomer et al., *J. Virol.*, 71(9):6641-6649, 1997; U.S. Pat. Nos. 6,013,516 and 5,994,136).

Non-limiting examples of vectors for prokaryotic expression include plasmids such as pRSET, pET, pBAD, etc., wherein the promoters used in prokaryotic expression vectors include lac, trc, trp, recA, araBAD, etc. Examples of vectors for eukaryotic expression include: (i) for expression in yeast, vectors such as pAO, pPIC, pYES, pMET, using promoters such as AOX1, GAP, GAL1, AUG1, etc; (ii) for expression in insect cells, vectors such as pMT, pAc5, pIB, pMIB, pBAC, etc., using promoters such as PH, p10, MT, Ac5, OpIE2, gp64, polh, etc., and (iii) for expression in mammalian cells, vectors such as pSVL, pCMV, pRc/RSV, pcDNA3, pBPV, etc., and vectors derived form viral systems such as vaccinia virus, adeno-associated viruses, herpes viruses, retroviruses, etc., using promoters such as CMV, SV40, EF-1, UbC, RSV, ADV, BPV, and β-actin. An exemplary vector for expressing rA13 is described by Plaimauer et al. (Blood. 2002 Nov. 15; 100(10):3626-32. Epub 2002 Jul. 12), the content of which is hereby incorporated by reference in its entirety for all purposes.

In certain embodiments, the cell-culture methods of the invention may comprise the use of a microcarrier. The present invention provides, among other aspect, methods of large-scale ADAMTS protein expression. In some embodiments, the cell-cultures of the embodiments can be performed in large bioreactors under conditions suitable for providing high volume-specific culture surface areas to achieve high cell densities and protein expression. One means for providing such growth conditions is to use microcarriers for cell-culture in stirred tank bioreactors. In another embodiment, these growth requirements are met via the use of a suspension cell culture.

V. Specific Embodiments

A. Recombinant Von Willebrand Factor (rVWF)

Recombinant vWF can be expressed in mammalian cells, but the specific activity of the vWF can vary widely depending on the cell culture conditions and has not been shown to be comparable or equal to that of vWF isolated from blood plasma. The present invention is based in-part on the surprising result that cell culture media having at least 2.4 μg/L of copper provides an advantageous effect of promoting expression of high molecular weight vWF having a high specific activity. In particular, the high molecular weight, recombinant vWF of the present invention can include a highly multimeric form comprising about 14 to about 22 dimers and a specific Ristocetin activity of at least about 30 mU/μg. The cell culture processes according to the present invention also allow for maintaining low $NH_4^+$ levels (e.g., less than 10 mM) during the upstream process in cell culture systems, thereby reducing deleterious effects to post-translational modifications. It is believed that the present invention provides for the first time cell culture conditions comprising a medium having a suitable copper concentration in combination with appropriate levels of ammonium in the supernatant to express a highly multimeric vWF with a high specific activity.

In one aspect, the present invention relates to cell culture conditions for producing recombinant, high molecular weight vWF with a high specific activity. The cell culture conditions of the present invention can include, for example, a cell culture medium with an increased copper concentration and/or cell culture supernatant with a low ammonium ($NH_4^+$) concentration. The present invention also provides methods for cultivating cells in cell culture conditions to express a high molecular weight vWF with a high specific activity.

In one aspect, the present invention provides a cell culture solution for producing high molecular weight, recombinant vWF protein, the cell culture solution comprising: a cell culture medium comprising a copper concentration of at least about 2.4 μg/L; a cell culture supernatant comprising an ammonium concentration of less than 10 mM; and a plurality of cells expressing highly multimeric vWF protein, wherein the vWF protein comprises a specific Ristocetin activity of at least about 30 mU/μg.

In one specific embodiment of the cell cultures described above, the cell culture solution comprises a medium supplement comprising copper.

In one specific embodiment of the cell cultures described above, the medium supplement comprises a hydrolysate, optionally a soy hydrolysate.

In one specific embodiment of the cell cultures described above, the medium supplement comprises a copper salt, a copper chelate, or a combination thereof.

In one specific embodiment of the cell cultures described above, the copper salt is selected from the group consisting of copper sulfate, copper acetate, copper carbonate, copper chloride, copper hydroxide, copper nitrate, and copper oxide.

In one specific embodiment of the cell cultures described above, the copper concentration is at least about 4 μg/L.

In one specific embodiment of the cell cultures described above, the copper concentration is from about 2.4 μg/L to about 20 μg/L.

In one specific embodiment of the cell cultures described above, the vWF protein comprises about 14 to about 22 dimers.

In one aspect, the present invention provides a method of producing a high molecular weight, recombinant vWF protein, the method comprising the steps of: a) providing a culture of cells comprising a nucleic acid encoding recombinant vWF protein; b) expressing vWF protein in the cells under cell culture conditions comprising a cell culture medium comprising a copper concentration of at least about 2.4 μg/L and a cell culture supernatant comprising an ammonium concentration less than about 10 mM, wherein the vWF protein is highly multimeric vWF protein and comprises a specific Ristocetin activity of at least about 30 mU/μg.

In one specific embodiment of the methods described above, the cells are mammalian cells.

In one specific embodiment of the methods described above, the cells are from a continuous cell line.

In one specific embodiment of the methods described above, the cells are CHO cells.

In one specific embodiment of the methods described above, the copper concentration is at least about 4 μg/L.

In one specific embodiment of the methods described above, the copper concentration is from about 2.4 μg/L to about 20 μg/L.

In one specific embodiment of the methods described above, the recombinant vWF protein has a specific Ristocetin Cofactor activity of at least about 50 mU/μg.

In one specific embodiment of the methods described above, the recombinant vWF protein has a specific Ristocetin Cofactor activity from about 30 mU/μg to about 100 mU/μg.

In one specific embodiment of the methods described above, the recombinant vWF protein comprises about 14 to about 22 dimers.

In one aspect, the present invention provides a high molecular weight, recombinant vWF protein produced by a process, the process comprising the steps of: a) providing a culture of cells comprising a nucleic acid encoding recombinant vWF protein; and b) expressing vWF protein in the cells under cell culture conditions comprising a cell culture medium comprising a copper concentration of at least 2.4 μg/L and a cell culture supernatant comprising an ammonium concentration less than 10 mM, wherein the vWF protein is highly multimeric vWF protein and comprises a specific Ristocetin activity of at least about 30 mU/μg.

In one specific embodiment of the rVWF compositions described above, the recombinant vWF protein has a specific Ristocetin Cofactor activity of at least about 50 mU/μg.

In one specific embodiment of the rVWF compositions described above, the recombinant vWF protein has a specific Ristocetin Cofactor activity from about 30 mU/μg to about 100 mU/μg.

In one specific embodiment of the rVWF compositions described above, the recombinant vWF protein comprises about 14 to about 22 dimers.

In one aspect, the present invention provides a cell culture solution for producing high molecular weight, recombinant vWF protein, the cell culture solution comprising: a cell culture medium comprising a copper concentration of at least about 2.4 μg/L; a cell culture supernatant comprising an ammonium concentration of less than 10 mM; and a plurality of cells expressing highly multimeric vWF protein, wherein the vWF protein comprises about 14 to about 22 dimers and a specific Ristocetin activity of at least about 30 mU/μg.

In one aspect, the present invention relates to cell culture conditions for producing recombinant high molecular weight vWF that is in highly multimeric form with a high specific activity. The cell culture conditions of the present invention can include, for example, a cell culture medium with an increased copper concentration and cell culture supernatant with a low ammonium ($NH_4^+$) concentration. The present invention also provides methods for cultivating cells in cell culture conditions to express a high molecular weight vWF with a high specific activity.

In one aspect, the present invention includes a cell culture solution for producing high molecular weight, recombinant vWF, comprising a cell culture medium comprising a copper concentration of at least about 2.4 µg/L; a cell culture supernatant comprising an ammonium concentration of less than 10 mM; and a plurality of cells expressing highly multimeric vWF comprising about 14 to about 22 dimers and a specific Ristocetin activity of at least about 30 mU/µg. In one embodiment of the cell culture solutions described above, at least 10% of the rVWF is present in a high molecular weight VWF multimer of more than 10 dimers. In a specific embodiment, at least 15% of the rVWF is present in a high molecular weight VWF multimer of more than 10 dimers. In another specific embodiment, at least 20% of the rVWF is present in a high molecular weight VWF multimer of more than 10 dimers. In another specific embodiment, at least 25% of the rVWF is present in a high molecular weight VWF multimer of more than 10 dimers. In another specific embodiment, at least 30% of the rVWF is present in a high molecular weight VWF multimer of more than 10 dimers. In certain embodiments, the copper concentration can be at least about 4 µg/L or the copper concentration can range from about 2.4 µg/L to about 20 µg/L. In some embodiments, the cell culture media comprise a medium supplement comprising copper. In certain embodiments, the medium supplement can comprise a hydrolysate or a copper salt, copper chelate, or a combination thereof. In some embodiments, the copper salt can include copper sulfate, copper acetate, copper carbonate, copper chloride, copper hydroxide, copper nitrate, or copper oxide. In certain embodiments, the cells that can be from a continuous cell line and can include mammalian cells, such as CHO cells. In some embodiments, the recombinant vWF has a specific Ristocetin Cofactor activity of at least about 50 mU/µg, or the specific Ristocetin Cofactor activity can range from about 30 mU/µg to about 100 mU/µg.

In another aspect, the present invention includes a method of producing a high molecular weight, recombinant vWF, comprising a) providing a culture of cells; b) introducing a nucleic acid sequence coding for vWF; c) selecting the cells carrying the nucleic acid sequence; and, d) expressing vWF in the cells under cell culture conditions comprising a cell culture medium comprising a copper concentration of at least about 2.4 µg/L and a cell culture supernatant comprising an ammonium concentration less than about 10 mM, wherein the vWF is highly multimeric vWF comprising about 14 to about 22 dimers and a specific Ristocetin activity of at least about 30 mU/µg. In one embodiment of the cell culture supernatant described above, at least 10% of the rVWF is present in a high molecular weight VWF multimer of more than 10 dimers. In a specific embodiment, at least 15% of the rVWF is present in a high molecular weight VWF multimer of more than 10 dimers. In another specific embodiment, at least 20% of the rVWF is present in a high molecular weight VWF multimer of more than 10 dimers. In another specific embodiment, at least 25% of the rVWF is present in a high molecular weight VWF multimer of more than 10 dimers. In another specific embodiment, at least 30% of the rVWF is present in a high molecular weight VWF multimer of more than 10 dimers. In some embodiments, the cells that can be from a continuous cell line and can include mammalian cells, such as CHO cells. In certain embodiments, the copper concentration can be at least about 4 µg/L or the copper concentration can range from about 2.4 µg/L to about 20 µg/L. In some embodiments, the cell culture media comprise a medium supplement comprising copper. In certain embodiments, the medium supplement can comprise a hydrolysate or a copper salt, copper chelate, or a combination thereof. In some embodiments, the copper salt can include copper sulfate, copper acetate, copper carbonate, copper chloride, copper hydroxide, copper nitrate, or copper oxide. In some embodiments, the recombinant vWF has a specific Ristocetin Cofactor activity of at least about 50 mU/µg, or the specific Ristocetin Cofactor activity can range from about 30 mU/µg to about 100 mU/µg.

In yet another aspect, the present invention includes a high molecular weight, recombinant vWF produced by a process, comprising the steps of: a) providing a culture of cells; b) introducing a nucleic acid sequence coding for vWF; c) selecting the cells carrying the nucleic acid sequence; and, d) expressing vWF in the cells under cell culture conditions comprising a cell culture medium comprising a copper concentration of at least 2.4 µg/L and a cell culture supernatant comprising an ammonium concentration less than 10 mM, wherein the vWF is highly multimeric vWF comprising about 14 to about 22 dimers and a specific Ristocetin activity of at least about 30 mU/µg. In one embodiment of the cell culture supernatant described above, at least 10% of the rVWF is present in a high molecular weight VWF multimer of more than 10 dimers. In a specific embodiment, at least 15% of the rVWF is present in a high molecular weight VWF multimer of more than 10 dimers. In another specific embodiment, at least 20% of the rVWF is present in a high molecular weight VWF multimer of more than 10 dimers. In another specific embodiment, at least 25% of the rVWF is present in a high molecular weight VWF multimer of more than 10 dimers. In another specific embodiment, at least 30% of the rVWF is present in a high molecular weight VWF multimer of more than 10 dimers. In some embodiments, the cells that can be from a continuous cell line and can include mammalian cells, such as CHO cells. In certain embodiments, the copper concentration can be at least about 4 µg/L or the copper concentration can range from about 2.4 µg/L to about 20 µg/L. In some embodiments, the cell culture media comprise a medium supplement comprising copper. In certain embodiments, the medium supplement can comprise a hydrolysate or a copper salt, copper chelate, or a combination thereof. In some embodiments, the copper salt can include copper sulfate, copper acetate, copper carbonate, copper chloride, copper hydroxide, copper nitrate, or copper oxide. In some embodiments, the recombinant vWF has a specific Ristocetin Cofactor activity of at least about 50 mU/µg, or the specific Ristocetin Cofactor activity can range from about 30 mU/µg to about 100 mU/µg.

In one aspect, the present invention provides a composition comprising recombinant Von Willebrand Factor (rVWF) having a specific ristocetin cofactor activity of at least 30 mU/µg. In a preferred embodiment, the composition has a specific ristocetin cofactor activity of at least 40 mU/µg. In a more preferred embodiment, the composition has a specific ristocetin cofactor activity of at least 50 mU/µg. In a more preferred embodiment, the composition has a specific ristocetin cofactor activity of at least 60 mU/µg. In a more preferred embodiment, the composition has a specific ristocetin cofactor activity of at least 70 mU/µg. In yet a more preferred embodiment, the composition has a specific ristocetin cofactor activity of at least 80 mU/µg.

In one embodiment of the compositions described above, at least 10% of the rVWF in the composition is present in a high molecular weight VWF multimer of more than 10 dimers. In a specific embodiment, at least 15% of the rVWF is present in a high molecular weight VWF multimer of more than 10 dimers. In another specific embodiment, at least 20% of the rVWF is present in a high molecular weight VWF multimer of more than 10 dimers. In another specific embodiment, at least 25% of the rVWF is present in a high molecular weight VWF multimer of more than 10 dimers. In another specific embodiment, at least 30% of the rVWF is present in a high molecular weight VWF multimer of more than 10 dimers.

In one embodiment of the compositions described above, the composition comprises a culture supernatant. In one specific embodiment the culture supernatant is a mammalian cell culture supernatant. In a more specific embodiment, the mammalian cell culture supernatant is a CHO cell supernatant.

In one embodiment of the compositions described above, the rVWF is expressed in a cell culture comprising at least 2.4 µg/L copper. In a specific embodiment, the cell culture comprises at least 4 µg/L copper. In a more specific embodiment, the culture comprises between 2.4 µg/L and 20 µg/L copper. In one embodiment, the copper is provided as a copper salt, a copper chelate, or a combination thereof. In a specific embodiment, the copper salt is selected from the group consisting of copper sulfate, copper acetate, copper carbonate, copper chloride, copper hydroxide, copper nitrate, and copper oxide.

In one embodiment of the compositions described above, the cell culture is a batch culture.

In one embodiment of the compositions described above, the cell culture is a continuous culture. In a specific embodiment, the continuous culture is performed in chemostatic mode. In another specific embodiment, the continuous culture is performed in perfusion mode.

In one embodiment of the compositions described above, the level of NH4+ in the culture is maintained at a concentration below 4 mM.

In one embodiment of the compositions described above, the cell density of the culture is maintained at less than $2.5 \times 10^6$ cells per mL.

In one embodiment of the compositions described above, the cell density of the culture is maintained at less than $2.0 \times 10^6$ cells per mL.

In one embodiment of the compositions described above, the culture is maintained at less than $1.5 \times 10^6$ cells per mL.

In one embodiment of the compositions described above, the rVWF is co-expressed with recombinant Factor VIII (rFVIII). In a specific embodiment, a majority of the co-expressed rFVIII has been removed. In a more specific embodiment, the ratio of rVWF to rFVIII in the composition is at least 10:1.

In one embodiment of the compositions described above, the composition is formulated for pharmaceutical administration. In a specific embodiment, the composition is formulated for intravenous, subcutaneous, or intramuscular administration.

In one embodiment of the compositions described above, the composition is lyophilized.

In yet another aspect, the present invention includes a high molecular weight, recombinant vWF produced by a process, comprising the steps of: a) providing a culture of cells; b) introducing a nucleic acid sequence coding for vWF; c) selecting the cells carrying the nucleic acid sequence; and, d) expressing vWF in the cells under cell culture conditions comprising a cell culture medium comprising a copper concentration of at least 2.4 µg/L and a cell culture supernatant comprising an ammonium concentration less than 10 mM, wherein the vWF is highly multimeric vWF comprising about 14 to about 22 dimers and a specific Ristocetin activity of at least about 30 mU/µg. It is understood that all of the embodiments and concentrations described in the "Cell Culture Media" and "Methods of Producing Recombinant vWF" sections above can apply here.

The recombinant vWF of the present invention can include a high molecular weight recombinant vWF protein having a high specific activity. In one embodiment, the vWF of the present invention is a highly multimeric form of vWF. In some embodiments, the highly multimeric form of vWF includes at least up to about 14 dimers and in other embodiments at least up to about 22 dimers. In yet other embodiments, the highly multimeric form of vWF can range from about 10 to about 20 dimers, or from about 15 to about 25 dimers, or from about 20 to about 40 dimers. In certain embodiments, the recombinant vWF is comparable to plasmatic vWF.

As described herein, the present invention provides the surprising result that increased copper concentration in cell culture media can produce high molecular weight vWF with high specific activity. Cell culture media comprising a copper concentration, e.g., greater than about 2.4 µg/L can increase the yield of recombinant multimeric vWF, as compared to media without copper. In certain embodiments, the percentage of multimeric vWF (i.e., rVWF comprising at least 2 dimers) can be greater than about 50%, or greater than about 75%, or greater than about 90%. The multimeric distribution of the vWF can be analyzed using standard techniques such as, e.g., in Agarose electrophoresis under non-reducing conditions.

As provided herein, the recombinant vWF produced by the methods of the present invention can have a high specific activity, e.g., a high specific Ristocetin Cofactor activity. In one embodiment, the recombinant vWF produced by the methods of the present invention can include a specific Ristocetin Cofactor activity of at least 30 mU/µg and in another embodiment at least 50 mU/n. In other embodiments, the specific Ristocetin Cofactor activity can range from about 30 mU/µg to about 100 mU/µg or from about 50 mU/µg to about 100 mU/µg.

B. Recombinant ADAMTS13 (rA13)

The ADAMTS proteins (i.e., ADAMTS-1 to ADAMTS-20) are a family of secreted zinc metalloproteinases that share a common modular domain organization (for review, see, Flannery C. R., *Front Biosci.* 2006 Jan. 1; 11:544-69). All of the ADAMTS protein share a common core domain architecture, consisting of a signal peptide, followed by a prodomain, a zinc-dependent metalloproteinase catalytic domain, a disintegrin-like domain, a thrombospondin type I repeat, a cysteine-rich domain, and a spacer domain (Apte S. S., J Biol. Chem. 2009 Nov. 13; 284(46):31493-7). Additionally, all but ADAMTS-4 contain at least one more thrombospondin type I repeat domain, and many of the ADAMTS protein contain one or more additional ancillary domains. Notably, it has been reported that all ADAMTS protein appear to contain at least one calcium binding site and at least one zinc binding site located within the metalloproteinase catalytic domain (Andreini et al., *J. Proteome Res.,* 2005, 4 (3), pp 881-888).

Biological roles for ADAMTS proteins have been reported for various diseases and conditions, including, Antiangiogenesis, Renal interstitial fibrosis, Bone remodeling, Ovarian folliculogenesis, Atherosclerosis, Urogenital development, and Tumor growth/remodeling (ADAMTS-1); Ehler-Danlos syndrome type 7C and Bovine dermatopraxis (ADAMTS-2); Arthritis, Atherosclerosis, and Tendinopathy (ADAMTS-4); Arthritis and Glioblastoma (ADAMTS-5); Arthritis (ADAMTS-7); Antiangiogenesis, Brain malignancy, Arthritis, and Atherosclerosis (ADAMTS-8); Arthritis (ADAMTS-9, -12); Thrombotic thrombocytopenic purpura (ADAMTS- 13); and Antithrombosis/stroke (ADAMTS18) (for review, see, Lin and Liu, *Open Access Rheumatology Research and Reviews* 2009:1 121-131).

Recombinant ADAMTS13 (A13) has been expressed before in mammalian cells, however the specific activity varies widely dependent on the cell culture conditions. It has been found that many commercially available culture mediums are not sufficient for expression of rA13 with high specific activities, expressed as the ratio of activity, measured by FRETS-VWF73 assay, to antigen content, as determined by ELISA. In one aspect, the methods provided herein are based on several advantageous findings that allow for cell-culture expression of rA13 having increased levels of total and specific activity.

Accordingly, due to the shared structure-function relationship between the ADAMTS family of secreted metalloproteinases, the methods provided by the present invention allow for the expression of all ADAMTS proteins in cell culture and recovery from the cell medium.

In one aspect, the present invention provides a composition comprising recombinant ADAMTS13 (rA13) having a specific FRETS-VWF activity of at least 1600 mU/μg.

In one embodiment of the compositions described above, the rA13 has a specific FRETS-VWF activity of at least 800 mU/μg.

In one embodiment of the compositions described above, the composition comprises a culture supernatant. In a specific embodiment, the culture supernatant is a mammalian cell culture supernatant. In a more specific embodiment, the mammalian cell culture supernatant is a CHO cell supernatant.

In one embodiment of the compositions described above, the rA13 is expressed in a cell culture comprising at least 1 μg/L copper. In a specific embodiment, the cell culture comprises at least 2 μg/L copper. In a more specific embodiment, the culture comprises between 2 μg/L and 20 μg/L copper.

In one embodiment of the compositions described above, the copper is provided as a copper salt, a copper chelate, or a combination thereof. In a specific embodiment, the copper salt is selected from the group consisting of copper sulfate, copper acetate, copper carbonate, copper chloride, copper hydroxide, copper nitrate, and copper oxide.

In one embodiment of the compositions described above, the cell culture is a batch culture.

In one embodiment of the compositions described above, the cell culture is a continuous culture. In a specific embodiment, the continuous culture is performed in chemostatic mode. In another specific embodiment, the continuous culture is performed in perfusion mode.

In one embodiment of the compositions described above, the level of $NH_4^+$ in the culture is maintained at a concentration below 5 mM.

In one embodiment of the compositions described above, the level of $NH_4^+$ in the culture is maintained at a concentration below 4 mM.

In one embodiment of the compositions described above, the cell density of the culture is maintained at less than $4.0 \times 10^6$ cells per mL. In a specific embodiment, the cell density of the culture is maintained at less than $3.0 \times 10^6$ cells per mL. In a specific embodiment, the cell density of the culture is maintained at less than $2.0 \times 10^6$ cells per mL. In a more specific embodiment, the cell density of the culture is maintained at less than $1.5 \times 10^6$ cells per mL.

In one embodiment of the compositions described above, the composition is formulated for pharmaceutical administration. In a specific embodiment, the composition is formulated for intravenous, subcutaneous, or intramuscular administration.

In one embodiment of the compositions described above, the composition is lyophilized.

VI. Formulations

In one aspect, the formulations comprising the recombinant therapeutic proteins rVWF or rA13 of the present invention are lyophilized prior to administration. Lyophilization is carried out using techniques common in the art and should be optimized for the composition being developed [Tang et al., Pharm Res. 21:191-200, (2004) and Chang et al., Pharm Res. 13:243-9 (1996)].

Methods of preparing pharmaceutical formulations can include one or more of the following steps: adding a stabilizing agent as described herein to said mixture prior to lyophilizing, adding at least one agent selected from a bulking agent, an osmolarity regulating agent, and a surfactant, each of which as described herein, to said mixture prior to lyophilization. A lyophilized formulation is, in one aspect, at least comprised of one or more of a buffer, a bulking agent, and a stabilizer. In this aspect, the utility of a surfactant is evaluated and selected in cases where aggregation during the lyophilization step or during reconstitution becomes an issue. An appropriate buffering agent is included to maintain the formulation within stable zones of pH during lyophilization.

The standard reconstitution practice for lyophilized material is to add back a volume of pure water or sterile water for injection (WFI) (typically equivalent to the volume removed during lyophilization), although dilute solutions of antibacterial agents are sometimes used in the production of pharmaceuticals for parenteral administration [Chen, Drug Development and Industrial Pharmacy, 18:1311-1354 (1992)]. Accordingly, methods are provided for preparation of reconstituted recombinant VWF compositions comprising the step of adding a diluent to a lyophilized recombinant VWF composition of the invention.

The lyophilized material may be reconstituted as an aqueous solution. A variety of aqueous carriers, e.g., sterile water for injection, water with preservatives for multi dose use, or water with appropriate amounts of surfactants (for example, an aqueous suspension that contains the active compound in admixture with excipients suitable for the manufacture of aqueous suspensions). In various aspects, such excipients are suspending agents, for example and without limitation, sodium carboxymethylcellulose, methylcellulose, hydroxypropylmethylcellulose, sodium alginate, polyvinylpyrrolidone, gum tragacanth and gum acacia; dispersing or wetting agents are a naturally-occurring phosphatide, for example and without limitation, lecithin, or condensation products of an alkylene oxide with fatty acids, for example and without limitation, polyoxyethylene stearate, or condensation products of ethylene oxide with long chain aliphatic alcohols, for example and without limitation, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example and without limitation, polyethylene sorbitan monooleate. In various aspects, the aqueous suspensions also contain one or more preservatives, for example and without limitation, ethyl, or n-propyl, p-hydroxybenzoate.

To administer compositions to human or test animals, in one aspect, the compositions comprises one or more pharmaceutically acceptable carriers. The phrases "pharmaceutically" or "pharmacologically" acceptable refer to molecular entities and compositions that are stable, inhibit protein degradation such as aggregation and cleavage products, and in addition do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like, including those agents disclosed above.

The pharmaceutical formulations are administered intravenously, orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramusclar, intramammary, intraperitoneal, intrathecal, retrobulbar, intrapulmonary injection and or surgical implantation at a particular site is contemplated as well. Generally, compositions are essentially free of pyrogens, as well as other impurities that could be harmful to the recipient.

Single or multiple administrations of the compositions are carried out with the dose levels and pattern being selected by the treating physician. For the prevention or treatment of disease, the appropriate dosage depends on the type of disease to be treated, the severity and course of the disease, whether drug is administered for preventive or therapeutic purposes, previous therapy, the patient's clinical history and response to the drug, and the discretion of the attending physician.

In one aspect, formulations of the invention are administered by an initial bolus followed by a continuous infusion to maintain therapeutic circulating levels of drug product. As another example, the inventive compound is administered as a one-time dose. Those of ordinary skill in the art will readily optimize effective dosages and administration regimens as determined by good medical practice and the clinical condition of the individual patient. The frequency of dosing depends on the pharmacokinetic parameters of the agents and the route of administration. The optimal pharmaceutical formulation is determined by one skilled in the art depending upon the route of administration and desired dosage. See for example, Remington's Pharmaceutical Sciences, 18th Ed. (1990, Mack Publishing Co., Easton, Pa. 18042) pages 1435-1712, the disclosure of which is hereby incorporated by reference. Such formulations influence the physical state, stability, rate of in vivo release, and rate of in vivo clearance of the administered agents. Depending on the route of administration, a suitable dose is calculated according to body weight, body surface area or organ size. Appropriate dosages may be ascertained through use of established assays for determining blood level dosages in conjunction with appropriate dose-response data. The final dosage regimen is determined by the attending physician, considering various factors which modify the action of drugs, e.g. the drug's specific activity, the severity of the damage and the responsiveness of the patient, the age, condition, body weight, sex and diet of the patient, the severity of any infection, time of administration and other clinical factors. By way of example, a typical dose of a recombinant vWF of the present invention is approximately 50 U/kg, equal to 500 µg/kg. As studies are conducted, further information will emerge regarding the appropriate dosage levels and duration of treatment for various diseases and conditions.

VII. Methods of Treatment

The present invention further contemplates methods of treating a patient in need of rVWF or rA13 produced according to the methods described herein. Such methods of treatment can include administration of pharmaceutical formulations comprising the recombinant rA13 or the high molecular weight, recombinant vWF of the present invention.

In another aspect, the present invention provides methods for therapeutic or prophylactic treatments comprising the administration of an rVWF or rA13 composition provided herein. Generally, for therapeutic applications, formulations are administered to a subject with a disease or condition associated with ADAMTS13 or VWF dysfunction or otherwise in need thereof, in a "therapeutically effective dose." Formulations and amounts effective for these uses will depend upon the severity of the disease or condition and the general state of the patient's health. Single or multiple administrations of the formulations may be administered depending on the dosage and frequency as required and tolerated by the patient.

In one embodiment, the present invention provides methods of treating or preventing a disease or condition associated with an ADAMTS13 or VWF dysfunction. In a further embodiment, the pharmaceutical formulations comprising recombinant vWF can be administered to treat diseases related to vWF, such as von Willebrand's disease or hemophilia. In another embodiment, the invention provides methods of treating or preventing a disease or condition associated with the formation and/or presence of one or more thrombus, comprising the administration of a rA13 composition provided herein. In another embodiment, the invention provides methods of disintegrating one or more thrombus in a subject in need thereof. In yet other embodiments, the invention provides methods of treating or preventing an infarction in subject in need thereof. Generally, the methods provided by the invention comprise administering an rADAMTS13 composition as provided herein to a subject in need thereof.

Non-limiting examples of disorders associated with the formation and/or the presence of one or more thrombus are hereditary thrombotic thrombocytopenic purpura (TTP), acquired TTP, arterial thrombosis, acute myocardial infarction (AMI), stroke, sepsis, and disseminated intravascular coagulation (DIC).

Non-limiting examples of disorders associated with an infarction, include without limitation, myocardial infarction (heart attack), pulmonary embolism, cerebrovascular events such as stroke, peripheral artery occlusive disease (such as gangrene), antiphospholipid syndrome, sepsis, giant-cell arteritis (GCA), hernia, and volvulus.

VIII. EXAMPLES

The present invention will now be further illustrated in the following examples, without being limited thereto.

Example 1

Continuous cell culture experiments were performed using cultures of a recombinant CHO cell line expressing vWF. The basal medium was DMEM/F12, which contained about 0.3 µg/L of $Cu^{2+}$. The medium was supplemented with soy hydrolysate and copper sulfate ($CuSO_4 \cdot 5H_2O$) to bring the final copper concentration in the medium to greater than at least 2.4 µg/L.

Recombinant CHO cells expressing vWF were cultivated by continuous cell cultures so that the ammonium levels ($NH_4^+$) were kept at a concentration less than about 10 mM. It was found that production systems providing a continuous supply of medium (e.g., perfusion or chemostat cultures) were preferable because conventional batch or fed batch techniques produced high $NH_4^+$ concentrations at the end of the culture. At the end of the culture, the highly multimeric vWF was isolated and the specific Ristocetin Cofactor activity of the vWF was measured.

Example 2

Recombinant Factor VIII (rFVIII) and Von Willebrand Factor (rVWF) were co-expressed in batch cultures of GD8/6 cells to determine the effect of the composition of the culture medium on VWF expression and activity. Briefly, GD8/6 cells were batch cultivated in BAV-SP medium composed of a modified DMEM/F12 basal powder (Table 5) and additional supplements also containing 4 g/L of soy hydrolysate, see Table 6, with and without additional copper supplementation. To test the effect of low copper concentraions on rVWF expression and activity, basal BAV-SP media was used. The basal media contained 0.3 µg/L copper and was supplemented with soy hydrolysate, which contributed an additional 0.7 µg/L copper, as determined experimentally, providing a final copper concentration of 1.0 µg/L. As a comparision, the BAV-SP media used for the batch cultures was further supplemented with an additional 3.3 µg/L of $Cu^{2+}$, providing a final copper concentration of 4.3 µg/L, to determine the effect high copper concentrations on VWF expression and activity.

TABLE 5

Composition of BAV-SP Culture Media

| BAV-SP-Medium Components | mg/L |
|---|---|
| Amino Acids | |
| L-Alanine | 4.45 |
| L-Arginine HCl | 147.50 |
| L-Asparagine-$H_2O$ | 30.21 |
| L-Aspartic Acid | 6.65 |
| L-Cystéine HCl—$H_2O$ | 32.55 |
| L-Cystine 2HCl | 57.35 |
| L-Glutamic Acid | 7.35 |
| Glycine | 18.75 |
| L-Histidine-$H_2O$ HCl | 31.48 |
| Hydroxy-L-Proline | |
| L-Isoleucine | 54.47 |
| L-Leucine | 59.05 |
| L-Lysine HCl | 91.25 |
| L-Methionine | 17.24 |
| L-Phenylalanine | 35.48 |
| L-Proline | 52.24 |
| L-Serine | 26.25 |
| L-Threonine | 53.45 |
| L-Tryptophan | 29.01 |
| L-Tyrosine 2Na 2H2O | 55.79 |
| L-Valine | 52.85 |
| Vitamins | |
| Ascorbic Acid | 3.499 |
| Biotin | 0.0035 |
| Choline Chloride | 8.980 |
| D-Ca-Pantothenate | 2.240 |
| Folic Acid | 2.650 |
| I-Inositol | 12.600 |
| Nicotinamide | 2.020 |
| Pyridoxine HCl | 2.031 |
| Riboflavin | 0.219 |
| Thiamine HCl | 2.170 |
| Vitamin B12 | 0.680 |
| Anorganic Salts | |
| Calcium Chloride (CaCl2) | 116.600 |
| Copper Sulfate (CuSO$_4$.5$H_2O$) | 0.0013 |
| Ferric Nitrate (Fe(NO$_3$)3-9$H_2O$) | 0.050 |
| Ferrous Sulfate (FeSO$_4$—7$H_2O$) | 0.417 |

TABLE 5-continued

Composition of BAV-SP Culture Media

| BAV-SP-Medium Components | mg/L |
|---|---|
| Magnesium Chloride (MgCl2) | 28.640 |
| Magnesium Sulfate (MgSO4) | 48.840 |
| Potassium Chloride (KCl) | 311.800 |
| Sodium Chloride (NaCl) | 6995.500 |
| Sodium phosphate (Na2HPO4) | 71.020 |
| Sodium phosphate (NaH2PO4) | 62.500 |
| Zinc Sulfate Heptahydrate (ZnSO4-7H2O) | 0.432 |
| Sodium selenite | 0.0131 |
| Others | |
| D-Glucose | 3151 |
| Linoleic Acid | 0.042 |
| Lipoic Acid | 0.105 |
| Putrescine 2HCl | 0.081 |
| Thymidine | 0.365 |
| Hypoxantine Na | 2.390 |
| Sodium Pyruvate | 55.000 |

TABLE 6

Composition of BAV-SP Supplement

| Componets for final formulation | |
|---|---|
| L-Glutamine | 600.00 |
| Ethanolamine | 1.530 |
| Synperonic F68 | 250.000 |
| Sodium Bicarbonate (NaHCO3) | 2000.000 |
| Soy peptone | 4000.00 |
| Total formulation | 18596.8 |

GD8/6 cells expressing rVWF were grown in either low copper media (Table 7) or high copper media (Table 8) for 7 days. After 2 days the cultures were subcultured to perform a batch culture for a period of 5 days. Samples of the culture supernatant were tested daily for rVWF content (vWF ELISA), total (Ristocetin) and specific (Specific Activity) via a ristocetin cofactor assay. Various culture parameters, including cell count, cell viability, and ammonium concentration were also monitored daily (except for batch days 3 and 4).

Unexpectedly, cell cultures grown under high copper concentrations produced supernatants containing significantly higher total and specific rVWF activity (compare results in Table 7 and Table 8). For example, at batch day 4, the cell culture grown under high copper concentration contained 1.52 IU rVWF activity/mL, as compared to 0.2 IU rVWF activity/mL for the low copper culture. This is despite the fact that the low copper cell culture produced nearly twice the amount of rVWF as the high copper cell culture. Furthermore, the specific activity of the supernatant obtained from the high copper culture was more than 13 times greater than that of the low copper culture supernatant (831 mU/10 µg rVWF v. 62 mU/10 µg rVWF).

As seen in Table 7 and Table 8, the total and specific ristocetin cofactor activity of the high copper culture was twice that of the low copper culture at batch day 1. Furthermore, in contrast to the subsequent increases in activity observed in the high copper culture, no increase in the amount of ristocetin cofactor activity was seen after batch day 1 for the low copper cell culture. Consistent with this result, agarose gel electrophoresis analysis of the rVWF multimer state revealed that a low concentration of high molecular weight rVWF, relative to the concentration of low molecular weight rVWF species, was present in the supernatant of the low copper cell culture at batch day 1, and that the relative concentration further decreased over time (FIGS. 1A and 1B). In contrast, supplementation of the culture medium with $Cu^{2+}$ resulted in a consistent formation of ristocetin cofactor (RiCoF) active antigen through the fourth day. Consistently, no loss in the amount of stable high molecular weight rVWF multimers occurred through day 4 of the batch culture (FIGS. 1A and 1B). The densitometric results of the agarose electrophoresis gel shown in FIG. 1B revealed that under low copper conditions the culture was only able to produce a rVWF population in which more than 10% (i.e., 16.3%) of the rVWF was present in molecules having more than 10 dimers for one day of the batch culture (i.e. "day3" sample in Lane 2 of the agarose gel of FIG. 1A), and notably, this population fell to only 4% at day 5 of the batch culture ("day 7" sample in Lane 6). In contrast under high copper conditions the relative amount of vWF multimers with more than 10 dimers is consistently around 30% through day 4 of the batch culture ("day 3" to "day 6" in Lanes 7-10; 28% to 31.4%).

Notably, beginning at batch day 5 of the high copper batch culture, when $NH_4^+$ levels exceeded 100 mg/L (greater than about 5.0 mM), the expression of additional antigen (18.3 to 35.4 µg/L; compare batch days 4 and 5 of Table 8) did not result in a concomitant increase in the RiCoF activity present in the supernatant. Consistent with this result, the level of high molecular weight rVWF multimers at batch day 5 (day 7 of the culture) decreased relative to the concentration of low molecular weight rVWF multimers. Also only on batch day 5 ("day 7" sample of the culture in Lane 11) the relative amount of the vWF with more than 10 dimers is reduced to 21.4%.

Taken together, the data provided above demonstrate that the supplementation of copper concentrations in cell cultures expressing rVWF dramatically increases the total and specific rVWF ristocetin cofactor activity, as well the stable production of high molecular weight rVWF multimers. Furthermore, the data show a correlation between the presence of high $NH_4^+$ concentrations in the cell culture and the loss of rVWF ristocetin cofactor activity and high molecular weight rVWF multimer production.

TABLE 7

Expression of rVWF in mammalian cell culture performed in batch mode using BAV-SP media with a low copper concentration (1.0 µg/L).

| batch day | Cell Count [10E6 cells/mL] | $NH_4^+$ [mg/l] | Viability [%] | vWF ELISA [µg/ml] | Ristocetin [IU/mL] | Specific Actifity mU/10 µg |
|---|---|---|---|---|---|---|
| 0 | 0.42 | 21 | 98.8 | n.d. | n.d. | n.d. |
| 1 | 0.78 | 43 | n.d. | 6.3 | 0.23 | 365 |
| 2 | 1.24 | 64 | 99.1 | 12.8 | 0.23 | 180 |

TABLE 7-continued

Expression of rVWF in mammalian cell culture performed in batch mode using BAV-SP media with a low copper concentration (1.0 µg/L).

| batch day | Cell Count [10E6 cells/mL] | $NH_4^+$ [mg/l] | Viability [%] | vWF ELISA [µg/ml] | Ristocetin [IU/mL] | Specific Actifity mU/10 µg |
|---|---|---|---|---|---|---|
| 3 | 1.86 | n.d. | n.d. | 22.7 | 0.21 | 93 |
| 4 | 2.49 | n.d. | n.d. | 32.2 | 0.20 | 62 |
| 5 | 3.11 | 106 | 98.3 | 44.4 | 0.20 | 45 |

TABLE 8

Expression of rVWF in mammalian cell culture performed in batch mode using BAV-SP media with a high copper concentration (4.3 µg/L).

| batch day | Cell Count [10E6 cells/mL] | $NH_4^+$ [mg/l] | Viability [%] | vWF ELISA [µg/ml] | Ristocetin [IU/mL] | Specific Actifity mU/10 µg |
|---|---|---|---|---|---|---|
| 0 | 0.40 | 21 | 99.3 | n.d. | n.d. | n.d. |
| 1 | 0.71 | 42 | n.d. | 4.8 | 0.40 | 833 |
| 2 | 1.23 | 63 | 99.5 | 8.7 | 0.62 | 713 |
| 3 | 1.85 | n.d. | n.d. | 15.0 | 1.07 | 713 |
| 4 | 2.54 | n.d. | n.d. | 18.3 | 1.52 | 831 |
| 5 | 3.32 | 109 | 98.9 | 35.4 | 1.55 | 438 |

Example 3

Recombinant Factor VIII (rFVIII) and Von Willebrand Factor (rVWF) were co-expressed in continuous cultures of GD8/6 cells operated under chemostatic conditions to determine the effect of the composition of the culture medium on VWF expression and activity. Briefly, GD8/6 cells were cultivated in BAV-SP medium containing 4 g/L of soy hydrolysate with and without copper supplementation as described in Example 2. To test the effect of low copper concentraions on rVWF expression and activity, basal BAV-SP media was used. The basal media contained 0.3 µg/L copper and was supplemented with soy hydrolysate, which contributed an additional 0.7 µg/L copper, providing a final copper concentration of 1.0 µg/L. As a comparision, the BAV-SP media used for the batch cultures was further supplemented with an additional 3.3 µg/L of $Cu^{2+}$, providing a final copper concentration of 4.3 µg/L, to determine the effect high copper concentrations on VWF expression and activity. Cultures grown in the presence of high and low copper concentrations were cultivated under both high ($2.8 \times 10^6$ cells/mL) and low (appr. 1.4×10E06 cells/mL) cell densities.

As before, samples of the culture supernatant were tested for rVWF content (vWF ELISA), total (Ristocetin) and specific (Specific Activity) activity via a ristocetin cofactor assay. Various culture parameters, including cell count, cell viability, and ammonium concentration were also monitored. Data were generated from the steady state phase of weeks 2 and 3 of the chemostat cultures (Table 9 to Table 13).

TABLE 9

Mean data for rVWF expression in chemostatic cell culture during weeks 2 and 3.

| Cell Count | Copper Concentration | Cell Count [10E6 cells/mL] | NH4+ [mM] | Viability [%] | vWF ELISA [µg/ml] | Ristocetin [IU/mL] | specific actifity [mU/10 µg] |
|---|---|---|---|---|---|---|---|
| high | low | 2.88 | 3.88 | 97.74 | 44.56 | 0.10 | 21.62 |
| high | high | 2.79 | 4.04 | 98.25 | 38.38 | 0.19 | 53.11 |
| low | low | 1.55 | 3.33 | 98.63 | 18.96 | 0.10 | 50.16 |
| low | high | 1.43 | 3.17 | 98.59 | 11.76 | 0.70 | 598.76 |

TABLE 10 rVWF expression in chemostatic cell culture under high cell count, low copper conditions during weeks 2 and 3.

| Day | Cell Count [10E6 cells/mL] | NH4+ [mM] | Viability [%] | vWF ELISA [μg/ml] | Ristocetin [IU/mL] | specific actifity [mU/10 μg] |
|---|---|---|---|---|---|---|
| 8  | 2.54 | 3.7  | 98.20 | 39.8  | 0.095 | 23.86934673 |
| 9  | 3.02 | 4.2  | 97.40 |       |       |             |
| 10 | 2.97 | 3.9  | 97.90 | 41.3  | 0.095 | 23.00242131 |
| 11 | 2.78 |      |       |       |       |             |
| 13 | 2.91 | 3.8  | 97.60 | 41.7  | 0.095 | 22.78177458 |
| 14 | 2.90 | 3.8  | 97.40 |       |       |             |
| 15 | 3.05 | 3.9  | 97.70 | 44.7  | 0.095 | 21.25279642 |
| 16 | 2.99 | 3.8  | 98.30 |       |       |             |
| 17 | 2.76 | 3.9  | 97.40 | 55.3  | 0.095 | 17.17902351 |
|    | 2.88 | 3.88 | 97.74 | 44.56 | 0.10  | 21.62       |

TABLE 11 rVWF expression in chemostatic cell culture under high cell count, high copper conditions during weeks 2 and 3.

| Day | Cell Count [10E6 cells/mL] | NH4+ [mM] | Viability [%] | vWF ELISA [μg/ml] | Ristocetin [IU/mL] | specific actifity [mU/10 μg] |
|---|---|---|---|---|---|---|
| 8  | 2.52 | 3.9  | 98.30 | 31.8  | 0.35  | 110.0628931 |
| 9  | 2.92 | 4.3  | 98.50 |       |       |             |
| 10 | 2.80 | 4.2  | 98.60 | 37.4  | 0.32  | 85.56149733 |
| 11 | 2.57 |      |       |       |       |             |
| 13 | 2.81 | 3.9  | 98.50 | 37.6  | 0.095 | 25.26595745 |
| 14 | 2.92 | 3.9  | 97.80 |       |       |             |
| 15 | 2.77 | 3.9  | 97.80 | 43.0  | 0.095 | 22.09302326 |
| 16 | 2.72 | 4.0  | 98.30 |       |       |             |
| 17 | 3.04 | 4.1  | 98.20 | 42.1  | 0.095 | 22.56532067 |
|    | 2.79 | 4.04 | 98.25 | 38.38 | 0.19  | 53.11       |

TABLE 12 rVWF expression in chemostatic cell culture under low cell count, low copper conditions during weeks 2 and 3.

| Day | Cell Count [10E6 cells/mL] | NH4+ [mM] | Viability [%] | vWF ELISA [μg/ml] | Ristocetin [IU/mL] | specific actifity [mU/10 μg] |
|---|---|---|---|---|---|---|
| 8  | 1.61 | 3.3  | 99.10 | 19.3  | 0.095 | 49.22279793 |
| 9  | 1.65 | 3.3  | 98.00 |       |       |             |
| 10 | 1.49 | 3.3  | 98.90 | 18.6  | 0.095 | 51.07526882 |
| 11 | 1.58 |      |       |       |       |             |
| 13 | 1.58 | 3.4  | 98.10 | 18.1  | 0.095 | 52.48618785 |
| 14 | 1.56 | 3.3  | 99.30 |       |       |             |
| 15 | 1.52 | 3.3  | 98.50 | 18.9  | 0.095 | 50.26455026 |
| 16 | 1.50 | 3.3  | 98.40 |       |       |             |
| 17 | 1.50 | 3.4  | 98.70 | 19.9  | 0.095 | 47.73869347 |
|    | 1.55 | 3.33 | 98.63 | 18.96 | 0.10  | 50.16       |

TABLE 13 rVWF expression in chemostatic cell culture under low cell count, high copper conditions during weeks 2 and 3.

| Day | Cell Count [10E6 cells/mL] | NH4+ [mM] | Viability [%] | vWF ELISA [μg/ml] | Ristocetin [IU/mL] | specific actifity [mU/10 μg] |
|---|---|---|---|---|---|---|
| 8 | 1.46 | 3.2 | 98.80 | 11.6 | 0.73 | 629.3103448 |
| 9 | 1.45 | 3.2 | 98.20 | | | |
| 10 | 1.37 | 3.1 | 98.90 | 11.0 | 0.7 | 636.3636364 |
| 11 | 1.43 | | | | | |
| 13 | 1.33 | 3.2 | 98.10 | 11.1 | 0.68 | 612.6126126 |
| 14 | 1.39 | 3.2 | 97.20 | | | |
| 15 | 1.51 | 3.2 | 99.70 | 12.4 | 0.69 | 556.4516129 |
| 16 | 1.49 | 3.2 | 98.60 | | | |
| 17 | 1.43 | 3.2 | 99.20 | 12.7 | 0.71 | 559.0551181 |
| | 1.43 | 3.17 | 98.59 | 11.76 | 0.70 | 598.76 |

Figure 2A:
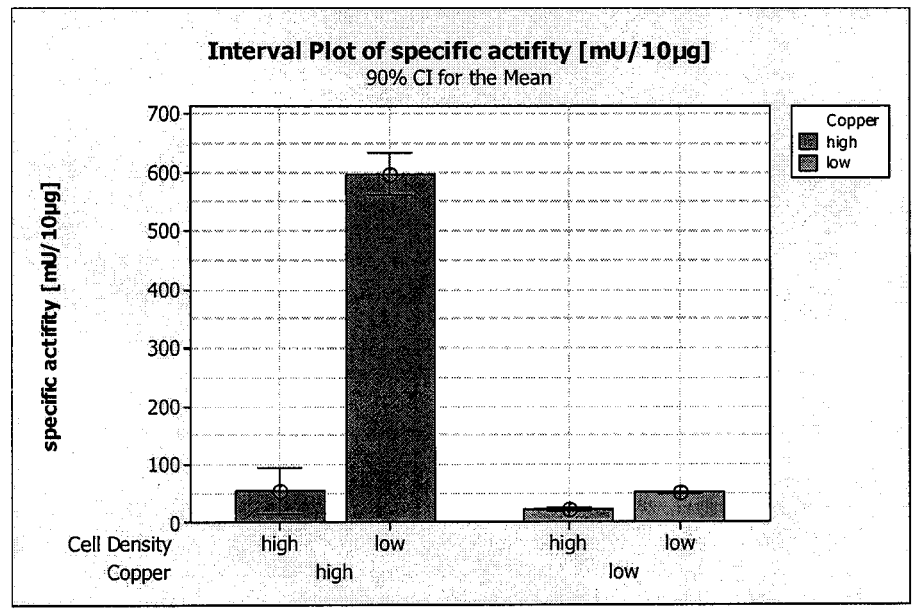
FIG. 2. (2A) Interval plot of the average rVWF specific activity present in rVWF cell culture supernatants grown at high and low cell densities in the presence of high or low levels of copper. (2B) Interval plot of the average $NH_4^+$ concentration found in rVWF cell culture supernatants grown at high and low cell densities in the presence of high or low levels of copper.
Figure 2B:
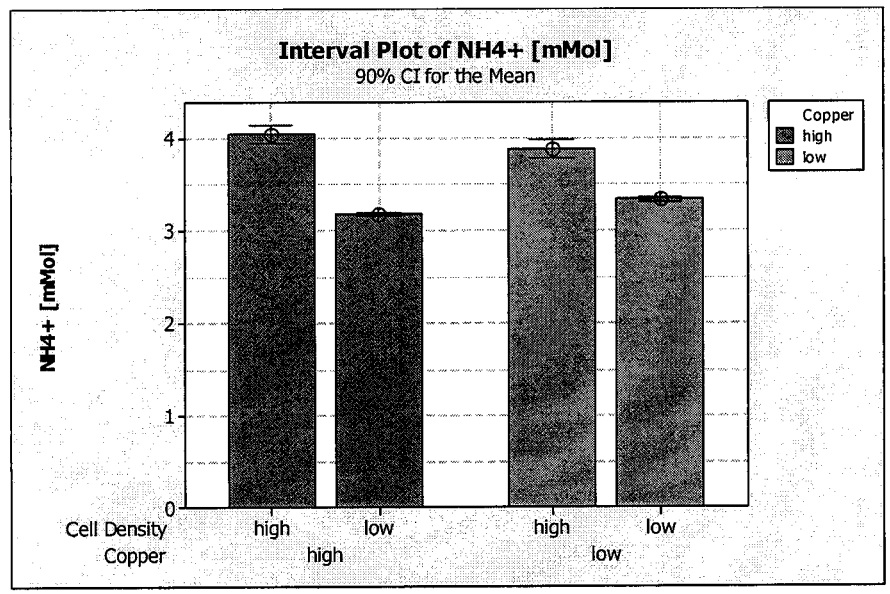

As shown in FIG. 2A, supernatant harvested from continuous rVWF cell culture grown at low cell densities and high copper concentrations contained high specific activity (average of 600 mU/10 μg), while supernatants harvested from rVWF cell cultures grown at high cell densities in the presence of high or low copper concentrations and rVWF cell cultures grown at low cell density in the presence of low copper concentration contained low specific activities (less than 100 mU/10 μg). Consistent with the results observed for batch cultures, FIG. 2B shows that continuous mammalian cell cultures expressing rVWF with high specific activities have lower $NH_4^+$ concentrations than do cultures producing rVWF with low specific activities. This data further strengthen the correlation between $NH_4^+$ concentration in the cell culture and the specific activity of rVWF produced by the culture. Notably, the combination of high copper concentration and low ammonium concentration in the cell culture allowed for the production significantly improved rVWF activity.

Figures 6A, 6B:
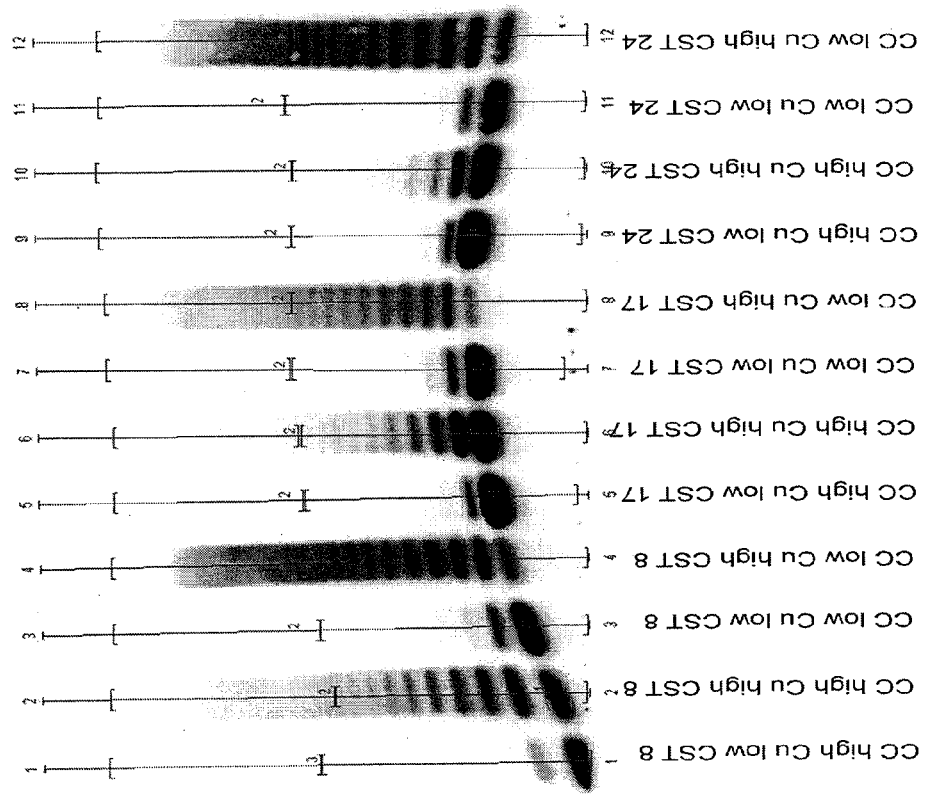
FIG. 6. (6A) Low resolution (1%) agarose gel electrophoresis of rVWF expressed in mammalian cell culture in the presence of low (1.0 µg/L) and high (4.3 µg/L) copper concentration under high and low cell densities as described in Example 3. Note that culture Day 8 and 17 ("CST8" and "CST17") is equivalent to Day 8 and Day 17 of Table 10 to Table 13. (6B) The relative amounts of VWF multimers having 1 to 10 dimers and more than 10 dimers, as indicated by the bands defined in FIG. 6A, was quantitated by densitometric analysis.

Consistent with this result, agarose gel electrophoresis analysis of the rVWF multimer state of chemostat cultures (FIG. 6) revealed that only supernatants from cultures operated at high copper and low cell density and thus low ammonium resulted in a consistent expression high multuimeric vWF (about 23% to 27% on CST day 8, 17 and 24 in Lanes 4, 8, and 12, respectively). All other conditions do not reach consistently high amounts of more than 10% of vWF with more than 10 dimers over an extended cultivation period.

Example 4

To determine the effect of culture media copper concentration on the expression and specific activity of rA13, mammalian cell cultures expression rA13 were grown for 4 weeks under chemostatic continuous culture conditions in ADAMTS13 medium comprising a modified DMEM/F12 basal media BESP845 and additional supplements (Table 14) containing copper concentrations ranging from 0.66 μg/L (without additional copper supplementation) and with additional copper supplementation to 4 μg/L. As shown in Table 15, increasing copper concentration in the cell culture media resulted in a significant increase in volumetric (P) and specific (q) productivity expressed as the total rA13 activity produced per liter culture and day and the total rA13 activity produced per cell and day, respectively.

TABLE 14

Composition of ADAMTS13 medium.

| | mg/L |
|---|---|
| DMEM/F12 BESP845 | |
| Amino Acids | |
| L-Alanine | 13.3500 |
| L-Arginine HCl | 147.5000 |
| L-Asparagine-$H_2O$ | 45.1600 |
| L-Aspartic Acid | 19.9500 |
| L-Cystéine HCl—$H_2O$ | 32.5500 |
| L-Cystine 2HCl | 102.3500 |
| L-Glutamic Acid | 22.0500 |
| Glycine | 26.2500 |
| L-Histidine-$H_2O$ HCl | 51.4800 |
| L-Isoleucine | 74.4700 |
| L-Leucine | 119.0500 |
| L-Lysine HCl | 146.2500 |
| L-Methionine | 100.0000 |
| L-Phenylalanine | 60.4800 |
| L-Proline | 63.7400 |
| L-Serine | 36.7500 |
| L-Threonine | 53.4500 |
| L-Tryptophan | 29.0100 |
| L-Tyrosine 2Na 2H2O | 75.7900 |
| L-Valine | 82.8500 |
| salts | |
| Calcium Chloride (CaCl2) | 116.6000 |
| Copper Sulfate ($CuSO_4.5H_2O$) | 0.0026 |
| Ferric Nitrate (Fe($NO_3$)3-$9H_2O$) | 0.0500 |
| Ferrous Sulfate ($FeSO_4$—$7H_2O$) | 1.0170 |
| Magnesium Chloride (MgCl2) | 28.6400 |
| Magnesium Sulfate (MgSO4) | 48.8400 |
| Potassium Chloride (KCl) | 311.8000 |
| Sodium Chloride (NaCl) | 5495.5000 |
| Na2HPO4 Anhydrous | 213.0200 |
| NaH2PO4 Anhydrous | 54.3500 |
| Zinc Sulfate Heptahydrate (ZnSO4-27H2O) | 0.4320 |
| Sodium selenite.anhydrous | 0.0087 |
| Vitamins | |
| Ascorbic Acid | 3.4990 |
| Biotin | 0.2035 |
| Choline Chloride | 26.9800 |
| D-Ca-Pantothenate | 6.2400 |
| Folic Acid | 6.6500 |
| I-Inositol | 36.6000 |
| Nicotinamide | 7.0200 |
| Pyridoxine HCl | 6.0310 |
| Riboflavin | 0.6590 |
| Thiamine HCl | 6.5100 |
| Vitamin B12 | 2.6800 |

TABLE 14-continued

Composition of ADAMTS13 medium.

| | mg/L |
|---|---|
| miscellaneous | |
| D-Glucose | 5000.0000 |
| Linoleic Acid | 0.0420 |
| Lipoic Acid | 1.0050 |
| Putrescine 2HCl | 3.6810 |
| Thymidine | 0.3650 |
| Hypoxantine Na | 2.3900 |
| Sodium Pyruvate | 55.0000 |
| DMEM/F12 BESP845: Total | 12738.3 |
| ADAMTS-13 Medium Supplements | |
| L-Glutamin | 1300.0000 |
| Pluronic F68 | 1000.0000 |
| Etanolamin | 1.5300 |
| ZnSo4*7 H2O | 1.0000 |
| Na-Hydrogencarbonat | 1500.0000 |
| Supplements Total | 3802.5 |
| Total amount of Ingridients | 16540.8 |

Figure 3A:
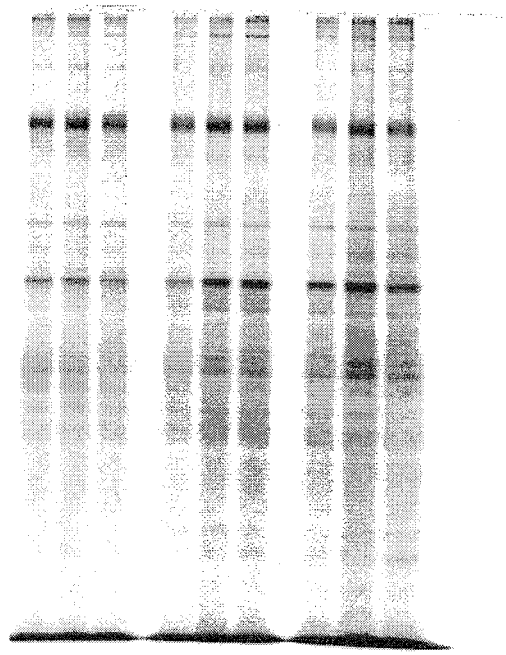
FIG. 3. Supernatants from cell cultures expressing recombinant ADAMTS13 in the presence of increasing levels of copper were investigated by SDS-PAGE analysis. rA13 was visualized after SDS-PAGE by (3A) silver staining and (3B) anti-A13 western blotting.
Figure 3B:
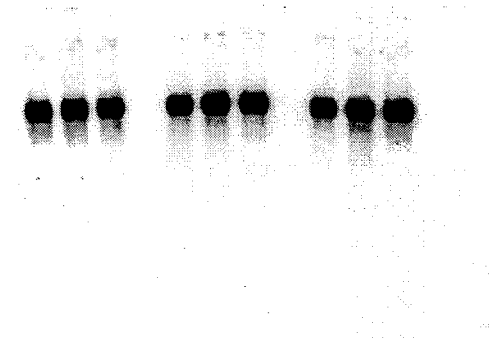

To determine if increased copper concentrations affected the integrity of the expressed rA13, supernatant harvested from rA13 cell cultures grown in media containing 0.66 μg/L, 1 μg/L, and 4 μg/L copper was examined by SDS-PAGE analysis. As seen in FIG. 3A (silver stain) and FIG. 3B (anti-A13 western blot), no obvious change in product quality by gel electrophoresis was observed. Specifically, no increase in the level of truncated 170 kD or other low MW rA13 variants and no other additional or increased HCP bands resulted from rA13 expression in the presence of increased copper concentrations.

Figure 4:
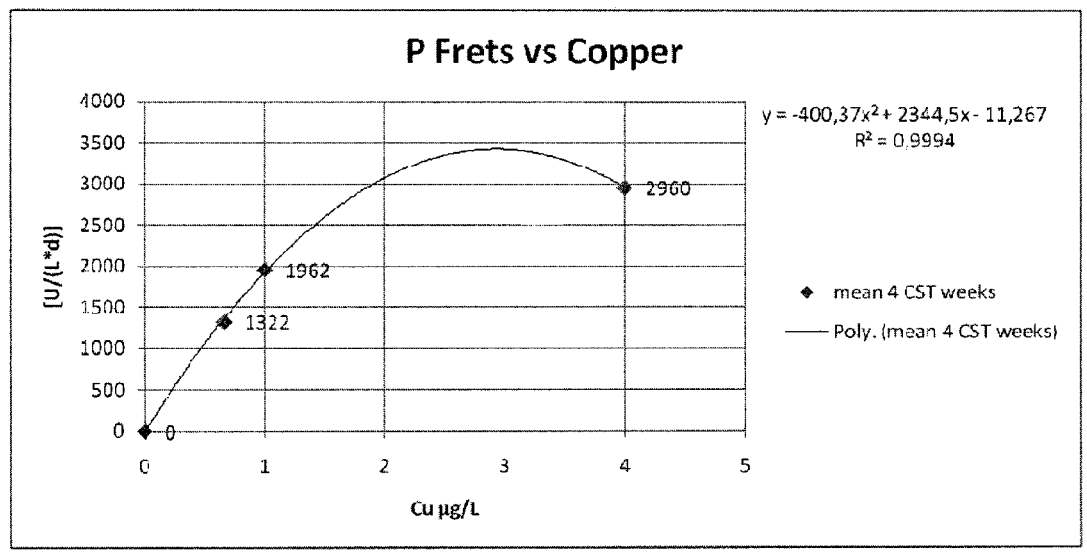
FIG. 4. Plot of volumetric productivity (P Frets) data versus copper concentration showing an extrapolation (solid line) of optimal copper concentration effect on rA13 productivity.
Figure 5A:
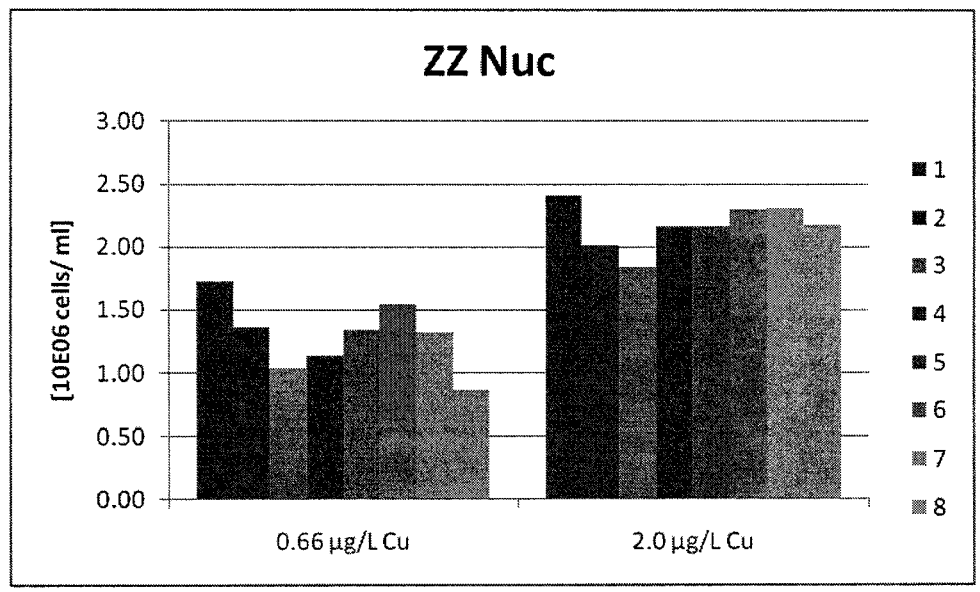
FIG. 5A-K. Bar graphs from continuous suspension (chemostat) cell cultures expressing rA13 over a culture time of 8 weeks comparing the effects of basal levels of copper (0.66 µg/L) to that of cultures supplemented to a final concentration of 2 µg/L copper. Each bar represents the mean data of one week of chemostatic culturing. The legend refers to the particular week represented in the data.
Figure 5B:
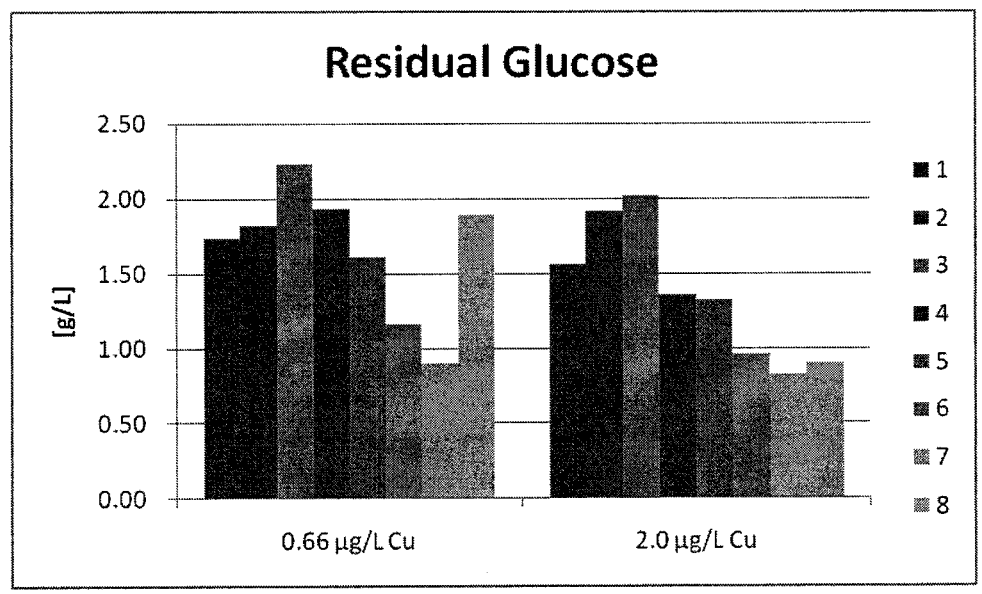
Figure 5C:
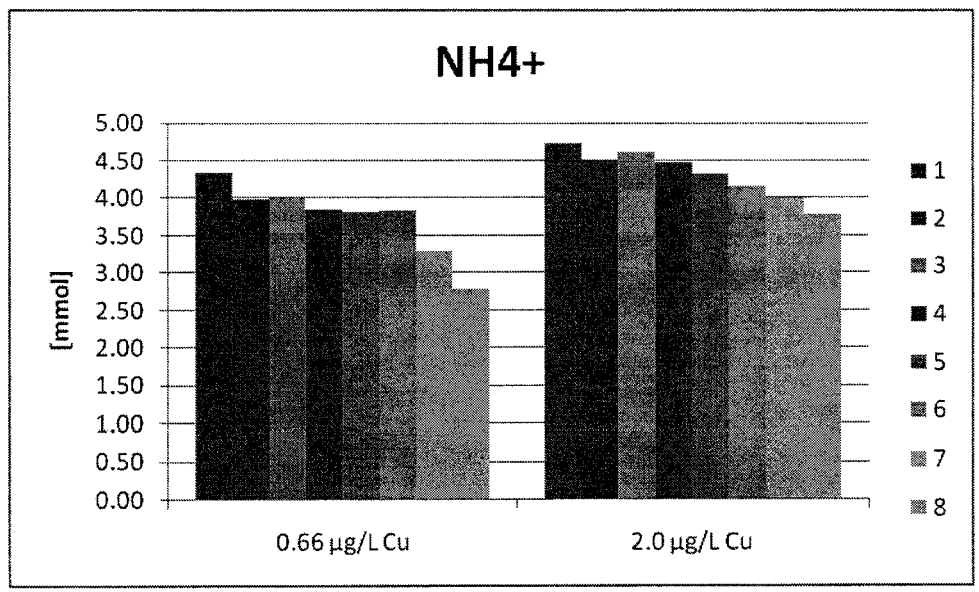
Figure 5D:
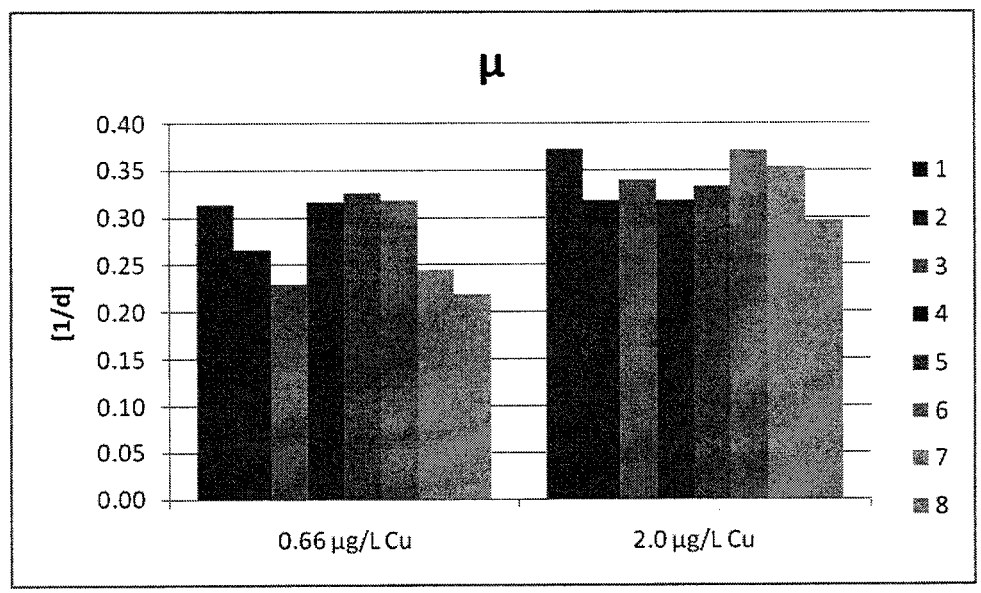
Figure 5E:
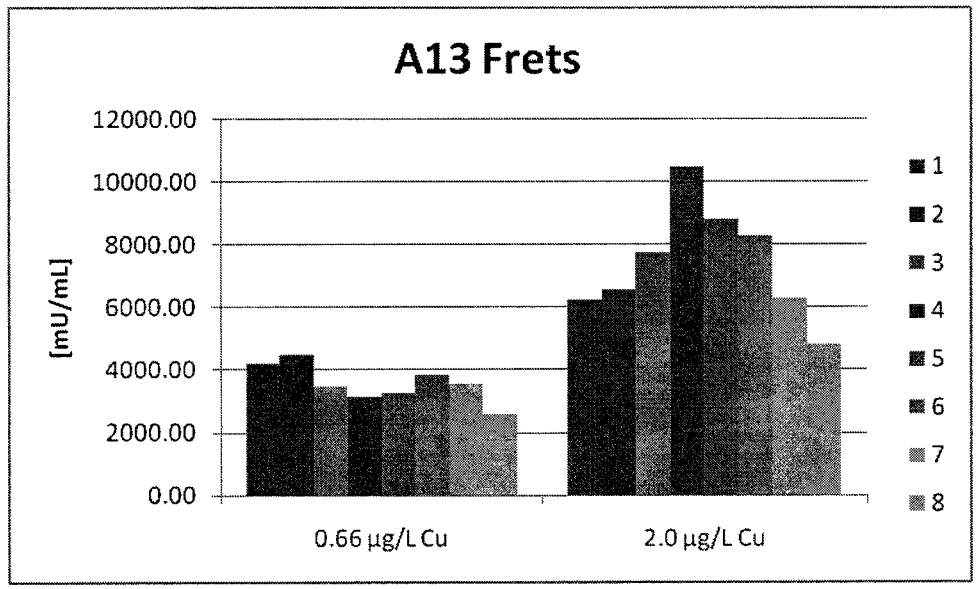
Figure 5F:
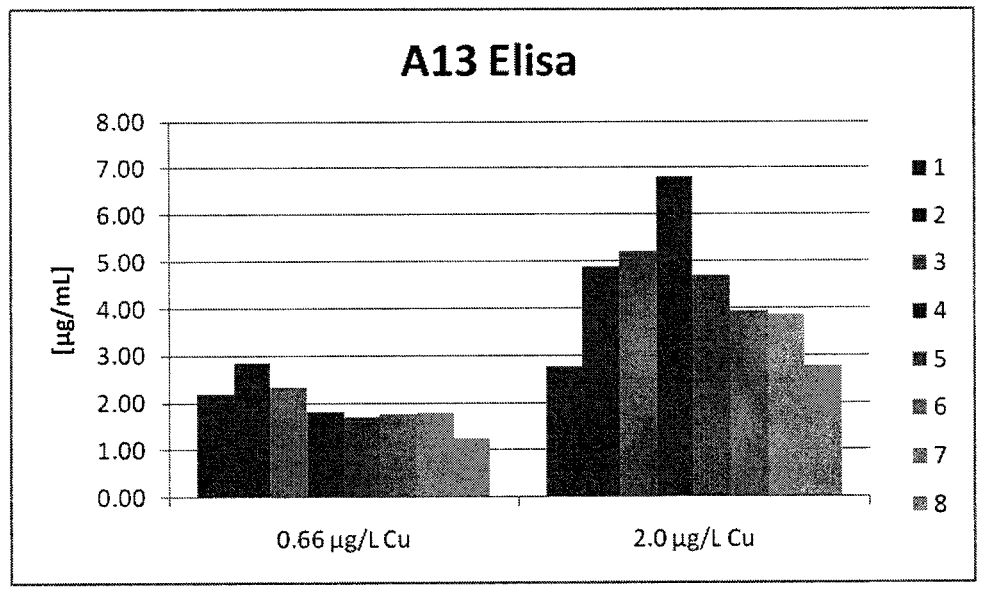
Figure 5G:
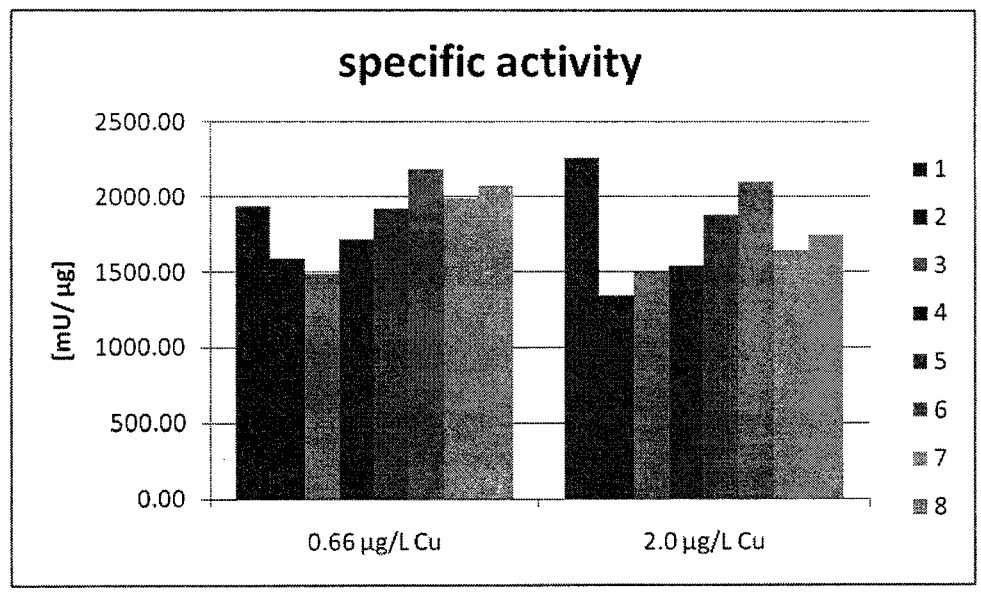
Figure 5H:
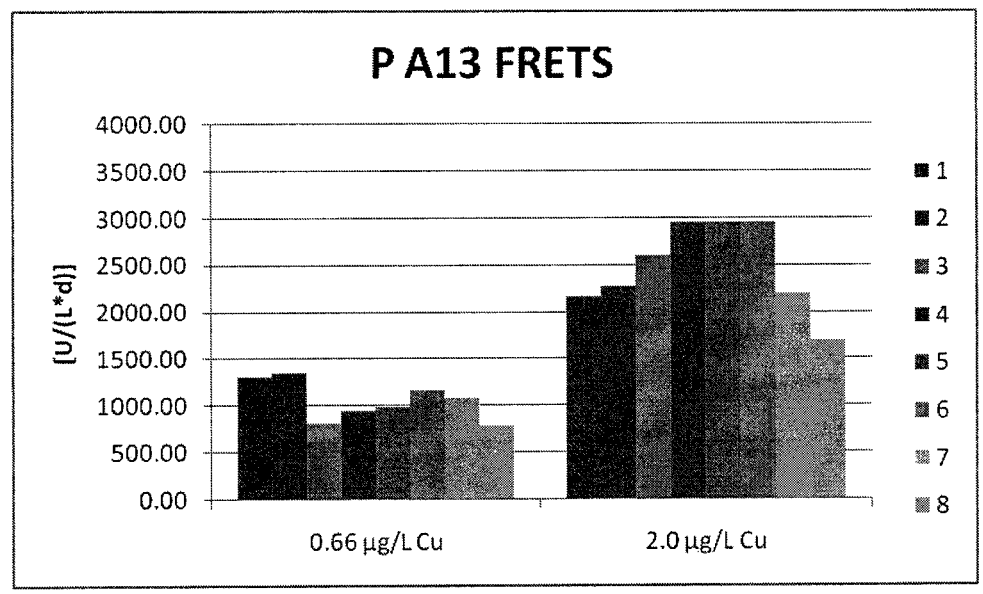
Figure 5I:
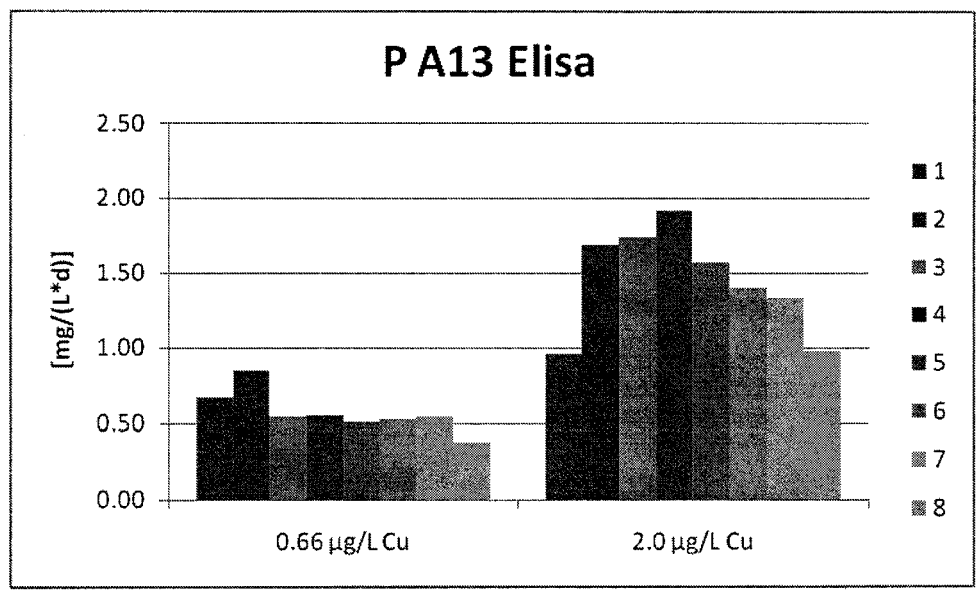
Figure 5J:
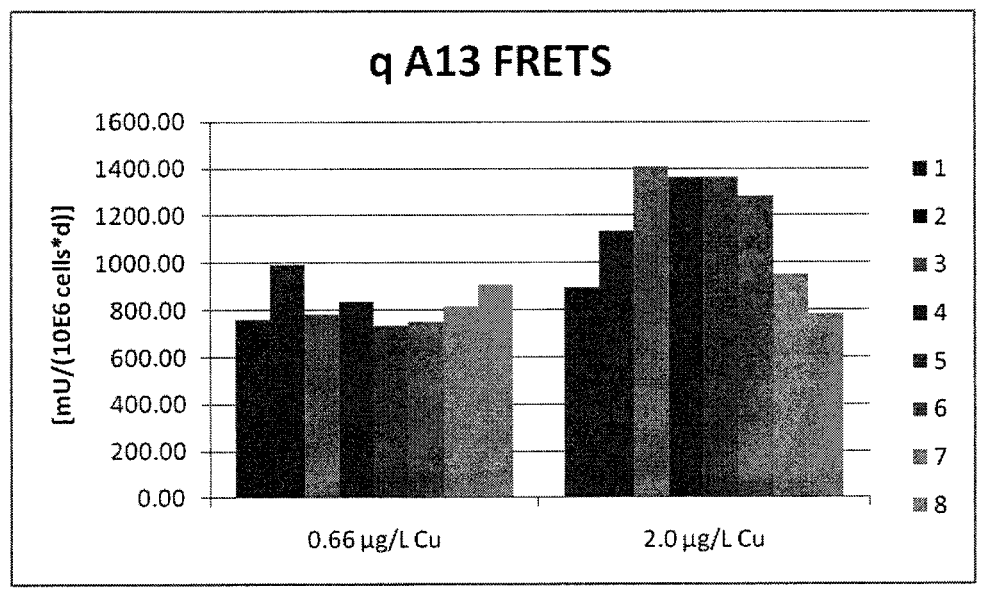
Figure 5K:
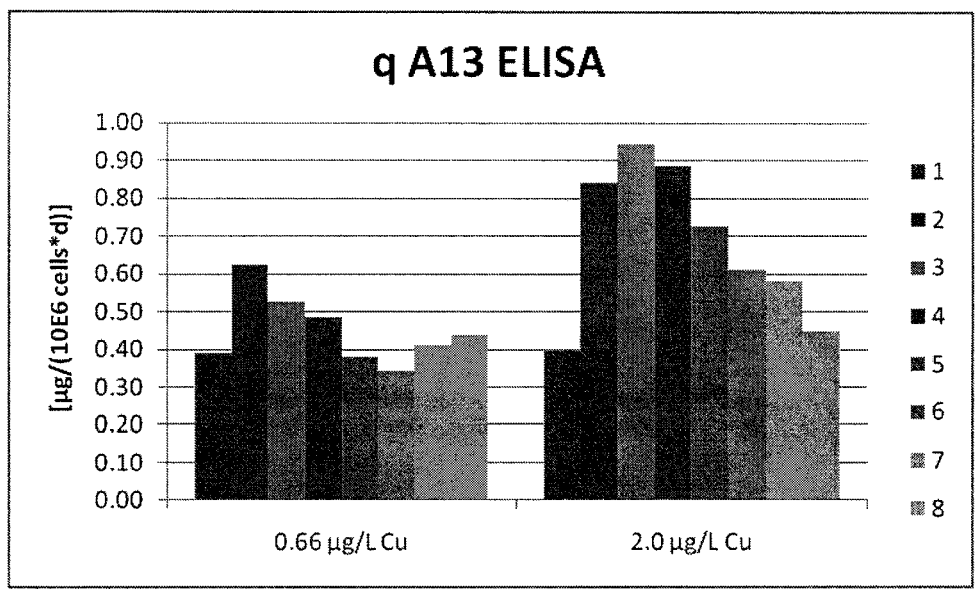

To estimate an optimal concentration of copper on the activity of rA13, an extrapolation of data from Table 15 of P Frets versus copper concentration (FIG. 4) shows that optimum effect is likely reached at about 2 μg/L, with a conservative estimation of a negative effect above about 4 μg/L.

TABLE 15

Expression of rA13 in mammalian cell culture performed in chemostatic continuous culture mode using media containing variable copper concentrations.

| 10 L Scale R&D Experiment Mean of 4 CST weeks | ZZ - NC [10E6 cells/mL] | P Frets [U/(L*d)] | q Frets [U/(10E9 cells*d)] | Spec. Activity U/mg |
|---|---|---|---|---|
| 0.66 μg/L $Cu^{2+}$ | 1.35 | 1322 | 1028 | 1759 |
| 1 μg/L $Cu^{2+}$ | 1.64 | 1962 | 1247 | 1690 |
| 4 μg/L $Cu^{2+}$ | 2.26 | 2960 | 1338 | 1768 |

Based on the results obtained above, an additional experiment was performed, which compared the expression of rA13 in cell culture media containing 0.66 μg/L copper with 2.0 μg/L copper. As shown in Table 16, supplementation of the basal cell media with copper, to a final concentration of 2.0 μg/L copper, resulted in a significant increase in volumetric (P) and specific (q) productivity expressed as the total rA13 activity produced per liter culture and day and the total rA13 activity produced per cell and day, respectively, over a period of 8 weeks. The specific data for each week of rA13 production in the two cultures is shown in FIG. 5. From these data, it is clear that copper supplementation has a measurable beneficial effect on cell metabolism, specific growth rate and rA13 productivity.

TABLE 16

Expression of rA13 in mammalian cell culture performed in chemostatic continuous culture mode using media containing variable copper concentrations.

| 10 L Scale Mean of 8 CST weeks | ZZ - NC [10E6 cells/mL] | P Frets [U/(L*d)] | q Frets [U/(10E9 cells*d)] | Spec. Activity U/mg |
|---|---|---|---|---|
| 0.66 μg/L $Cu^{2+}$ | 1.29 | 1049 | 821 | 1862 |
| 2 μg/L $Cu^{2+}$ | 2.17 | 2470 | 1146 | 1749 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for producing a recombinant Von Willebrand Factor (rVWF) composition, the method comprising the steps of:
    (a) providing a basal cell culture media;
    (b) supplementing the basal cell culture media with copper to provide a final copper concentration of at least 2.4 μg/L;
    (c) providing one or more cells comprising a nucleic acid encoding a rVWF protein;
    (d) culturing the one or more cells in the copper supplemented cell culture media such that rVWF is expressed and excreted from the cells into a culture supernatant and the $NH_4^+$ content of the cell culture supernatant is maintained at a concentration below 4 mM or below 10 mM; and
    (e) recovering at least a portion of the culture supernatant, wherein the recovered supernatant has a rVWF specific ristocetin cofactor activity of at least 30 mU/μg rVWF.

2. The method of claim 1, further comprising the step of supplementing the basal cell culture media with a hydrolysate prior to culturing the one or more cells.

3. The method of claim 2, wherein the hydrolysate is a plant hydrolysate.

4. The method of claim 3, wherein the hydrolysate is a soy hydrolysate.

5. The method of claim 1, wherein the basal cell culture media is an animal protein free culture media.

6. The method of claim 1, wherein the basal cell culture media is a protein free culture media.

7. The method of claim 1, wherein the basal cell culture media is a chemically defined culture media.

8. The method of claim 1, wherein the final copper concentration of the copper supplemented basal cell culture media is at least 4 μg/L copper.

9. The method of claim 1, wherein the final copper concentration of the copper supplemented basal cell culture media is between 2.4 μg/L and 20 μg/L copper.

10. The method of claim 1, wherein the copper supplementing the basal cell culture media is provided as a copper salt, a copper chelate, or a combination thereof.

11. The method of claim 10, wherein the copper salt is selected from the group consisting of copper sulfate, copper acetate, copper carbonate, copper chloride, copper hydroxide, copper nitrate, and copper oxide.

12. The method of claim 1, wherein the one or more cells are mammalian cells.

13. The method of claim 12, wherein the mammalian cells are CHO cells.

14. The method of claim 1, wherein culturing the one or more cells comprises batch cultivation of the cells.

15. The method of claim 1, wherein culturing the one or more cells comprises continuous cultivation of the cells.

16. The method of claim 15, wherein the continuous cultivation of cells is performed in chemostatic mode.

17. The method of claim 15, wherein the continuous cultivation of cells is performed in perfusion mode.

18. The method of claim 1, wherein the one or more cells is cultured in at least 100 L of the supplemented basal cell culture media.

19. The method of claim 1, wherein the cell density is maintained at less than $2.5 \times 10^6$ cells per mL during the step of culturing the one or more cells.

20. The method of claim 19, wherein the cell density is maintained at less than $2.0 \times 10^6$ cells per mL during the step of culturing the one or more cells.

21. The method of claim 19, wherein the cell density is maintained at less than $1.5 \times 10^6$ cells per mL during the step of culturing the one or more cells.

22. The method of claim 1, wherein the step of recovering at least a portion of the culture supernatant comprises filtration or centrifugation to remove cells from the portion of culture supernatant.

23. The method of claim 1, wherein the recovered supernatant has a rVWF specific ristocetin cofactor activity of at least 40 mU/μg rVWF.

24. The method of claim 23, wherein the recovered supernatant has a rVWF specific ristocetin cofactor activity of at least 50 mU/μg rVWF.

25. The method of claim 23, wherein the recovered supernatant has a rVWF specific ristocetin cofactor activity of at least 60 mU/μg rVWF.

26. The method of claim 23, wherein the recovered supernatant has a rVWF specific ristocetin cofactor activity of at least 70 mU/μg rVWF.

27. The method of claim 23, wherein the recovered supernatant has a rVWF specific ristocetin cofactor activity of at least 80 mU/μg rVWF.

28. The method of claim 1, wherein at least 10% of the rVWF in the supernatant is present in a high molecular weight VWF multimer of more than 10 dimers.

29. The method of claim 1, wherein at least 20% of the rVWF in the supernatant is present in a high molecular weight VWF multimer of more than 10 dimers.

30. The method of claim 1, wherein at least 30% of the rVWF in the supernatant is present in a high molecular weight VWF multimer of more than 10 dimers.

31. The method of claim 1, wherein the supernatant contains high molecular weight VWF multimers of 14 to 22 dimers.

32. The method of claim 1, wherein rVWF is co-expressed with recombinant Factor VIII (rFVIII).

33. The method of claim 32, further comprising a step of purifying rVWF away from at least 50% of the rFVIII present in the recovered supernatant.

34. The method of claim 33, wherein the ratio of rVWF to rFVIII after the purification step is at least 10:1.

35. The method of claim 1, wherein the method further comprises a rVWF enrichment step.

* * * * *